United States Patent [19]

Buschke

[11] Patent Number: 5,230,629

[45] Date of Patent: Jul. 27, 1993

[54] DEVICE AND METHOD FOR ASSESSING COGNITIVE SPEED

[75] Inventor: Herman Buschke, New York, N.Y.

[73] Assignee: Albert Einstein College of Medicine of Yeshiva University, Bronx, N.Y.

[21] Appl. No.: 988,021

[22] Filed: Dec. 9, 1992

Related U.S. Application Data

[63] Continuation-in-part of Ser. No. 663,363, Mar. 1, 1991, abandoned.

[51] Int. Cl.⁵ ............................................. G09B 19/00
[52] U.S. Cl. ................................. 434/236; 434/365; 273/454; 364/551.01
[58] Field of Search ............... 434/201, 236, 258, 322, 434/362, 365; 273/429, 430, 440, 454; 364/419, 551.01; 340/439, 573; 395/927

[56] References Cited

U.S. PATENT DOCUMENTS

| | | |
|---|---|---|
| 3,024,020 | 3/1962 | Alton . |
| 3,568,334 | 3/1971 | Gregorio . |
| 3,641,686 | 2/1972 | Krass . |
| 4,247,895 | 1/1981 | Weber . |
| 4,332,566 | 6/1982 | Mazeski et al. . |
| 4,337,047 | 6/1982 | Hatta . |
| 4,358,273 | 11/1982 | Yamamoto . |
| 4,464,121 | 8/1984 | Perelli . |
| 4,755,140 | 7/1988 | Rimland . |
| 4,770,636 | 9/1988 | Buschke . |
| 5,079,726 | 1/1992 | Keller .......................... 434/236 X |

OTHER PUBLICATIONS

Birren, J. E., Woods, A. M., & Williams, M. V., (1980), Behavioral slowing with age: Causes, organization and consequences, In L. W. Poon (Ed.), Aging in 1980's, (pp. 293-308, Wash., D.C.; American Psychological Association.

Cerella, J., (1985), Information processing rates in the elderly. Psychological Bulletin, 98, 67-83.

Cerella, J., (1990), Aging and information-processing rate, In Birren, J. E. & Shale, K. W. (Eds.), Handbook of the Psychology of Aging, (3rd Ed., pp. 201-221), N.Y. Academic Press.

Guy J. Groen et al., "A Chronometric Analysis of Simple Addition", Psychological Review, (1972), vol. 79, pp. 329-343, No. 4.

John M. Parkman et al., "Temporal Aspects of Simple Addition and Comparison", Journal of Experimental Psychology, (1971), vol. 89, No. 2, pp. 335-342.

Frank Restle, "Speed of Adding and Comparing Numbers", Journal of Experimental Psychology, (1970), vol. 83, No. 2, pp. 274-278.

John M. Parkman, "Temporal Aspects of Digit and Letter Inequality Judgments", Journal of Experimental Psychology, vol. 91, No. 2, (1971), pp. 191-205.

Thomas K. Landauer, "Rate of Implicit Speech", Perceptual and Motor Skills, (1962); vol. 15, p. 646.

Robert S. Moyer, Thomas K. Landauer, "Time Required for Judgments of Numerical Inequity", Nature, (1967), vol. 215, pp. 1519-1520.

Mary Beckwith and Frank Restle, "Process of Enumeration", Psychological Review, (1966), vol. 73, No. 5, pp. 437-444.

Primary Examiner—Richard J. Apley
Assistant Examiner—Joe H. Cheng
Attorney, Agent, or Firm—Amster, Rothstein & Ebenstein

[57] ABSTRACT

A cognitive speedometer for the assessment of cognitive processing speed includes a display screen, a keyboard, and a processor for generating original data and displaying on the screen the original data for copying by a user on the keyboard. Only if the user copies the displayed original data correctly, the processor generates and displays on the screen different data on which the user is to perform a unit cognitive operation and then enter the resultant data on the keyboard, the resultant data having the same characters as the original data. Only if the user enters the correct resultant data, the processor determines the time required for the user to perform the unit cognitive operation.

30 Claims, 5 Drawing Sheets

DEVICE AND METHOD FOR ASSESSING COGNITIVE SPEED

This is a continuation-in-part of copending application Ser. No. 07/633,363 filed on Mar. 1, 1991, abandoned.

BACKGROUND OF THE INVENTION

The present invention relates to a cognitive speedometer for the assessment of cognitive processing speeds, and more particularly to a portable electronic cognitive speedometer.

U.S. Pat. No. 4,770,636 discloses a cognometer useful in the repeated testing of memory and concentration, as needed to identify declining cognitive function that may require medical evaluation for dementia, delirium, other medical or psychiatric illness, or the cognitive side-effects of medications. The apparatus therein described permits repeated cognitive monitoring to be carried out not only in a medical setting, but also alone at home, through the provision of a device for automated, easily repeated testing. The cognitive functions determined by the apparatus set forth therein are memory and concentration, rather than the speed of the cognitive functions. While memory and concentration are particularly useful foci in many instances, particularly those involving the elderly or the severely affected, in other instances the primary focus should be on the speed with which a cognitive function is performed. For example, airplane pilots, racing car drivers and many others are required to make decisions not only accurately, but also rapidly.

The cognometer provides self-based testing expressly to compensate for the cognitive slowing often present in aged or cognitively impaired persons, although response speed was measured and reported in order to enable identification of excessive slowing which could be an early indication of an impaired cognitive processing. By way of contrast, the present invention is directed to a cognitive speedometer for the assessment of cognitive processing speed with fineness and sensitivity. This is accomplished by determining the cognitive processing speed independently of the time required to physically respond to the test stimulus. Such a test must measure only the ability in question and not be affected by other considerations, such as the physical functions of the individual being tested. For example, if a person has manual dexterity problems which interfere with his reproducing a displayed number on a keyboard, an excessive time to key in an answer in response to a presented arithmetic problem does not necessarily reflect on the speed of his cognitive processing. Thus, it is critical that any cognitive speedometer test isolate the cognitive function.

Automated testing should provide reliable, rapid, and automatic administration, scoring, and reporting so that repeated testing can be carried out reliably in precisely the same way as frequently as desired, at home as well as in medical settings. This permits self-testing by the general public, and monitoring of patients with suspected cognitive impairment, at home as well as in medical offices, clinics, emergency rooms, hospital wards, psychiatric facilities, or nursing homes.

In order for the test to have validity as an indication of cognitive processing speed, as independent as possible of intelligence, education and the like, the cognitive function to be performed during the test should be short, simple and capable of being performed in only one manner. To this end, the apparatus should test a unit or single cognitive operation as opposed to a complex set of cognitive operations which might be strongly affected by the intelligence of the test taker, the manner in which he approached the problem or performed the arithmetic operation, etc. For example, certain arithmetic problems can be solved more easily and faster by successive approximation until the right answer is obtained than through the set of arithmetic operations intended by the problem framer—e.g., a long division problem or a solution to a complex equation.

The measurement of cognitive speed by conventional techniques—such as comparison of simple and multiple choice reaction times, Sternberg's memory scanning paradigm, or speed of mental rotation—have not proven to be entirely satisfactory. Some of these methods appear to measure the time needed to carry out more than one cognitive operation because they require a cognitive decision in addition to the operation(s) involved in their mental comparisons. Some of these rely on yes/no responses which allow guessing with a high probability of correct guessing rather than accurately measuring cognitive speed. Thus, the need remains for a cognitive speedometer which is designed to measure the speed of a single cognitive operation without reflecting the time needed to enter the result, requires specific numerical responses that cannot be guessed or anticipated, and does not require the kind of decisions needed for yes/no responses. The measures provided by such a cognitive speedometer should reflect the speed of a single cognitive operation, without additional variance due to decision latencies, and without contamination by rapid guesses, so that the latencies should provide more accurate statistics, and the fastest responses should provide a more accurate measure of maximum cognitive speed.

Accordingly, it is an object of the present invention to provide a reliable, rapid, automatic administration, scoring and reporting test for self-testing at home or elsewhere of cognitive processing speed.

Another object is to provide such a test which assesses the cognitive processing speed in performing a cognitive operation without reflecting physical ability.

A further object is to provide such a device which tests the cognitive processing speed in performing a unit or single cognitive operation (as opposed to a set of cognitive operations).

SUMMARY OF THE INVENTION

It has now been found that the above and related objects of the present invention are obtained in a first embodiment of a cognitive speedometer for the assessment of cognitive processing speed. The speedometer is an electronic device programmed for repeated, rapid, automated assessment and monitoring of cognitive processing speed. The speedometer includes display means, such as a LED or CRT screen, and means for entering data, such as a keyboard. Means generate original data and display on the display means the original data for copying by a user on the data entry means. Means, operable only on the displayed original data correctly copied by the user on the data entry means, generate and display on the display means different data on which the user is to perform at least one unit cognitive operation and then enter the resultant data on the data entry means. Means, operable only on the correct resultant data entered by the user on the data entry means, determine the time required for the user to perform the unit cognitive operation. Preferably the resultant data has the same characters as the original data.

In a preferred version of the first embodiment, the determining means determines the time required for the user to perform the unit cognitive operation as the difference between the time required to copy the displayed original data correctly on the data entry means and the time required to perform a unit cognitive operation on the displayed different data and then enter the resultant data correctly on the data entry means. The determining means determines the time required to perform the unit cognitive operation independently of the time required to physically enter the resultant data on the data entry means by determining the difference between the times by calculation.

Means are preferably provided for comparing the time required for the user to perform the unit cognitive operation with an established norm for the time required to perform the unit cognitive operation. In one instance the comparing means compares the time required to perform the unit cognitive operation as determined by the determining means with an objective norm determined by use of the cognitive speedometer on individuals like the user in like situations. In another instance the comparing means compares the time required to perform the unit cognitive operation as determined by the determining means with a subjective norm established for the individual user by prior use of the cognitive speedometer.

Preferably the original and different data are numeric (especially numbers having no more than two digits), and the unit cognitive operation is arithmetic (especially the addition or subtraction of 1 to or from the displayed different data). The cognitive speedometer additionally includes prompting means for indicating on the display means at an appropriate time instructions for the user to copy the displayed original data or the unit cognitive operation to be performed by the user on the displayed different data.

The user's speed of cognitive processing per unit of time is determined by dividing a unit of time by the number of unit cognitive operations performed per unit of time by the user.

The means for generating and displaying original data preferably generates and displays a sequence of such original data for copying before the means for generating and displaying the different data displays such different data.

The present invention also encompasses a method of assessing cognitive speed comprising the steps of generating and displaying data on a display means, and testing the user's speed of entering the data by displaying the data on the display means and requiring the user to copy the data on a data entry means. The cognitive speed of the user is tested by displaying different data on the display means and requiring the user to perform a cognitive operation on the different data and enter the resultant data on the data entry means. The time required for the user to perform the cognitive operation is determined. Preferably the originally displayed data and the (correct) resultant data are the same. The cognitive speed is tested only with regard to originally displayed data correctly copied by the user, and the time is determined only with regard to the resultant data correctly entered by the user.

A second embodiment of the cognitive speedometer for the assessment of cognitive processing speed comprises display means, means for entering data, and means for generating and displaying on the display means data on which the user is to perform a plurality of tasks involving different numbers of cognitive operations and then enter the resultant data on the data entry means. Means are also provided for determining the time required for the user to perform a unit cognitive operation from the times required to perform the tasks.

In a preferred version of the second embodiment, the determining means determines the time required for the user to perform the unit cognitive operation as the slope of the linear function associated with the set of points in X, Y coordinates, where Y is the variable associated with the time required for the user to perform the tasks and then enter the resultant data on the data entry means, and X is the variable associated with the number of unit cognitive operations involved in the respective tasks. The determining means uses only the tasks for which the user enters the correct resultant data on the data entry means and determines the time required to perform the unit cognitive operation independently of the time required to physically enter the resultant data on the data entry means.

A second embodiment of the method of assessing cognitive speed comprises the steps of generating and displaying data on a display means, testing the cognitive speed of the user by requiring the user to perform a plurality of tasks involving different numbers of cognitive operations on the data and enter the resultant data on the data entry means, and determining the time required for the user to perform a unit cognitive operation from the times required to perform the tasks.

The present invention also encompasses a cognometer comprising in combination in a single portable device a speed monitor, a memory monitor, a concentration monitor, and means for actuating one of the monitors at a time.

BRIEF DESCRIPTION OF THE DRAWING

The above brief description, as well as further objects, features and advantages of the present invention, will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
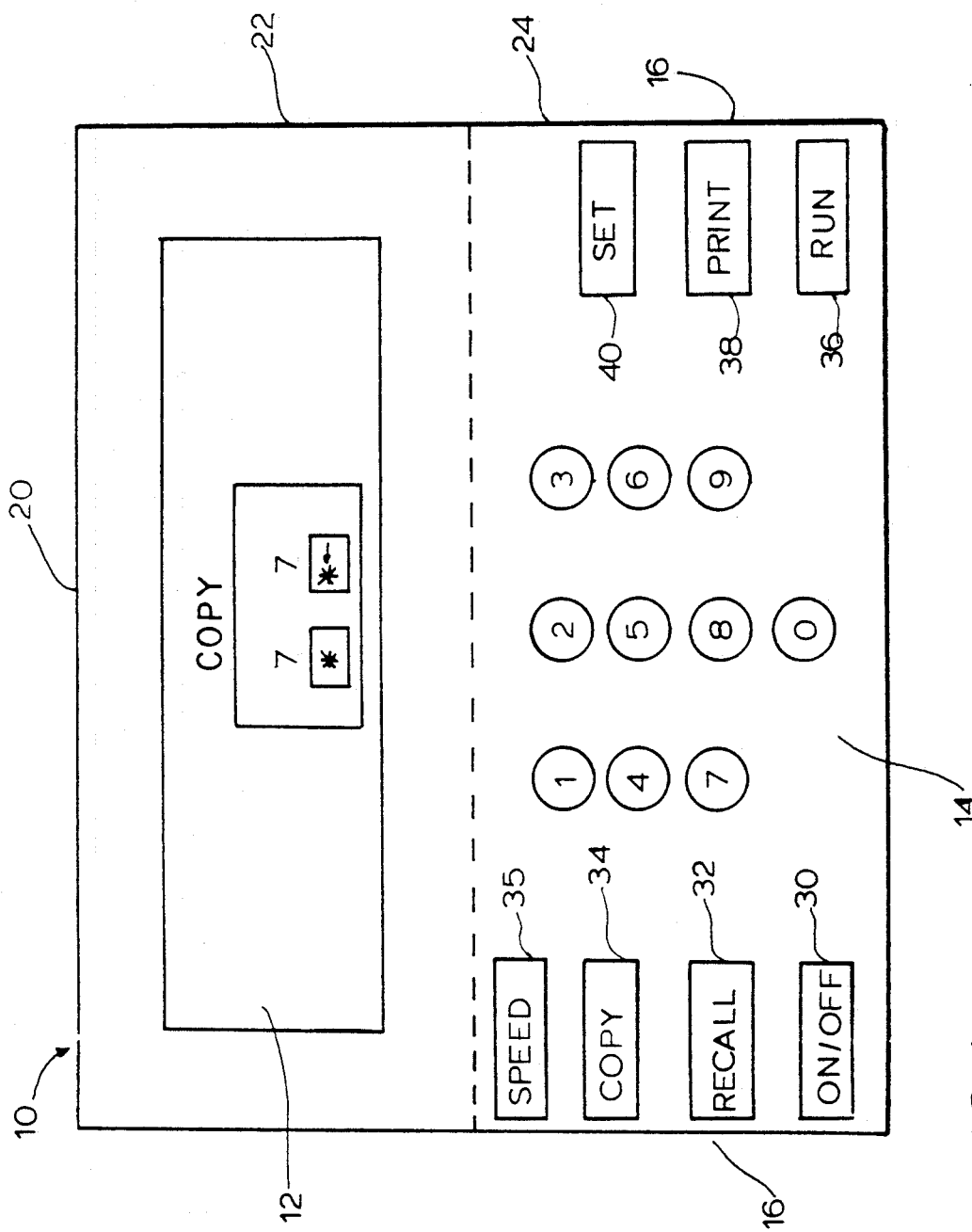
FIG. 1 is a top plan view of a cognometer embodying a cognitive speedometer according to the present invention.

Referring now to the drawing, and in particular to FIG. 1 thereof, therein illustrated is a cognometer, generally designated by the reference numeral 10, embodying the principles of the present invention. The cognometer is a small, portable electronic device programmed for repeated, rapid, automated assessment and monitoring of memory, concentration and cognitive speed, which are sensitive, early and prominent indicators of cognitive impairment. The cognometer 10 is similar to a small electronic calculator, consisting of and LED or CRT screen, generally designated by the reference numeral 12, to show stimuli (such as numbers and instructions); a set of response keys, generally designated by the reference numeral 14, numbered from 0-9; a set of control keys, generally designated by the reference numeral 16; and microchip firmware (not shown) incorporating the programs for testing memory, concentration and cognitive speed. The cognometer's upper face, generally designated by the reference numeral 20, is generally divided into two portions: an upper portion 22 containing the screen 12, and a lower portion 24 containing the response key set 14 and the control key set 16. The plane of the upper portion 22 may be tilted upwardly at an angle to the plane of the lower portion 24 to facilitate reading of the screen 12. The control key set 16 may be disposed in one location or, as illustrated, divided into semi-sets disposed to either side of the response key set 14.

While other embodiments of the present invention may employ alphabetic or alphanumeric response keys, the preferred embodiment illustrated in FIG. 1 utilizes a keyboard of exclusively numeric response keys so that the test results should not be affected by education, language or cultural background because the stimuli and responses are simple digits from 0 through 9. Anyone who can read numbers and press numbered keys should be able to use the various tests therein easily, and anyone who can further read the simple control keys should be able to use the cognometer without assistance.

The control key set 16 includes the following keys: beginning at the left side of the cognometer shown in FIG. 1, ON/OFF key 30 (for turning the cognometer on and calling up the initializing or opening program), RECALL, COPY and SPEED keys 32, 34, and 35 for calling up the memory monitor, concentration monitor and speed monitor programs, respectively; turning now to the right side of the cognometer shown in FIG. 1, RUN key 30 (to start the selected test), PRINT key 38 (to activate an optional paper tape printer to record the test scores), and SET key 40 (to perform the setting of non-default parameters for the selected test).

Figure 2:
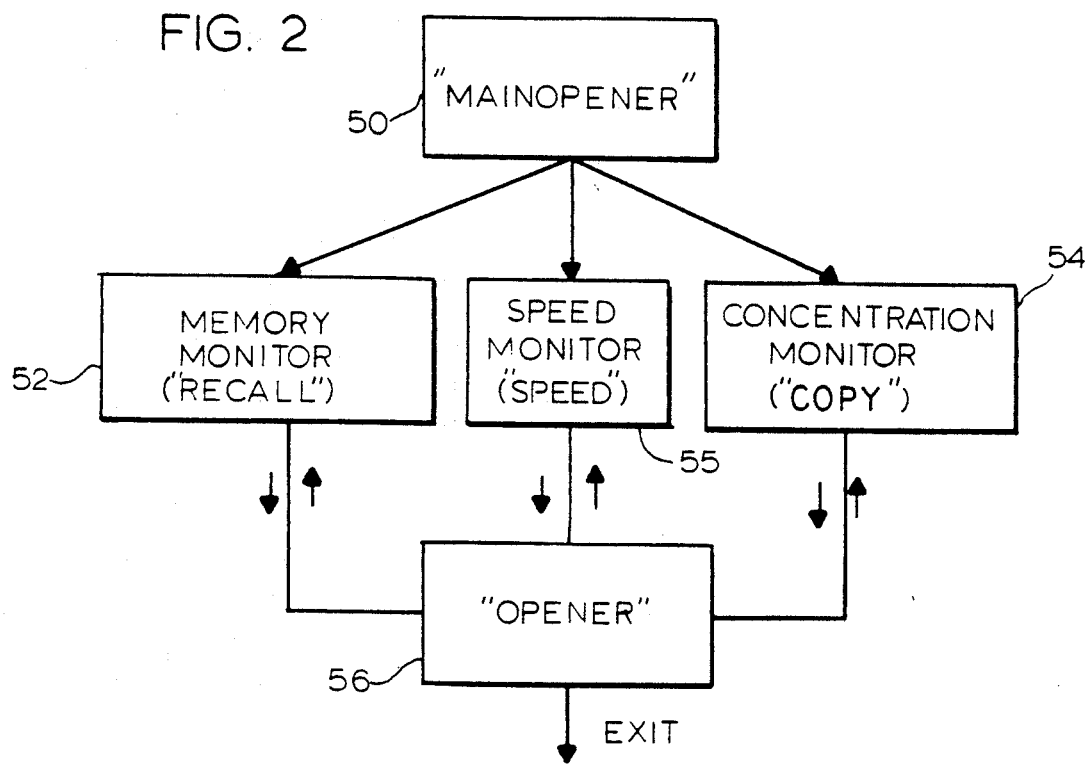
FIG. 2 is an overall flow chart of the operation of the cognometer.

Referring now to FIG. 2 in particular, the software for the cognometer 10 consists of five programs (copy appended). "MAINOPENER" program 50 is initially loaded into memory. The "MAINOPENER" program 50 may provide for entry of data of general utility such as a patient code number identifying the particular patient, his age and the like. Date and time may also be entered in this manner; however, the cognometer itself preferably includes means (e.g., an electronic calendar and clock) for providing this information to the memory. The user can then select either the "MEMORY MONITOR" program 52, the "CONCENTRATION MONITOR" program 54, or the "SPEED MONITOR" program 55, by actuating the RECALL key 32, the COPY key 34, or the SPEED key 35, respectively. Actuation of the appropriate key 32, 34, 35 causing the appropriate monitor 52, 54, 55 to be loaded into memory. The user then activates the SET key 40 to enter the non-default test parameters or the RUN key 36 to start running of the test with default test parameters for all parameters not previously set with the SET key 40. When the monitor 52, 54, 55 in memory has completed its various tests, the user is turned over to the "OPENER" program 56, which affords him an opportunity to proceed to any of the monitor programs 52, 54, 55. Thus, the user is able to switch back and forth between the memory, concentration and speed monitor programs easily and rapidly. The user can, of course, terminate the session with the cognometer entirely by use of the ON/OFF key 30 or by simply not responding to the "OPENER" program 56 for a given period of time (for example, three minutes).

Staged testing, in which each stage must be successfully completed before testing the next stage, is used in each monitor. It does not seem reasonable to test a cognitive operation speed unless the digits presented on the screen 12 can be copied correctly by the user onto the key set 14. Therefore, in the speed monitor, cognitive speed is not tested until the digits have been copied correctly.

The "MEMORY MONITOR" program 52 and the "CONCENTRATION MONITOR" program 54 are fully described in the aforementioned U.S. Pat. No. 4,770,636 and hence will not be set forth again herein, as that patent is expressly incorporated by reference herein. It will be appreciated, however, that the cognometer 10 may include one or both of these programs as well as the "SPEED MONITOR" program 55, to be described hereinbelow, or may consist exclusively of the "SPEED MONITOR" program 55.

THE SPEED MONITOR

Figure 3:
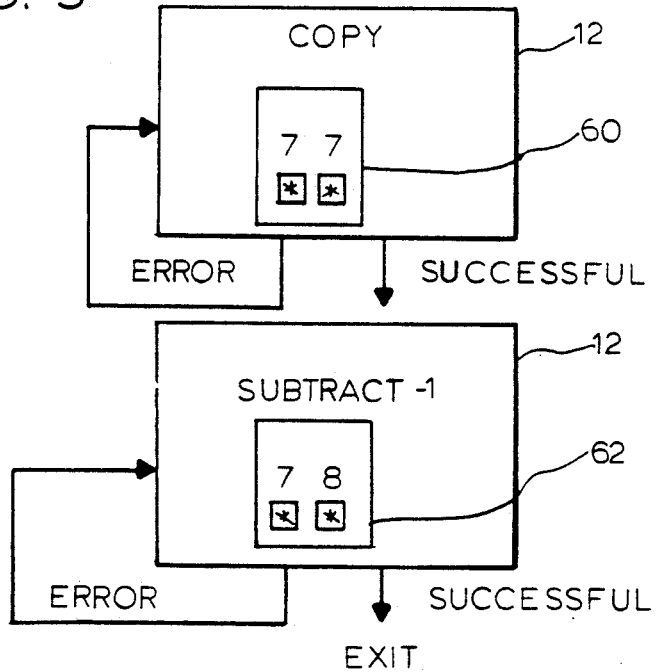
FIG. 3 is a flow chart for a first embodiment of the cognitive speedometer.

Referring now in particular to FIG. 3, therein illustrated is a flow chart for a first preferred embodiment of the speed monitor program 55. Briefly speaking, the speed monitor is programmed to assess the speed of cognitive processing by measuring the difference between the time needed to copy arithmetic data (such as a two-digit number) and the time needed to carry out an arithmetic computation on such numbers (such as subtracting or adding "1") and enter the result. Although other computations or transformations can be used, subtraction or addition of 1 are preferred because these computations appear to involve only a single specific cognitive operation, so that the speed can be used to measure the speed of cognitive processing for a single or unit cognitive operation. The latency or time needed to copy or to subtract or add is measured from onset of the number on the screen to the entry of the first digit of the two-digit response number. Copying and subtracting or adding 1 both involve reading a number and entering a number, and appear to differ therefrom only in the cognitive processing needed for the cognitive operation of subtracting or adding 1. Therefore, the difference between the copying latency and the latency for adding or subtracting 1 (or other transformation) should be the latency of the cognitive processing above. While median or mean latencies may be used, median latencies are preferred to avoid or minimize the effects of atypical very long or very short latencies ("outliners"). Thus, the median latency for copying ("C") is subtracted from the median latency for subtraction or addition ("S"), and the difference (S−C) provides a measure of the median time needed to carry out the cognitive operation or transformation. The speed of cognitive processing (for this cognitive operation) can be obtained by dividing 1000 milliseconds by the difference between subtraction and copying latencies (S−C) measured in milliseconds:

cognitive speed = $1000/(S-C)$ operations per second

The numbers presented for the arithmetic or computational operation are preferably selected so that the same numbers are entered in copying and the arithmetic operation; thus, each number presented for the subtraction of 1 is 1 more than its paired number presented for copying (e.g., copying "64" and subtracting 1 from "65" both require the entry of "64"), and each number presented for the addition of 1 is 1 less than its paired number. The user copies each of 20 (or more) randomly generated numbers presented one at a time, and then subtracts 1 from or adds 1 to each of 20 (or more) numbers presented one at a time, so that the same numbers will be entered by the user in copying and in subtracting or adding. The numbers for the arithmetic operation are presented either in the same order as their paired copy numbers or in random order. Alternating runs of copying and arithmetic operations can be repeated to obtain additional data and counterbalance any effects of practice or fatigue. If desired, copying and arithmetic operations can be combined within the same block to further assist in keeping the user alert, with the copy trials and arithmetic trials either alternating or being in random order within a block.

For various reasons, the arithmetic operation is preferably addition rather than subtraction, although either addition or subtraction, or both, may be used.

While, as indicated above, the numbers presented for the arithmetic operation are preferably selected so that the same numbers are to be entered in both the copying operation and the arithmetic operation in order to minimize any differences in the physical activities required of the user, this is not believed to be critical. It is believed that approximately the same results are obtained if the same digits are to be entered, even though the order in which they are entered by the user may differ—for example, the number to be copied may be "12" and the result of the arithmetic operation to be entered may be "21." Especially where the number of trials is large, unrelated numbers may be used (regardless of the specific digits or the order thereof), as the physical differences in striking one digit key 14 as opposed to another will average out over the number of trials. In such a case, separately randomly generated numbers may be used for both the copying and arithmetic operations.

Each number to be copied or transformed by the operation of subtracting or adding 1 is shown in a box 60, 62 in the center of the screen 12, remaining until a response number has been entered. An instruction to "Copy" (see above box 60) or to "Subtract −1" or to "Add +1" see above box 62) is shown on the screen 12 above the box 60, 62 so that the user does not need to remember what to do. The instruction initially appears a preselected period (e.g., 200 milliseconds) before the number appears so that the user is aware of the instruction before he sees the number. The next number is presented a preselected period (e.g., 2 seconds) after the previous number has been entered by the user. Alternatively, the presentation of the next number may be delayed until the user strikes a particular key (for example, the zero key or a space bar) to indicate that he is ready, with the next number being presented a preselected period (e.g., two seconds) after the key is struck. Preferably an alerting tone is sounded just before a number appears to alert the user that the number will shortly be presented.

The user should respond as quickly as possible while being careful to give correct responses. Errors in copying or subtracting are not corrected because the latency of a response corrected after an error is not meaningful, but errors may be indicated by a "beep" to keep the error rate low. Errors can be replaced by generation of additional random numbers for copying (in box 60) or additional numbers for subtraction (in box 62) so that each run or block of copying or arithmetic will include the same number of trials with correct responses. Where an incorrect result is obtained during the test, this is indicated in the raw data of the test results by a "−1" or "E", or some other indication of the fact that the response was erroneous and therefore gave an unreliable response time. If the number of errors in a given run or block is too great (e.g., greater than 10%), the run or block is discontinued and the results discarded on the assumption that the user may have been distracted; in such an instance, the run or block is then automatically repeated. Otherwise the timer associated with erroneous responses are simply ignored in determining the time for a unit cognitive operation.

Presentations stop when all 20 (or more) numbers in a run or block have been presented. The user can start the next run or block by pressing an appropriate key when ready.

The data obtained include copying latencies, computation latencies (both including the time required to enter the results), and by calculation the difference between copying and computation latencies, which difference reflects the time needed to carry out the single cognitive operation, e.g., addition or subtraction. After each test of copying and computation is completed, these latencies or speed scores can be shown on the screen 12. Individual scores are saved in personal baseline files, so each person's current performance can be compared to their own previous baseline performance. Current scores flash if they are below the baseline scores.

Cognitive speed also can be assessed by measuring the times needed to copy and to subtract or add 1 to single digit numbers, thereby to estimate the time needed for a single computation or cognitive operation by the difference between copying latency and computation latency. Sequences of 20 (or more) digits randomly selected from 1 to 8 are presented one digit at a time, and the user either copies or subtracts 1 or adds 1 to each digit as it is presented.

The assessment of cognitive speed by comparing the time needed to copy and the time needed to subtract or add 1 (and enter the result) can be extended by measuring the time needed to subtract or add 1, 2, 3 (or more), to determine if an increasing linear function is obtained as the number of cognitive computations increases. Such a function would be consistent with the possibility that subtracting 1 involves 1 cognitive operation, subtracting 2 involves 2 cognitive operations, subtracting 3 involves 3 cognitive operations, and so forth. The slope of such a linear function provides a measure of the speed of such cognitive computations, and the intercept provides a measure of the task latency without computation (i.e., when computation load is zero). The slope can be evaluated by assessing linearity and squaring the correlation between the computational loads and their latencies to determine how much of the variance is accounted for by the linear function. The assumption that the difference between copying latency and computation latency is sufficient for accurate measurement of cognitive speed can be supported by comparing this measure with the slope to confirm that they are equivalent. The assumption that copying and subtracting (or adding) 1 differ only in that one additional operation is needed to subtract (or add) 1 can be supported by comparing the copying latency and the intercept latency to confirm that the copying latency provides an adequate measure of the intercept. It has been found that the linear function accounts for nearly all of the variance, and the copying latency provides an adequate estimate of the intercept, thus supporting the assumption that a comparison of latency to copy and latency to subtract or add 1 is sufficient to estimate cognitive speed for such cognitive computations.

The program scores the test automatically and shows the test scores on the screen. Hard copy can be sent to the printer (e.g., a paper tape printer) by use of the print key 38. A full version of the printout, as illustrated in Table I, includes identifying data, and separate blocks for each cognitive operation performed. Thus, the printout includes for each block an identification of the cognitive function (e.g., "copy," "subtract −1," "subtract −2," "subtract −3," etc.), the stimuli (the randomly generated digits originally displayed on the screen for copying), the answers (i.e., the correct answers), the response (i.e., the digits entered on the keys 14), and the RT (i.e., the Response Time required by the user). Also presented are summaries of useful information, such as the mean response time of the correct trials, the standard deviation, the median, the low, the high and the quartile. Whereas the answers for the "copy" block will be the same as the stimuli, in the other blocks where addition or subtraction is required, the answers will differ appropriately from the stimuli.

The failure to enter a correct response is indicated by a "−1" for the response time for that trial. If desired, as indicated, the number of erroneous trials in a given block may be indicated, as well as the average response time for the erroneous trials and the standard deviation associated therewith where there is more than one error trial in a given block. Thus, even where the time required for the user to incorrectly perform the unit cognitive operation (including entering the response) is determined by the processor, such a misleading response time is not deemed or treated as a time required for the user to perform a unit cognitive operation due to the erroneous nature of the response. This is true even though the unit cognitive operation may have been performed correctly and the correct result merely incorrectly entered upon the keyboard. The processor determines the time required for the user to perform the unit cognitive operation as such only where the user has correctly entered the result, thereby to avoid the introduction of misleading response times.

Alternatively, or in addition to the test results of Table I, the pertinent information may be presented in a more condensed form, as shown in Table II, including the same identification data, a column for the stimuli (that is, the randomly generated digits originally displayed), the response times for the various blocks under appropriate headings, and the summary of useful information. Thus, in the condensed form of the report, the answers and responses are not provided, although the stimulus and response times are. In the condensed form, the failure to enter a correct response is indicated by an "E" (for "error"), and "N" is used to represent the number of correct responses in a block.

During entry of the variable parameters, the type of printout desired (in the form of Table I or Table II) may be elected.

The results reflected in Tables I and II characterize the user's response times for copying and for various unit and complex cognitive functions (that is, subtraction of one and subtraction of greater numbers, respectively). These results may be compared either manually or by the cognometer with subjective norms such as previous results (e.g., base line results) for the same user in order to compare the cognitive status of the user over time. This type of investigation is especially useful to determine whether the user is presently on drugs or like medication which impair the speed of the cognitive function, to determine the effects of aging, to follow the course of an illness affecting cognitive function, and the like. Alternatively, or in addition thereto, the results can be compared, again either manually or by the cognometer, with an objective norm such as one previously determined for like users (e.g., persons of the same age, sex, and the like) either generally or under like particular circumstances (e.g., similar stress-inducing situations). It will be appreciated that the objective norm (that is, the norm of like users in like situations) may be a very limited or exclusive norm characteristic of a population with a particularly high or low cognitive processing speed—for example, an objective norm established for a population of racing car drivers or pilots may be substantially faster than a norm established for a population of ordinary persons of like sex and age.

After the score is reported, the "SPEED MONITOR" program terminates and the "OPENER" program is loaded. Then the user can run the speed monitor again with new random numbers, using the same or new parameters, can move to the memory or concentration monitors, or can terminate the session.

The following test parameters, among others, can be varied, the recommended default values being underlined:

1. External parameter file (N)
2. One (1) or two (2) digit numbers
3. Number of blocks (4)
4. Number of trials per block (30)
5. Number of practice trials (0)
6. Random digits in every block (1) or only first block (2)
7. Same order (1) or randomized (2) across blocks
8. Interstimulus interval (1) or space bar (2)
9. Interstimulus duration in seconds (2)
10. Delay after space bar in seconds (2)
    Block 1
11. Operation: copy (1), Add (2), Subtract (3), Alternate (4), or Random (5)
12. Number desired (1)
    Block 2
13. Operation: Copy (1), Add (2), Subtract (3), Alternate (4), or Random (5)
14. Number desired (1)
15. Same sample (1) or same response (2)

Thus, the user determines first whether to use the values previously set forth for the user and maintained in an external parameter file or whether to enter new parameter values. If the decision is to enter new values, he then determines the general nature of the test. First, the user determines whether one- or two-digit numbers will be used in each trial. Then, the user determines the number of blocks per test, and the number of trials per block. A number of practice trials can be designated, if desired. The numbers presented within each block can be random, or only the numbers in the first block can be made random. The numbers or paired numbers can be presented in the same order across several blocks or randomized. The interstimulus interval—that is, the time delay after the entry of a response before the next number is presented for copying or an arithmetic operation—can be set. The interstimulus interval can also be set for a time delay after the user indicates he is ready by hitting a space bar or some other key.

TABLE I

| | ID: | | | | 123 | | | | |
|---|---|---|---|---|---|---|---|---|---|
| | SEX: | | | | Male | | | | |
| | STUDY: | | | | Demo | | | | |
| | DATE: | | | | 9-08-89 | | | | |
| | TIME: | | | | 9:50 | | | | |

RESULTS OF BLOCK [1]: COPY

| STIMULI | 74 | 83 | 62 | 95 | 46 | 22 | 93 | 76 | 35 | 75 |
|---|---|---|---|---|---|---|---|---|---|---|
| | 65 | 24 | 31 | 44 | 85 | 84 | 52 | 26 | 25 | 82 |
| | 63 | 96 | 32 | 91 | | | | | | |
| ANSWERS | 74 | 83 | 62 | 95 | 46 | 22 | 93 | 76 | 35 | 75 |
| | 65 | 24 | 31 | 44 | 85 | 84 | 52 | 26 | 25 | 82 |
| | 63 | 96 | 32 | 91 | | | | | | |
| RESPONSE | 74 | 83 | 62 | 95 | 46 | 22 | 93 | 76 | 35 | 75 |
| | 65 | 24 | 31 | 44 | 85 | 84 | 52 | 26 | 25 | 82 |
| | 63 | 96 | 32 | 91 | | | | | | |
| RT | 1160 | 1002 | 891 | 955 | 1322 | 859 | 859 | 860 | 1307 | 796 |
| | 1146 | 844 | 875 | 812 | 844 | 924 | 1003 | 844 | 828 | 828 |
| | 859 | 860 | 1051 | 891 | | | | | | |

MEAN OF CORRECT TRIALS = 942   STANDARD DEVIATION = 151
MEDIAN = 867   LOW = 796   HIGH = 1322   QUARTILE = 79

RESULTS OF BLOCK [2]: SUBTRACT - 1 (SAME RESPONSES)

| STIMULI | 75 | 84 | 63 | 96 | 47 | 23 | 94 | 77 | 36 | 76 |
|---|---|---|---|---|---|---|---|---|---|---|
| | 66 | 25 | 32 | 45 | 86 | 85 | 53 | 27 | 26 | 83 |
| | 64 | 97 | 33 | 92 | | | | | | |
| ANSWERS | 74 | 83 | 62 | 95 | 46 | 22 | 93 | 76 | 35 | 75 |
| | 65 | 24 | 31 | 44 | 85 | 84 | 52 | 26 | 25 | 82 |
| | 63 | 96 | 32 | 91 | | | | | | |
| RESPONSE | 74 | 83 | 62 | 95 | 46 | 22 | 93 | 76 | 35 | 75 |
| | 65 | 24 | 31 | 44 | 85 | 84 | 52 | 26 | 25 | 82 |
| | 63 | 96 | 32 | 9i | | | | | | |
| RT | 888 | 1466 | 988 | 939 | 1179 | 844 | 1035 | 1003 | 1529 | 1115 |
| | 1083 | 924 | 923 | 940 | 907 | 939 | 1194 | 1227 | 1306 | 908 |
| | 1067 | 924 | 924 | 940 | | | | | | |

MEAN OF CORRECT TRIALS = 1050   STANDARD DEVIATION = 183
MEDIAN = 964   LOW = 844   HIGH = 1529   QUARTILE = 112

RESULTS OF BLOCK [3]: SUBTRACT - 2 (SAME RESPONSES)

| STIMULI | 76 | 85 | 64 | 97 | 48 | 24 | 95 | 78 | 37 | 77 |
|---|---|---|---|---|---|---|---|---|---|---|
| | 67 | 26 | 33 | 46 | 87 | 86 | 54 | 28 | 27 | 84 |
| | 65 | 98 | 34 | 93 | | | | | | |
| ANSWERS | 74 | 83 | 62 | 95 | 46 | 22 | 93 | 76 | 35 | 75 |
| | 65 | 24 | 31 | 44 | 85 | 84 | 52 | 26 | 25 | 82 |
| | 63 | 96 | 32 | 91 | | | | | | |
| RESPONSE | 74 | 83 | 62 | 95 | 46 | 22 | 93 | 76 | 35 | 75 |
| | 65 | 24 | 31 | 44 | 85 | 84 | 52 | 26 | 25 | 82 |
| | 63 | 96 | 32 | 92 | | | | | | |
| RT | 1032 | 987 | 1068 | 1035 | 1242 | 812 | 1163 | 1083 | 1003 | 955 |
| | 1179 | 1068 | 1067 | 1418 | 1768 | 940 | 1275 | 940 | 859 | 1227 |
| | 908 | 908 | 1402 | −1 | | | | | | |

MEAN OF CORRECT TRIALS = 1102   STANDARD DEVIATION = 217
MEDIAN = 1067   LOW = 812   HIGH = 1768   QUARTILE = 144
MEAN OF ERROR TRIALS [1] = 1131   STANDARD DEVIATION = 0

RESULTS OF BLOCK [4]: SUBTRACT - 3 (SAME RESPONSES)

| STIMULI | 77 | 86 | 65 | 98 | 49 | 25 | 96 | 79 | 38 | 78 |
|---|---|---|---|---|---|---|---|---|---|---|
| | 68 | 27 | 34 | 47 | 88 | 87 | 55 | 29 | 28 | 85 |
| | 66 | 99 | 35 | 94 | | | | | | |
| ANSWERS | 74 | 83 | 62 | 95 | 46 | 22 | 93 | 76 | 35 | 75 |
| | 65 | 24 | 31 | 44 | 85 | 84 | 52 | 26 | 25 | 82 |
| | 63 | 96 | 32 | 91 | | | | | | |
| RESPONSE | 74 | 83 | 62 | 95 | 46 | 22 | 93 | 76 | 35 | 75 |
| | 65 | 24 | 31 | 43 | 85 | 84 | 62 | 26 | 25 | 84 |
| | 63 | 96 | 32 | 92 | | | | | | |
| RT | 1176 | 972 | 1163 | 1068 | 1976 | 972 | 1211 | 1322 | 1020 | 1418 |
| | 1355 | 1386 | 1163 | −1 | 1016 | 1259 | −1 | 1127 | 1179 | −1 |
| | 1111 | 892 | 1068 | −1 | | | | | | |

MEAN OF CORRECT TRIALS = 1193   STANDARD DEVIATION = 234
MEDIAN = 1163   LOW = 892   HIGH = 1976   QUARTILE = 123
MEAN OF ERROR TRIALS [4] = 1466   STANDARD DEVIATION = 459

TABLE II

| ID: | 123 |
|---|---|
| AGE: | 99 |
| SEX: | Male |
| STUDY: | Demo |
| DATE: | 9-08-89 |
| TIME: | 9:50 |

TABLE II-continued

| # | Copy 1 | −1 2 | −2 3 | −3 4 |
|---|---|---|---|---|
| 74 | 1160 | 888 | 1032 | 1176 |
| 83 | 1002 | 1466 | 987 | 972 |
| 62 | 891 | 988 | 1068 | 1163 |
| 95 | 955 | 939 | 1035 | 1068 |
| 46 | 1322 | 1179 | 1242 | 1976 |
| 22 | 859 | 844 | 812 | 972 |
| 93 | 859 | 1035 | 1163 | 1211 |
| 76 | 860 | 1003 | 1083 | 1322 |
| 35 | 1307 | 1529 | 1003 | 1020 |
| 75 | 796 | 1115 | 955 | 1418 |
| 65 | 1146 | 1083 | 1179 | 1355 |
| 24 | 844 | 924 | 1068 | 1386 |
| 31 | 875 | 923 | 1067 | 1163 |
| 44 | 812 | 940 | 1418 | E |
| 85 | 844 | 907 | 1768 | 1016 |
| 84 | 924 | 939 | 940 | 1259 |
| 52 | 1003 | 1194 | 1275 | E |
| 26 | 844 | 1227 | 940 | 1127 |
| 25 | 828 | 1306 | 859 | 1179 |
| 82 | 828 | 908 | 1227 | E |
| 63 | 859 | 1067 | 908 | 1111 |
| 96 | 860 | 924 | 908 | 892 |
| 32 | 1051 | 924 | 1402 | 1068 |
| 91 | 891 | 940 | E | E |
| N | 24 | 24 | 23 | 20 |
| MEAN | 942 | 1050 | 1102 | 1193 |
| SD | 151 | 183 | 217 | 234 |
| MEDIAN | 867 | 964 | 1067 | 1163 |
| QRTILE | 79 | 112 | 144 | 123 |
| LOW | 796 | 844 | 812 | 892 |
| HIGH | 1322 | 1529 | 1768 | 1976 |

After these general parameters 1-10 have been set for all blocks, the user can specify the parameters to be set for each of the blocks individually (11-12 for the first block, 13-14 15 for the next block, etc.) in terms of the operation desired (that is, copy, add, or subtract), the number which is to be added or subtracted, and whether the same number should be presented for an arithmetic operation as that which was originally copied (i.e., same stimulus) or whether a different paired number should be presented such that the response will require entry of the same number as that originally copied (i.e., same response). If the user desires to have different operations occurring within a given block (for example, both addition and subtraction or copying and one or both of the arithmetic operations), the user may so specify and provide that the different operations should be presented in either alternate order or in random order within the block.

In the first embodiment described above, the cognitive speedometer requires the user both to copy data and then to perform at least one cognitive operation on different data and then enter the resultant data. Many users will find the simple copying of data to be boring, thereby discouraging their use of the cognitive speedometer. Accordingly, the present invention further encompasses a second embodiment of the cognitive speedometer wherein the simple copying of displayed data is unnecessary.

Figure 4:
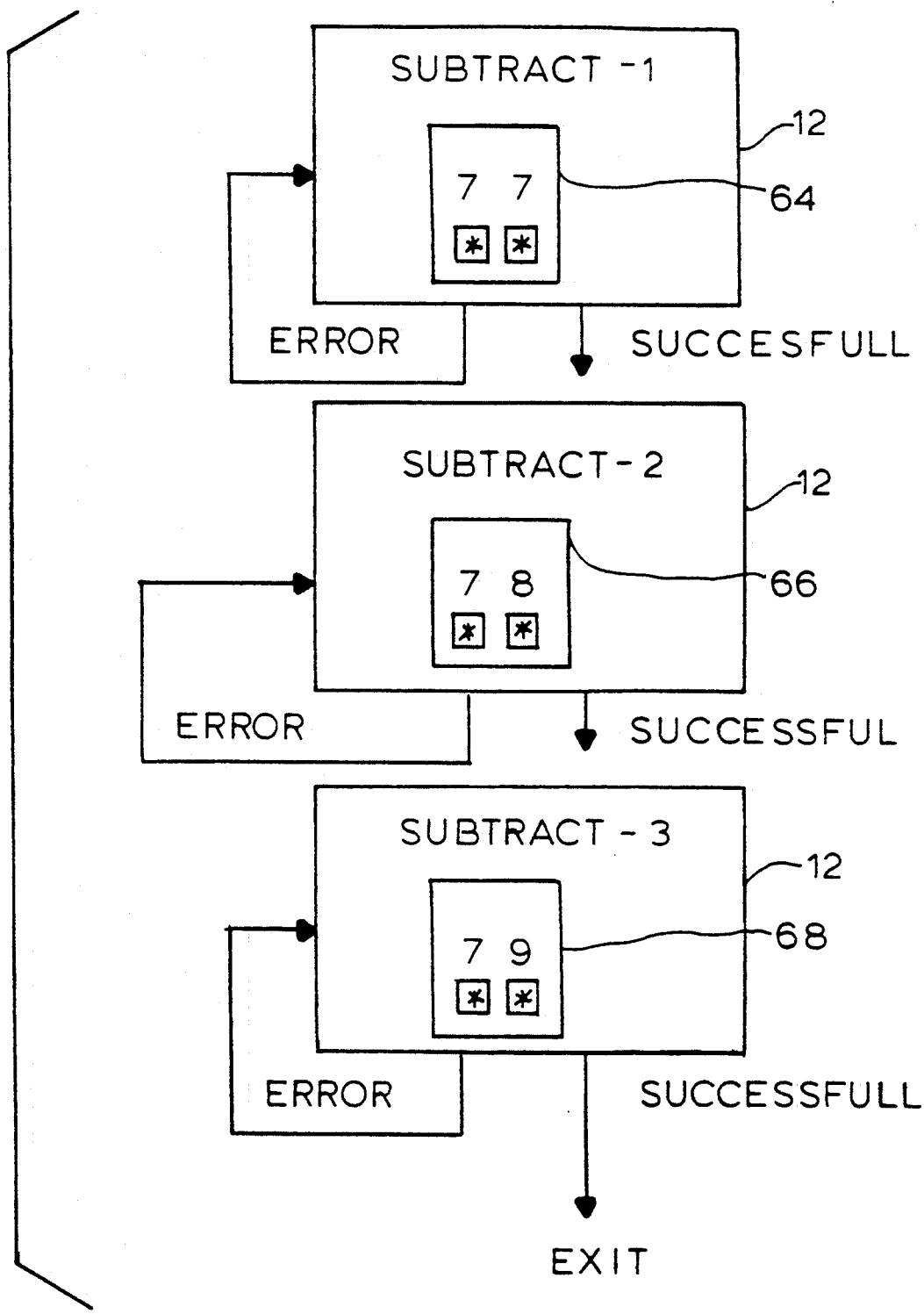
FIG. 4 is a flow chart for a second embodiment of the cognitive speedometer.

Referring now to FIG. 4, therein illustrated is a flow chart for a second preferred embodiment of the speed monitor program 55 which enables an assessment of the cognitive processing speed for a unit cognitive operation without requiring the user to simply copy data so that the copying latency may later be subtracted from the latency for a cognitive operation and physical entering of the resultant data. According to this second embodiment, data is generated (preferably randomly) and displayed on the screen 12, and the user is required to perform a plurality of tasks involving different numbers of cognitive operations thereon and then enter the resultant data on the response key set 14. For example, in the first block of trials the user may be required to subtract one from each number (trial) randomly generated and displayed in sequence on the screen 12, and then in the next block of trials to subtract two from each number, and in the next block of trials to subtract 3, etc. The numbers being generated and displayed on the screen 12 are preferably modified in each successive block so that the user should be entering on the response key set 14 the same numbers as the resultant data for each block (if he answers correctly). In order to preclude any role for memory in this operation, the sequence of the presentations (trials) may be altered from block to block, even though the exact same numbers will constitute the correct resultant data for the several trials within each full block. Thus, in one trial of the first block the user may be asked to subtract one from a number (77) shown in box 64, in a trial of the second block, to subtract 2 from a number (78) shown in box 66; and in a trial of the third block, to subtract 3 from the number (79) shown in box 68. Alternatively, the user may be asked to subtract (or add) different numbers or the numbers which he is asked to subtract (or add) may not be in sequence—that is, he may be asked to subtract 1 in block 1, 3 in block 2, 2 in block 3, etc.). Where incorrect resultant data is entered by the user on the response key set 14, the same trial may be presented later in the same block or a different one substituted therefor.

The microprocessor of the cognitive speedometer (whether software, firmware or hardware) then determines the time required for the user to perform the unit cognitive operation as the slope of a linear function associated with the set of points in X, Y coordinates. The Y coordinate is the variable associated with the time required for the user to perform the tasks and then enter the resultant data on the response key set 14, and X is the variable associated with the number of unit cognitive operations involved in the respective tasks. As earlier noted, the function has been shown by experimentation to be linear, with the required time increasing as the number of cognitive computations increases. The slope of the linear function provides a measure of the speed of such cognitive operations (e.g., computations), and the intercept provides a measure of the task latency without a cognitive operation (i.e., when the computation load is zero or a simple copying is involved).

The slope can be evaluated by assessing linearity and squaring the correlation between the computational loads and their latencies to determine how much of the variance is accounted for by the linear function. As a linear accounts function accounts for nearly all of the variance, the intercept of the Y axis indicates the copying latency, and the slope of the function indicates the computational latency (without the latency for entering the resultant data). In other words, the slope represents the time required for the user to perform the unit cognitive operation independently of the time required to physically enter the resultant data on the response key set 14. Only the tasks for which the user enters the correct resultant data on the response key set 14 are used in determining latency.

Figure 5:
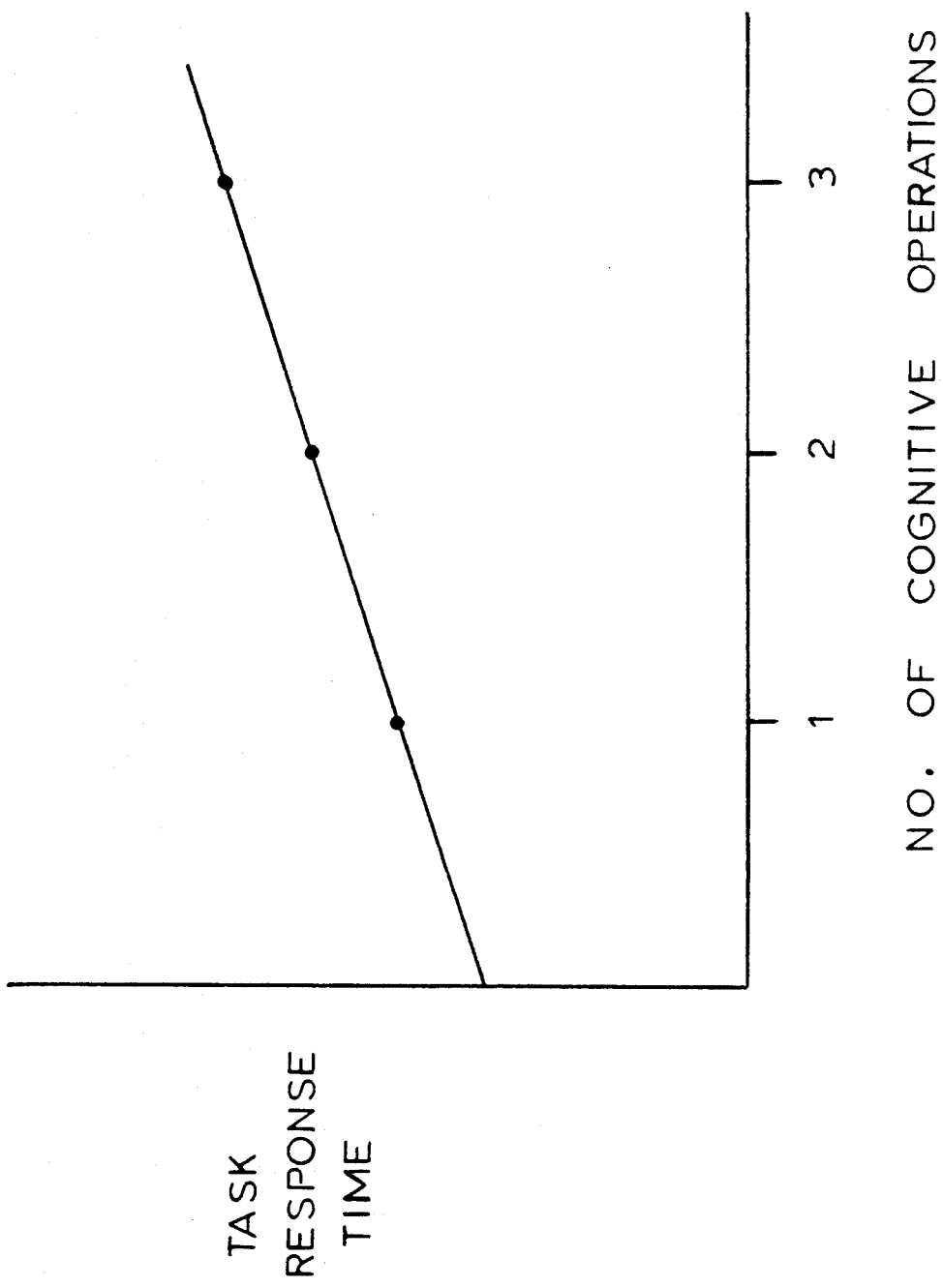
FIG. 5 is a graph of the task response time as a linear function of the number of cognitive operations.

The task response time is a linear function of the number of cognitive operations which must be formed by the user to complete the task, as indicated schematically in the graph of FIG. 5. While the cognitive speedometer may be adapted to provide a graphic output, generally it will simply perform the necessary calculations to determine the slope of the linear function. Since it is expected that the various data points will lie on or closely adjacent a straight line, techniques well known to those in the statistical arts may be employed to ignore or discount one or more particular data points which are at variance with the linear function established by the majority of the data points. Thus the second embodiment of the present invention not only avoids the necessity of the user doing straight "copy" work, but also lends itself to statistical techniques for detecting errant data points. While the aforementioned statistical techniques require that a substantial number of data points be taken (that is, that the user perform a plurality of tasks involving a substantial plurality of different numbers of cognitive operations on the data), where such statistical techniques are not being employed a single pair of data points (for example, adding 1 to a set of data as the first cognitive operation, and adding 2 to a set of data as the second cognitive operation) may suffice to indicate the slope of the linear function although it is recommended that at least three data points be used to confirm linearity of the function.

While it is possible to determine the appropriate data point in the first or second embodiments using the means or averages of the response times for each block, the median response times are preferred to reduce the outliner effect (that is, the disproportionate effect of an extremely slow response time on the mean response time). It appears preliminarily that the mean of a plurality of the fastest response times or the lower hinge of the distribution of response times affords a response time measure which is comparable to the median response time and further reduces the outlier effect.

Figure 6:
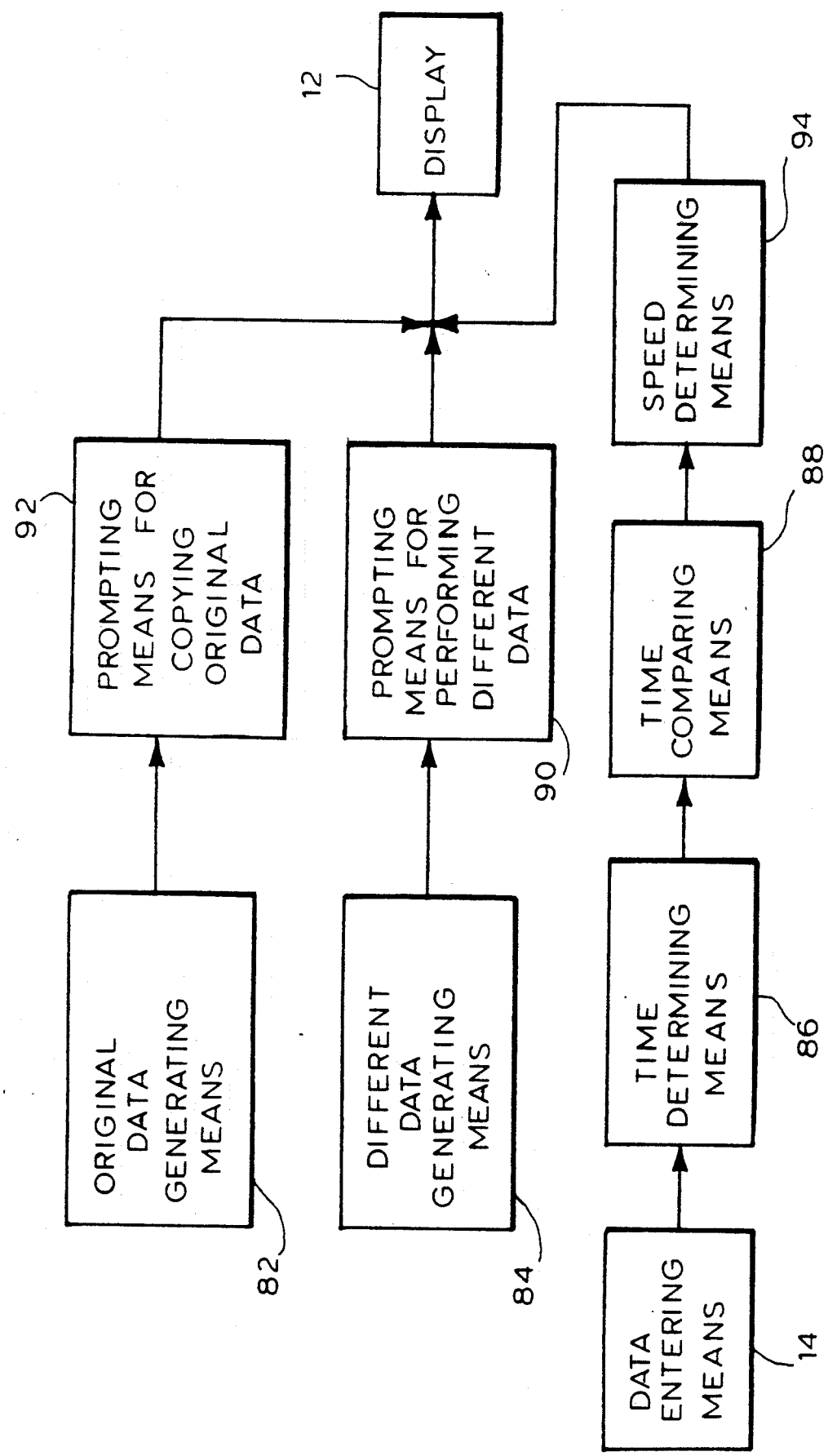
FIG. 6 is a block diagram of the cognitive speedometer according to the present invention.

Referring to FIG. 6, when the cognometer 10 is operating under the control of the speed monitor program 55, it includes or functions as if it included the following functional elements: means 82 for generating original data and displaying the same on the display means, means 84 for generating and displaying on the display means different data, means 86 for determining the time required for the user to perform a unit cognitive operation, means 88 for comparing the time required for the user to perform the unit cognitive operation with an established norm for the time required to perform the unit cognitive operation, prompting means 90 for indicating on the display means at an appropriate time the unit cognitive operation to be performed by the user on the displayed different data, prompting means 92 for displaying on the display means at an appropriate time instructions for the user to copy the displayed original data, and means 94 for determining the user's speed of cognitive processing per unit of time.

To summarize, the present invention provides a reliable, rapid and automatic administration, scoring, and reporting test for self-testing at home or elsewhere. The testing is appropriate and effectively isolates the cognitive ability to be tested, even in aged or infirm users. Testing, scoring, and reporting of results, on screen or by optional printout on paper tape, are fully automatic so that the monitor can be used for self-testing by the general public and for testing patients at home, as well as for testing by physicians, nurses or other professionals. Each monitor requires only a few moments and is easily repeated at any time by automatic generation of new random numbers. The "speed" monitor assesses the cognitive processing speed in performing a cognitive operation without reflecting physical ability, and preferably tests the cognitive processing speed in performing a unit or single cognitive operation.

Now that the preferred embodiments of the present invention have been shown and described, various modifications and improvements thereon will become readily apparent to those skilled in the art. Accordingly, the spirit and scope of the present invention is to be limited only by the appended claims, and not by the foregoing specification.

```
DECLARE SUB Ttest (TimeArray!(), StartTRCalc, Trials%, Block1!, Block2!,
    score!, Corr!, BlFormat(), NoShow$(), Distracted$())
'DECLARE SUB STEMANDLEAF (BL!, ActualNum!, RankArray!(), inter$, UHINGE,
    LHINGE, MEDIAN)
DECLARE SUB GIVEMECAPSANDNUM ()
DECLARE SUB givemesubjectstory (DRIVE$, EDIT.IT$, Subject.Lastname$,
    Subject.Firstname$, subject.id$, subject.age$, subject.sex$, subject.date$,
    subject.study$, subject.studyname$)
DECLARE SUB GETTIMER (TIMEDRIVE$, Td1!, Td2!, NoTimer$)
DECLARE SUB BOX (T!, L!, R!, B!)
DECLARE SUB CLEARKEYBOARD ()
DECLARE SUB STANDARDDEV (N!, SUM!, SS!, SD!)
DECLARE SUB HEADING ()
'DECLARE SUB MEDIAN (N!, MED!, LW!, HH!, QUARTILE!, P25!, P75!)
DECLARE SUB MINUSVAL (MED(), Block%)
DECLARE SUB PURERAND (BL, BlFormat(), DIGSIZE, LOWVAL, HIGHVAL, Block%,
    Trials%, STIM(), ANSWER(), RANDOMT())
DECLARE SUB SHOWVALUES (ESCAPE$, BADRUN$, SHOWRES$, KEYHIT$, Trials%, Block%,
    BlFormat(), NoShow$(), MED(), ALTMED(), NUMCORRECT(), NUMALTCORRECT(),
SHOWCOMP$, NumCon, NumCon$, Contrast(), CONNAMES$(), CON1$, CON2$, COPYCUT,
    SUBCUT, DIFFCUT, COMPTYPE$, COPTR, SUBTR, DIFFTR, MAXREC, PassPercent,
    PassRun$, StartTRCalc, Distracted$())
DECLARE SUB BYMEAN (Block, StartTRCalc, RankArray(), AR(), N!, MEAN!, SD!,
    MED!, BiMean!, Mad!, LHINGE!, UHINGE!, SemiQRTle!, LO!, HI!)
DECLARE SUB PARAMSPD (Block, StartTRCalc, MAXBLOCKS, MAXTRIALS, Td2, NEWID$,
    EDIT.IT$, PARA$, PARAF$, PDRIVE$, DIGSIZE, MODE$, MID, DIV, MODESET,
    Block$, Block%, Trials%, TYPEBLOCK$, TBORDER$, TYPEISI$, ISI$, ISI, KISI$,
    KISI, SHOWRES$, SHOWCOMP$, NumCon, Contrast(), CONNAMES$(), BlFormat(),
```

```
    NoShow$(), Trials$, OP$, NOSH$, VALUE$, SAMP$, NumCon$, CON1$, CON2$, CO,
    SAVEPF$, OUTPF$, POUTDRIVE$, BL, Distracted$(), STARTTR$, Distract$,
    DisFlash$)
DECLARE SUB PRESTIM (ESCAPE$, DIV, MID, MODESET, NG$, TRALS%, Trials%, CLUE$,
    REALCLUE$, Block%, BL, BlFormat(), NoShow$(), RANDOMT(), TYPEISI$, ISI,
    GiveSound$, ASTPROMPT, ScreenSynch, STIM(), ANSWER(), K1$, K2$, CHOICE(),
    DIGSIZE, TimeArray(), ER(), ERTIME(), MISTAKE(), Td1, Td2, PassPercent,
    PassRun$, Subject.Lastname$, Subject.Firstname$, Distracted$(),
    NumDistract, AllFlash$, ErrorBeep$)

CLEAR , , 3000
HOMEDRIVE$ = "C:": TIMEDRIVE$ = "C:": ScreenFresh$ = "Y": OLDDRIVE$ = "C:"
COPYCUT = 20000: SUBCUT = 20000: DIFFCUT = 20000
PassPercent = 80: ' will flash if percent correct is less than. to disable
    set to -1
MAXBLOCKS = 8
MAXTRIALS = 96
StartTRCalc = 1
NumDistract = 4
AllFlash$ = "Y": 'set to N if you want only 1 of 4 to flash
RANDOMIZE TIMER
NoShow$ = "Y": ' Do not show type of operation on alternating block
               ' FKEY 1 allows you to switch on and off
GiveSound$ = "Y"
NoTimer$ = "Y"
PassRun$ = "Y"
Badrun$ = "N"
ESCAPE$ = "N"

DIM BlFormat(MAXBLOCKS, 5), CHOICE(MAXBLOCKS, MAXTRIALS), ARADD(MAXTRIALS),
    ARSUB(MAXTRIALS)
DIM ANSWER(MAXBLOCKS, MAXTRIALS), MIN(MAXBLOCKS, MAXBLOCKS, 2),
    RANDOMT(MAXBLOCKS, MAXTRIALS)
DIM STIM(MAXBLOCKS, MAXTRIALS), DS(41), NoShow$(MAXBLOCKS)
DIM TimeArray(MAXBLOCKS, MAXTRIALS), PERCENTILE(MAXBLOCKS, 2)
DIM ER(MAXTRIALS), ERTIME(MAXBLOCKS, MAXTRIALS), MISTAKE(MAXTRIALS, 2),
    CHEK(MAXTRIALS)
DIM Meanright(MAXBLOCKS), MEANWRONG(MAXBLOCKS), STANDRIGHT(MAXBLOCKS),
    STANDWRONG(MAXBLOCKS)
DIM MeanALTright(MAXBLOCKS * 2), STANDALTRIGHT(MAXBLOCKS * 2),
    ALTMED(MAXBLOCKS * 2), ALTLO(MAXBLOCKS * 2), ALTHI(MAXBLOCKS * 2)
DIM NUMALTCORRECT(MAXBLOCKS * 2), ALTQUART(MAXBLOCKS * 2)
DIM MED(MAXBLOCKS), LO(MAXBLOCKS), HI(MAXBLOCKS), AR(MAXTRIALS),
    NUMCORRECT(MAXBLOCKS), QUART(MAXBLOCKS)
DIM Contrast(MAXBLOCKS, 2), CONNAME$(MAXBLOCKS)
DIM BWM(MAXBLOCKS), ALTBWM(MAXBLOCKS * 2), ALTPERCENT(MAXBLOCKS * 2, 2)
DIM RankArray(MAXBLOCKS, MAXTRIALS), COPRT(100), SUBRT(100), DIFFRT(100)
DIM Distracted$(MAXBLOCKS, 2)

ON ERROR GOTO Trouble
CLS
CALL GETTIMER(TIMEDRIVE$, Td1, Td2, NoTimer$)
    'IF NOTIMER$ = "Y" THEN GOSUB 9010: REM INPUT"RETURNED FROM TIMER";XXX$
    'IF NOTIMER$ = "Y" THEN GOSUB MAKETIME: REM INPUT"RETURNED FROM TIMER";XXX$ ASTPROMPT = 600 / Td2: 'ASTERISK PROMPT IS ON FOR 500 MSECS
Trials% = 48: GOSUB RANDOMALT
'''GOSUB GETSUBJECTFILE: 'OLD 57
    ' Next Three Lines added to deal with occasional computer board which does
    ' not use the save vertical synch pulse
    ' 20 is more than enough attempts. The AST uses 1 or 2 at most
    ScreenLoop = 0
'ScreenSynch = 8: WHILE ScreenSynch = 8 AND ScreenLoop <= 20: ScreenSynch =
    INP(986) AND 8: ScreenLoop = ScreenLoop + 1: WEND
ScreenSynch1: ScreenSynch = INP(986) AND 8: IF ScreenSynch = 8 AND ScreenLoop
    <= 20 THEN ScreenLoop = ScreenLoop + 1: GOTO ScreenSynch1
    IF ScreenLoop >= 20 THEN ScreenFresh$ = "N"

ON KEY(1) GOSUB ErrorToggle
ErrorBeep$ = "N"
```

```
ON KEY(2) GOSUB soundtoggle
CALL GIVEMECAPSANDNUM
BEGINRUN: CALL HEADING
GOSUB GETSUBJECTFILE
TOPOFRUN:
'GOSUB STARTPARAMS: CLS
RESTART: CALL PARAMSPD(Block, StartTRCalc, MAXBLOCKS, MAXTRIALS, Td2, NEWID$,
EDIT.IT$, PARA$, PARAF$, PDRIVE$, DIGSIZE, MODE$, MID, DIV, MODESET, Block$,
Block%, Trials%, TYPEBLOCK$, TBORDER$, TYPEISI$, ISI$, ISI, KISI$, KISI,
SHOWRES$, SHOWCOMP$, NumCon, Contrast(), CONNAME$(), BlFormat(), NoShow$(),
Trials$, OP$, NOSH$, VALUE$, SAMP$, NumCon, CON1$, CON2$, CO, SAVEPF$,
OUTPF$, POUTDRIVE$, BL, Distracted$(), STARTTR$, Distract$, DisFlash$)
CLS

GOSUB GETSUBJECTFILE

NEWRUN:
CLS : 'PRINT MODESET; ","; MODESET$; : INPUT GG$
IF MODESET = 40 THEN MID = 20: DIV = 2 ELSE MID = 40: DIV = 1
IF TYPEBLOCK$ = "1" THEN CALL PURERAND(BL, BlFormat(), DIGSIZE, LOWVAL,
HIGHVAL, Block%, Trials%, STIM(), ANSWER(), RANDOMT())
IF TYPEBLOCK$ = "2" THEN GOSUB FIXEDSTIMULI
IF MODESET = 40 THEN SHELL "MODE 40"
KEY(1) ON
KEY(2) ON
'GOSUB PRESENTSTIMULI
CALL PRESTIM(ESCAPE$, DIV, MID, MODESET, NG$, TRALS%, Trials%, CLUE$,
REALCLUE$, Block%, BL, BlFormat(), NoShow$(), RANDOMT(), TYPEISI$, ISI,
GiveSound$, ASTPROMPT, ScreenSynch, STIM(), ANSWER(), K1$, K2$, CHOICE(),
DIGSIZE, TimeArray(), ER(), _ ERTIME(), MISTAKE(), Td1, Td2, PassPercent,
PassRun$, Subject.Lastname$, Subject.Firstname$, Distracted$(), NumDistract,
AllFlash$, ErrorBeep$)
KEY(1) OFF: KEY(2) OFF: LOCATE , , 0
SHELL "MODE 80": LOCATE , , 0: MID = 40
GOSUB DISKSAVE
IF Block% = 2 AND ((BlFormat(1, 1) = 2 AND BlFormat(2, 1) = 3) OR
(BlFormat(1, 1) = 3 AND BlFormat(2, 1) = 2)) THEN GOSUB GETSUMS
IF PassRun$ = "Y" THEN CALL SHOWVALUES(ESCAPE$, BADRUN$, SHOWRES$, KEYHIT$,
Trials%, Block%, BlFormat(), NoShow$(), MED(), ALTMED(), NUMCORRECT(),
NUMALTCORRECT(), SHOWCOMP$, NumCon, NumCon$, Contrast(), CONNAME$(), CON1$,
CON2$, COPYCUT, SUBCUT, _ DIFFCUT, COMPTYPE$, COPTR, SUBTR, DIFFTR, MAXREC,
PassPercent, PassRun$, StartTRCalc, Distracted$())
GOSUB REVISEDMENU
END GETSUBJECTFILE:
 ON ERROR GOTO filenothere
 foundsubjectfile$ = "N"
'OPEN HOMEDRIVE$ + "SUBINFO.ID" FOR INPUT AS #1
  INPUT #1, Subject.Lastname$, Subject.Firstname$, subject.id$, subject.age$,
subject.sex$, subject.date$, subject.study$, subject.studyname$
 CLOSE #1
 foundsubjectfile$ = "Y"
 OUTFIL$ = LEFT$(Subject.Firstname$, 1)
 OUTFIL$ = OUTFIL$ + LEFT$(Subject.Lastname$, 1)
 OUTFIL$ = OUTFIL$ + LEFT$(subject.id$, 4)
FILENOTFOUND: 'just return from
RETURN
'filenothere: CLOSE #1: CLS : LOCATE 12, 20: INPUT " NO SUBJECT ID FILE-
<RET> MAIN MENU "; GARB$: CLS : RUN "C:MENUDX": END
filenothere: CLOSE #1: CLS : foundsubjectfile$ = "N": EDIT.IT$ = "M": CALL
givemesubjectstory(DRIVE$, EDIT.IT$, Subject.Lastname$, Subject.Firstname$,
subject.id$, subject.age$, subject.sex$, subject.date$, subject.study$,
subject.studyname$): _ RESUME RESTART: ' STARTPARAMS: 'GOSUB GETSUBJECTFIL 'CHECKRANDSTIM:
 'YES = 0
 'FOR X = 1 TO TR
 'IF STIM(B, X) = N% THEN YES = 1
```

```
'NEXT X
'IF DIGSIZE = 1 AND YES = 1 THEN IF N% <> STIM(B, TR - 1) OR X = TR THEN YES
= 0
'RETURN

FIXEDSTIMULI:   IF DIGSIZE = 1 THEN LOWVAL = 1: HIGHVAL = 9 ELSE LOWVAL = 21:
HIGHVAL = 99
  ADDIT$ = "N": SUBTR$ = "N": MAXSUB = 0: MAXADD = 0: OldNum = 0
  FOR BL = 1 TO Block%
    IF BlFormat(BL, 1) = 2 THEN SUBTR$ = "Y": IF MAXSUB < BlFormat(BL, 2) THEN
MAXSUB = BlFormat(BL, 2)
    IF BlFormat(BL, 1) = 1 THEN ADDIT$ = "Y": IF MAXADD < BlFormat(BL, 2) THEN
MAXADD = BlFormat(BL, 2)
  NEXT BL
  LOWVALINC = 0
  IF BlFormat(1, 3) = 1 AND DIGSIZE = 1 THEN LOWVALINC = BlFormat(1, 2)
  IF BlFormat(2, 3) = 1 AND DIGSIZE = 1 THEN LOWVALINC = BlFormat(2, 2)
  IF SUBTR$ = "Y" AND ADDIT$ = "N" AND DIGSIZE = 1 THEN LOWVAL = 1 +
LOWVALINC: HIGHVAL = 9 - MAXSUB
  IF SUBTR$ = "N" AND ADDIT$ = "Y" AND DIGSIZE = 1 THEN LOWVAL = 1 + MAXADD:
HIGHVAL = 9
  IF SUBTR$ = "Y" AND ADDIT$ = "Y" AND DIGSIZE = 1 THEN LOWVAL = 1 + MAXADD:
HIGHVAL = 9 - MAXSUB
  'PRINT SUBTR$; ","; ADDIT$; ","; LOWVAL; ","; HIGHVAL; : INPUT GG$
  FOR TR = 1 TO Trials%
GETRANDNUM:
N% = INT((HIGHVAL - LOWVAL + 1) * RND + LOWVAL)
'IF INT(N% / 10) = INT(OldNum / 10) THEN GOTO GETRANDNUM
IF DIGSIZE = 2 AND INT(N% / 10) = INT(OldNum / 10) THEN GOTO GETRANDNUM
IF N% MOD 10 = 0 THEN GOTO GETRANDNUM: 'NO ZEROS SEE PURELYRANDOM
'IF BLFORMAT(B, 1) = 4 THEN IF (N% + BLFORMAT(B, 2)) MOD 10 = 0 THEN GOTO
GETRANDNUM
'IF BLFORMAT(B, 1) = 4 THEN IF (N% + BLFORMAT(B, 2)) MOD 10 < N% MOD 10 THEN
GOTO GETRANDNUM: 'FOR DX-3 VERSION
IF N% MOD 11 = 0 THEN GOTO GETRANDNUM: 'WILL NOT ALLOW 33,44 ETC. 'CURRENTLY
DISABLED
IF DIGSIZE = 1 THEN GOTO JUMPOVERCHECK: ' NOTE THAT LINES ABOVE SHOULD
CONTROL VALUES
IF (N% + 1) MOD 10 = 0 THEN GOTO GETRANDNUM
OldNum = N%
IF SUBTR$ = "Y" THEN IF (N% + MAXSUB) MOD 10 = 0 THEN GOTO GETRANDNUM: ' FOR
DX-3 VERSION
IF SUBTR$ = "Y" THEN IF (N% + MAXSUB) MOD 10 < N% MOD 10 THEN GOTO
GETRANDNUM: 'FOR DX-3 VERSION
IF ADDIT$ = "Y" THEN IF (N% - MAXADD) MOD 10 = 0 THEN GOTO GETRANDNUM: ' FOR
DX-3 VERSION
IF ADDIT$ = "Y" THEN IF (N% - MAXADD) MOD 10 > N% MOD 10 THEN GOTO
GETRANDNUM: 'FOR DX-3 VERSION

JUMPOVERCHECK: 'LOCATE 23, 40: PRINT TR; "["; N%; : INPUT XX$

GOSUB CHECKSTIM
IF YES = 0 THEN STIM(0, TR) = N%: ANSWER(0, TR) = N%: GOTO BIPASS
GOTO GETRANDNUM
BIPASS: REM

NEXT TR
BlFormat(0, 1) = 0
FOR B = 1 TO Block%
  IF BlFormat(B, 1) = 5 THEN GOSUB RANDOMALT
  FOR T = 1 TO Trials%
    IF ((BlFormat(B, 1) = 1) AND (BlFormat(B, 3) = 1)) THEN STIM(B, T) =
STIM(0, T): ANSWER(B, T) = STIM(B, T) + BlFormat(B, 2)
    IF ((BlFormat(B, 1) = 1) AND (BlFormat(B, 3) = 2)) THEN STIM(B, T) =
STIM(0, T) - BlFormat(B, 2): ANSWER(B, T) = STIM(0, T)
    IF ((BlFormat(B, 1) = 2) AND (BlFormat(B, 3) = 1)) THEN STIM(B, T) =
STIM(0, T): ANSWER(B, T) = STIM(B, T) - BlFormat(B, 2)
    IF ((BlFormat(B, 1) = 2) AND (BlFormat(B, 3) = 2)) THEN STIM(B, T) =
STIM(0, T) + BlFormat(B, 2): ANSWER(B, T) = STIM(0, T)
      'IF B = BLOCK% THEN IF ((BLFORMAT(B, 1) = 2) AND (BLFORMAT(B, 3) = 1))
```

```
      THEN STIM(B, T) = STIM(0, T): ANSWER(B, T) = STIM(B, T) - BLFORMAT(B, 2)
        IF ((BlFormat(B, 1) = 4) AND (BlFormat(B, 3) = 2)) THEN IF T MOD 2 = 0
  THEN STIM(B, T) = STIM(0, T) + BlFormat(B, 2): ANSWER(B, T) = STIM(0, T) ELSE
  STIM(B, T) = STIM(0, T): ANSWER(B, T) = STIM(0, T): 'ALTERNATION SERIES
        IF ((BlFormat(B, 1) = 5) AND (BlFormat(B, 3) = 2)) THEN IF RANDOMT(B, T) =
  0 THEN STIM(B, T) = STIM(0, T) + BlFormat(B, 2): ANSWER(B, T) = STIM(0, T)
  ELSE STIM(B, T) = STIM(0, T): ANSWER(B, T) = STIM(0, T): 'ALTERNATION SERIES
       IF BlFormat(B, 1) = 3 THEN STIM(B, T) = STIM(0, T): ANSWER(B, T) = STIM(0,
  T): REM STRAIGHT COPY
     NEXT T
   NEXT B
     IF TBORDER$ = "2" THEN GOSUB MIXFIX
     'FOR B = 1 TO BLOCK%: FOR TR = 1 TO TRIALS%: PRINT STIM(B, TR); ",";
     ANSWER(B, TR); ":"; : NEXT TR: PRINT : NEXT B: INPUT gg$
     'FOR TR=1 TO TRIALS%:PRINT ANSWER(B,TR);",";:NEXT TR:PRINT:NEXT B:INPUT XX$
   RETURN MIXFIX: 'WILL RANDOMIZE FIXED FIRST BLOCK OVER SUBSEQUENT BLOCKS
    FOR B = 1 TO Block%
    FOR T = 1 TO Trials%
  GETN: N% = (RND(1) * Trials%) + 1
     IF BlFormat(B, 1) = 4 AND T MOD 2 = 0 AND N% MOD 2 <> 0 THEN GOTO GETN
     IF BlFormat(B, 1) = 4 AND T MOD 2 <> 0 AND N% MOD 2 = 0 THEN GOTO GETN
       CHEK(T) = N%
    NEXT T
    GOSUB SORTIT
   NEXT B
  RETURN SORTIT:
   FOR A1 = 1 TO Trials% - 1
    FOR A2 = A1 TO Trials%
      IF CHEK(A1) > CHEK(A2) THEN SWAP A1, A2: SWAP STIM(B, A1), STIM(B, A2):
  SWAP ANSWER(B, A1), ANSWER(B, A2): SWAP RANDOMT(B, A1), RANDOMT(B, A2)
    NEXT A2
   NEXT A1
  RETURN

CHECKSTIM:
    YES = 0
    FOR X = 1 TO TR
    IF STIM(0, X) = N% THEN YES = 1

NEXT X
    IF DIGSIZE = 1 AND YES = 1 THEN IF N% <> STIM(0, TR - 1) OR X = TR THEN YES
  = 0
  RETURN

NEWERPRINT:
    ERRFLAG = 4: ON ERROR GOTO Trouble
    TIT$ = "BUSCHKE COGNOMETER COGNITIVE SPEEDOMETER"
    PRINT #1, SPC(40 - CINT(LEN(TIT$) / 2)); TIT$
    PRINT #1, SPC(37); "Page 2 "
    PRINT #1, " ": PRINT #1, " "
    '*PRINT #1, "NAME   : "; SUBJECT.LASTNAME$; ", "; SUBJECT.FIRSTNAME$
    PRINT #1, "NAME   : "; Subject.Lastname$; ", "; Subject.Firstname$; : PRINT
  #1, SPC(30 - ((LEN(Subject.Lastname$)) + (LEN(Subject.Firstname$)))); " DATA
  FILE : "; OUTFIL$ + ".SF"
    'PRINT #1, "ID     : "; SUBJECT.ID$
    PRINT #1, "ID     : "; subject.id$; : IF LEN(PARAF$) < 1 THEN PRINT #1, "":
  ELSE PRINT #1, SPC(30 - LEN(subject.id)); "    PARAMETER FILE : "; PARAF$ +
  ".SPA"
    PRINT #1, "AGE    : "; subject.age$
    PRINT #1, "SEX    : "; subject.sex$
    'PRINT #1, ""
    PRINT #1, "STUDY : "; subject.studyname$
    PRINT #1, ""
    PRINT #1, "DATE   : "; DATE$
    PRINT #1, "TIME   : "; TIME$
```

```
PRINT #1, " "
PRINT #1, "NUMBER OF BLOCKS ="; Block%
PRINT #1, "NUMBER OF TRIALS ="; Trials%
IF StartTRCalc > 1 THEN PRINT #1, "FIRST TRIAL FOR STATISTICS =";
StartTRCalc
IF Block% <> 1 AND TBORDER$ = "1" THEN PRINT #1, "SAME STIMULUS ORDER ACROSS
BLOCKS"
IF Block% <> 1 AND TBORDER$ = "2" THEN PRINT #1, "RANDOMIZED PRESENTATION
ACROSS BLOCKS"
IF TYPEISI$ = "1" THEN PRINT #1, "FIXED INTERVAL OF "; ISI$; " SECONDS"
IF TYPEISI$ = "2" THEN PRINT #1, "SELF-PACED WITH A "; KISI$; " DELAY AFTER
A KEYPRESS"
PRINT #1, " "
 'PRINT #1, STRING$(80, "_")
 PRINT #1, STRING$(80, "-")
PRINT #1, " "
PRINT #1, "        ";
FOR A1 = 1 TO Block%
  IF ((BlFormat(A1, 1) = 0) OR (BlFormat(A1, 1) = 3)) THEN PRINT #1, "  C";
  IF BlFormat(A1, 1) = 4 THEN PRINT #1, "  ALT";
  IF BlFormat(A1, 1) = 5 THEN PRINT #1, "  RND";
  IF BlFormat(A1, 1) = 4 THEN IF NoShow$(A1) = "Y" THEN PRINT #1, "N";
  IF BlFormat(A1, 1) = 4 THEN IF NoShow$(A1) = "N" THEN PRINT #1, "C";
  IF BlFormat(A1, 1) = 4 THEN IF NoShow$(A1) = "R" THEN PRINT #1, "R";
  IF BlFormat(A1, 1) = 4 THEN PRINT #1, USING "#"; BlFormat(A1, 2);
  IF BlFormat(A1, 1) = 5 THEN IF NoShow$(A1) = "N" THEN PRINT #1, "C";
  IF BlFormat(A1, 1) = 5 THEN IF NoShow$(A1) = "R" THEN PRINT #1, "R";
  IF BlFormat(A1, 1) = 5 THEN PRINT #1, USING "#"; BlFormat(A1, 2);
  IF BlFormat(A1, 1) = 1 THEN PRINT #1, "     +"; : PRINT #1, USING "#";
BlFormat(A1, 2);
  IF BlFormat(A1, 1) = 2 THEN PRINT #1, "     -"; : PRINT #1, USING "#";
BlFormat(A1, 2);
NEXT A1
PRINT #1, " ": 'PRINT #1, " "
PRINT #1, "        ";
FOR A1 = 1 TO Block%
  IF Distracted$(A1, 1) = "Y" AND Distracted$(A1, 2) = "Y" THEN PRINT #1, "  FL(D)";
  IF Distracted$(A1, 1) = "Y" AND Distracted$(A1, 2) = "N" THEN PRINT #1, "   (D)";
  IF Distracted$(A1, 1) = "N" AND Distracted$(A1, 2) = "N" THEN PRINT #1, "      ";
NEXT A1
PRINT #1, " ": PRINT #1, " "
PRINT #1, SPC(4); " #";
FOR A1 = 1 TO Block%: PRINT #1, USING "######"; A1;
REM PRINT #1,SPC(2);
NEXT A1
PRINT #1, " "
'PRINT #1, STRING$(8 * BLOCK% + 8, "-")
PRINT #1, STRING$(80, "-")
PRINT #1, " "
FOR T = 1 TO Trials%
  PRINT #1, USING "##"; T;
  PRINT #1, SPC(2);
  'PRINT #1,USING "###";STIM(B,T);
  FOR B = 1 TO Block%
    IF B = 1 THEN PRINT #1, USING "###"; STIM(B, T);
    'IF B < block% AND T > TRIALS% / 2 THEN PRINT #1, "      "; : GOTO BYBY
    IF TimeArray(B, T) > 0 THEN PRINT #1, USING "######"; TimeArray(B, T);
    ELSE PRINT #1, "     E";
BYBY:
  NEXT B
  PRINT #1, " "
NEXT T
'PRINT #1, STRING$(80, "_")
PRINT #1, STRING$(80, "-")
'PRINT #1, SPC(30); "       ALTERNATION BLOCK BREAKDOWN     "
'PRINT #1, SPC(30); " Copy    Sub   Copy1  Copy2  Sub1   Sub2"
FOR B = 1 TO Block%
```

```
    FOR T = StartTRCalc TO Trials% / 1: ' IN DX / 2 ONLY FIRST TWENTY TRIALS OF
EACH BLOCK
    IF TimeArray(B, T) <= 0 THEN GOTO SKPIT
    NRIGHT = NRIGHT + 1
    SUMRIGHT = SUMRIGHT + TimeArray(B, T)
    SUMSQ1 = SUMSQ1 + (TimeArray(B, T) * TimeArray(B, T))
SKPIT:   'VALUE NOT INCLUDED SINCE ERROR SCORE
    NEXT T
    FOR BADT = 1 TO ER(B)
     SUMWRONG = SUMWRONG + ERTIME(B, BADT)
     SUMSQ2 = SUMSQ2 + (ERTIME(B, BADT) * ERTIME(B, BADT))
    NEXT BADT
    IF NRIGHT > 0 THEN Meanright(B) = CINT(SUMRIGHT / NRIGHT) ELSE Meanright(B)
= 0
    NUMCORRECT(B) = NRIGHT
    IF ER(B) > 0 THEN MEANWRONG(B) = CINT(SUMWRONG / ER(B))
    NUMT = Trials% - StartTRCalc + 1
    CALL STANDARDDEV(NRIGHT, SUMRIGHT, SUMSQ1, SD)
    STANDRIGHT(B) = SD
    CALL STANDARDDEV(ER(B), SUMWRONG, SUMSQ2, SD)
    STANDWRONG(B) = SD
    FOR X = 1 TO Trials% / 1
     IF TimeArray(B, X) > 0 THEN C = C + 1: AR(C) = TimeArray(B, X)
    NEXT X
    'CALL MEDIAN(C, MED1, LO1, HI1, QUARTILE, P25, P75)
    CALL BYMEAN(B, StartTRCalc, RankArray(), AR(), C, MEAN, SD, MED1, BiMean,
Mad, P25, P75, QUARTILE, LO1, HI1)
    LO(B) = LO1: HI(B) = HI1
    MED(B) = MED1: QUART(B) = QUARTILE: BWM(B) = BiMean
SUMRIGHT = 0: SUMWRONG = 0: SUMSQ1 = 0: SUMSQ2 = 0: NRIGHT = 0: C = 0
NEXT B
 PRINT #1, " ": 'PRINT #1, " "
  PRINT #1, "CORRECT";
  FOR B = 1 TO Block% + 0
   PRINT #1, USING "######"; NUMCORRECT(B);
   IF INT((NUMCORRECT(B) / Trials%) * 100) < PassPercent THEN PassRun$ = "N"
  NEXT B
  PRINT #1, " "
  PRINT #1, " "
  PRINT #1, "MEAN   ";
  FOR B = 1 TO Block% + 0
   PRINT #1, USING "######"; Meanright(B);
  NEXT B
  PRINT #1, " ": PRINT #1, "SD     ";
  FOR B = 1 TO Block% + 0
   PRINT #1, USING "######"; STANDRIGHT(B);
  NEXT B
  PRINT #1, " "

IF (BWM(B)) <= 0 THEN GOTO SKIPBWM
  PRINT #1, " ": PRINT #1, "BIMEAN ";
  FOR B = 1 TO Block% + 0
   PRINT #1, USING "######"; BWM(B);
  NEXT B
  PRINT #1, " "
SKIPBWM: IF OUTOF$ = "1" THEN COLOR 0, 7: LOCATE 22, 22: INPUT " PRESS RETURN
TO CONTINUE "; GARB$: CLS : COLOR 7, 0
  'PRINT #1, STRING$(8 * BLOCK% + 8, "_")
  PRINT #1, STRING$(80, "-")
  PRINT #1, " ": PRINT #1, "MED    ";
  FOR B = 1 TO Block% + 0
   PRINT #1, USING "######"; MED(B);
  NEXT B
  PRINT #1, " ": PRINT #1, "SINTQRT";
  FOR B = 1 TO Block% + 0
   PRINT #1, USING "######"; QUART(B);
  NEXT B
  PRINT #1, " ": PRINT #1, "LOW    ";
  FOR B = 1 TO Block% + 0
   PRINT #1, USING "######"; LO(B);
```

```
NEXT B
PRINT #1, " ": PRINT #1, " 25%ile";
FOR B = 1 TO Block% + 0
 PRINT #1, USING "######"; PERCENTILE(B, 1);
NEXT B
PRINT #1, " ": PRINT #1, " 75%ile";
FOR B = 1 TO Block% + 0
 PRINT #1, USING "######"; PERCENTILE(B, 2);
NEXT B
PRINT #1, " ": PRINT #1, "HIGH    ";
FOR B = 1 TO Block% + 0

PRINT #1, USING "######"; HI(B);
NEXT B
PRINT #1, " "
'PRINT #1, STRING$(80, "_")
PRINT #1, STRING$(80, "-")
COLOR 7, 0
'CALL MINUSVAL(MED(), BLOCK%)
IF Block% = 2 THEN Block1 = 1: Block2 = 2: CALL Ttest(TimeArray(),
StartTRCalc, Trials%, Block1, Block2, Tscore, Corr, BlFormat(), NoShow$(),
Distracted$())
IF Block% > 2 AND NumCon > 0 THEN GOTO MultiTs ELSE GOTO NoTs
MultiTs:
 FOR ConVal = 1 TO NumCon
  Block1 = Contrast(ConVal, 1): Block2 = Contrast(ConVal, 2)
  CALL Ttest(TimeArray(), StartTRCalc, Trials%, Block1, Block2, Tscore, Corr,
  BlFormat(), NoShow$(), Distracted$())
 NEXT ConVal
NoTs: ' Experimenter did not request specific contrasts for T test
IF Block% > 1 THEN CALL MINUSVAL(MED(), Block%)
 GOSUB PRINTALTSUMMARY
 IF TBORDER$ = "2" THEN GOSUB RESORTBLOCKS
RETURN FORM:
ERRFLAG = 4: ON ERROR GOTO Trouble
TIT$ = "BUSCHKE COGNOMETER COGNITIVE SPEEDOMETER"
PRINT #1, SPC(40 - CINT(LEN(TIT$) / 2)); TIT$
PRINT #1, SPC(37); "Page 1 "
PRINT #1, " ": PRINT #1, " "
'PRINT #1, "NAME   : "; SUBJECT.LASTNAME$; ", "; SUBJECT.FIRSTNAME$
PRINT #1, "NAME   : "; Subject.Lastname$; ", "; Subject.Firstname$; : PRINT
#1, SPC(30 - ((LEN(Subject.Lastname$)) + (LEN(Subject.Firstname$)))); " DATA
FILE : "; OUTFIL$ + ".SF"
'PRINT #1, "ID     : "; SUBJECT.ID$
PRINT #1, "ID     : "; subject.id$; : IF LEN(PARAF$) < 1 THEN PRINT #1, "":
ELSE PRINT #1, SPC(30 - LEN(subject.id)); "   PARAMETER FILE : "; PARAF$ +
".SPA"
PRINT #1, "AGE    : "; subject.age$
PRINT #1, "SEX    : "; subject.sex$
'PRINT #1, ""
PRINT #1, "STUDY  : "; subject.studyname$
PRINT #1, ""
PRINT #1, "DATE   : "; DATE$
PRINT #1, "TIME   : "; TIME$
PRINT #1, " "

IF DIGSIZE = 1 AND MODE$ = "1" THEN PRINT #1, "LARGE SIZE ONE-DIGIT
NUMBERS": 'LARGE SIZE"
IF DIGSIZE = 1 AND MODE$ = "2" THEN PRINT #1, "STANDARD SIZE ONE-DIGIT
NUMBERS": 'STANDARD SIZE"
IF DIGSIZE = 2 AND MODE$ = "1" THEN PRINT #1, "LARGE SIZE TWO-DIGIT
NUMBERS": 'LARGE SIZE"
IF DIGSIZE = 2 AND MODE$ = "2" THEN PRINT #1, "STANDARD SIZE TWO-DIGIT
NUMBERS": 'STANDARD SIZE"

PRINT #1, "NUMBER OF TRIALS PER BLOCK ="; Trials%
PRINT #1, "NUMBER OF BLOCKS ="; Block%
'IF TBORDER$ = "1" THEN PRINT #1, "SAME STIMULUS ORDER ACROSS BLOCKS"
```

```
'IF TBORDER$ = "2" THEN PRINT #1, "RANDOMIZED PRESENTATION ACROSS BLOCKS"

IF Block% = 1 THEN GOTO PACING
IF TYPEBLOCK$ = "1" THEN PRINT #1, "EVERY BLOCK RANDOM"

CONSIST$ = "Y": CONSIST = 1
FOR B = 1 TO Block% - 1
 IF BlFormat(B, 1) = 3 THEN GOTO NEXTBL 'IF CONSIST$ = "Y" AND BLFORMAT(B, 3) = BLFORMAT(B + 1, 3) THEN CONSIST$ =
"Y": CONSIST = BLFORMAT(B, 3) ELSE CONSIST$ = "N"
   IF CONSIST$ = "Y" AND BlFormat(B, 3) = BlFormat(B + 1, 3) THEN CONSIST$ =
"Y" ELSE CONSIST$ = "N"
    CONSIST = BlFormat(B, 3): 'ELSE CONSIST$ = "N"

NEXTBL:  '
NEXT B
IF TBORDER$ = "1" AND CONSIST$ = "Y" AND CONSIST = 1 THEN PRINT #1, "SAME
STIMULI IN SAME ORDER ACROSS BLOCKS"
IF TBORDER$ = "1" AND CONSIST$ = "Y" AND CONSIST = 2 THEN PRINT #1, "SAME
RESPONSES IN SAME ORDER ACROSS BLOCKS"
IF TBORDER$ = "2" AND CONSIST$ = "Y" AND CONSIST = 1 THEN PRINT #1, "SAME
STIMULI IN RANDOM ORDER ACROSS BLOCKS"
IF TBORDER$ = "2" AND CONSIST$ = "Y" AND CONSIST = 2 THEN PRINT #1, "SAME
RESPONSES IN RANDOM ORDER ACROSS BLOCKS"

PACING:
IF TYPEISI$ = "1" THEN PRINT #1, "FIXED INTERVAL OF "; ISI$; " SECONDS"
IF TYPEISI$ = "2" THEN PRINT #1, "SELF-PACED WITH A "; KISI$; " SEC DELAY"
IF SHOWRES$ = "N" THEN PRINT #1, "SCORES NOT SHOWN"
IF SHOWRES$ = "Y" AND SHOWCOMP$ = "N" THEN PRINT #1, "SHOW SCORES"
IF SHOWRES$ = "Y" AND SHOWCOMP$ = "Y" THEN PRINT #1, "SHOW SCORES AND
COMPARISONS"
PRINT #1, " "
FOR B = 1 TO Block%
 TRALS% = Trials%
 'IF B < BLOCK% THEN TRALS% = TRIALS% / 2 ELSE TRALS% = TRIALS%
 'PRINT #1, STRING$(80, "_")
 PRINT #1, STRING$(80, "-")
 PRINT #1, " "
 PRINT #1, "RESULTS OF BLOCK ["; B; "]:   ";
 IF BlFormat(B, 1) = 0 THEN PRINT #1, "COPY"; : GOTO PSTIM
 IF BlFormat(B, 1) = 3 THEN PRINT #1, "COPY"; : GOTO PSTIM
 IF BlFormat(B, 1) = 1 THEN PRINT #1, "ADDITIONS  ";
 IF BlFormat(B, 1) = 2 THEN PRINT #1, "SUBTRACTION ";
 IF BlFormat(B, 1) = 4 THEN PRINT #1, "ALTERNATION ";
 IF BlFormat(B, 1) = 5 THEN PRINT #1, "RANDOM      ";
 IF BlFormat(B, 1) > 0 THEN PRINT #1, BlFormat(B, 2); " ";
 IF BlFormat(B, 1) > 0 THEN IF BlFormat(B, 3) = 1 THEN PRINT #1, "SAMPLE
SAME";
 IF BlFormat(B, 1) > 0 THEN IF BlFormat(B, 3) = 2 THEN PRINT #1, "RESPONSE
SAME";
 IF BlFormat(B, 1) < 4 THEN PRINT #1, " ": GOTO PSTIM
   SELECT CASE NoShow$(B)
     CASE "N": PRINT #1, "   CUED";
     CASE "Y": PRINT #1, "   NO CUE";
     CASE "R": PRINT #1, "   REVERSE";
     CASE ELSE:
   END SELECT
PSTIM:
  IF Distracted$(B, 1) = "Y" AND Distracted$(B, 2) = "Y" THEN PRINT #1, "
FLASHING DISTRACTION";
  IF Distracted$(B, 1) = "Y" AND Distracted$(B, 2) = "N" THEN PRINT #1, "
DISTRACTION";
  PRINT #1, " "
  PRINT #1, "STIMULI ";
  FOR T = 1 TO TRALS%
  PRINT #1, USING "######"; STIM(B, T);
  IF T MOD 10 = 0 THEN PRINT #1, " ": PRINT #1, "          ";
  NEXT T: PRINT #1, " "
```

```
  PRINT #1, "ANSWERS ";
  FOR T = 1 TO TRALS%
   PRINT #1, USING "#######"; ANSWER(B, T);
   IF T MOD 10 = 0 THEN PRINT #1, " ": PRINT #1, "         ";
  NEXT T: PRINT #1, " "
  PRINT #1, "RESPONSE";
  FOR T = 1 TO TRALS%
   PRINT #1, USING "#######"; CHOICE(B, T);
   IF T MOD 10 = 0 THEN PRINT #1, " ": PRINT #1, "         ";
  NEXT T: PRINT #1, " "
  PRINT #1, "RT      ";
  FOR T = 1 TO TRALS%
   IF CINT(TimeArray(B, T)) <= 99999 THEN PRINT #1, USING "#######";
CINT(TimeArray(B, T));   ELSE PRINT #1, "99999";
   IF T MOD 10 = 0 THEN PRINT #1, " ": PRINT #1, "         ";
  NEXT T: PRINT #1, " "
  IF BlFormat(B, 1) = 5 THEN GOTO PRINTSEQ ELSE GOTO SKIPRANDSEQ
PRINTSEQ:
  PRINT #1, "SEQUENCE";
  FOR T = 1 TO TRALS%
   IF RANDOMT(B, T) = 1 THEN PRINT #1, "      C";  ELSE PRINT #1, "      S";
   'PRINT #1, USING "#######"; RANDOMT(B, T);
   IF T MOD 10 = 0 THEN PRINT #1, " ": PRINT #1, "         ";
  NEXT T: PRINT #1, " "
SKIPRANDSEQ:
  FOR T = 1 TO TRALS%
   IF TimeArray(B, T) <= 0 THEN GOTO SKIPOVER
   NRIGHT = NRIGHT + 1
   SUMRIGHT = SUMRIGHT + TimeArray(B, T)
   SUMSQ1 = SUMSQ1 + (TimeArray(B, T) * TimeArray(B, T))
SKIPOVER:   'ERROR VALUE
  NEXT T
  FOR BADT = 1 TO ER(B)
   SUMWRONG = SUMWRONG + ERTIME(B, BADT)
   SUMSQ2 = SUMSQ2 + (ERTIME(B, BADT) * ERTIME(B, BADT))
  NEXT BADT
  IF NRIGHT > 0 THEN Meanright(B) = CINT(SUMRIGHT / NRIGHT) ELSE Meanright(B)
= 0
  IF ER(B) > 0 THEN MEANWRONG(B) = CINT(SUMWRONG / ER(B))
  NUMT = TRALS%
  CALL STANDARDDEV(NRIGHT, SUMRIGHT, SUMSQ1, SD)
  STANDRIGHT(B) = SD
  CALL STANDARDDEV(ER(B), SUMWRONG, SUMSQ2, SD)
  STANDWRONG(B) = SD
  FOR X = 1 TO TRALS%
  IF TimeArray(B, X) <= 0 THEN GOTO SKPMED
  C = C + 1
  AR(C) = TimeArray(B, X)
SKPMED: 'BAD VALUE
  NEXT X
  'CALL MEDIAN(C, MED1, LO, HI, QUARTILE, P25, P75)
  CALL BYMEAN(B, StartTRCalc, RankArray(), AR(), C, MEAN, SD, MED1, BiMean,
Mad, P25, P75, QUARTILE, LO1, HI1)
  MED(B) = MED1: QUART(B) = QUARTILE: PERCENTILE(B, 1) = P25: PERCENTILE(B, 2)
= P75: BWM(B) = BiMean
  PRINT #1, " "
  PRINT #1, "MEAN CORRECT TRIALS ="; CINT(Meanright(B));
  PRINT #1, "       STANDARD DEVIATION ="; CINT(STANDRIGHT(B))
  PRINT #1, "MEDIAN ="; CINT(MED(B)); "   LOW ="; CINT(LO1); "   HIGH =";
CINT(HI1); "   SEMI-INTERQUARTILE ="; CINT(QUART(B))
  'PRINT #1, "BIMEAN ="; CINT(BWM(B))
  IF (BWM(B)) > 0 THEN PRINT #1, "BIMEAN ="; CINT(BWM(B))

PRINT #1, " "
  IF ER(B) > 0 THEN PRINT #1, "MEAN ERROR TRIALS ["; ER(B); "] =";
CINT(SUMWRONG / ER(B));
  IF ER(B) > 0 THEN PRINT #1, "   STANDARD DEVIATION ="; CINT(STANDWRONG(B))
  'PRINT #1, : PRINT #1, " "
  'PRINT #1, " "
  SUMRIGHT = 0: SUMWRONG = 0: SUMSQ1 = 0: SUMSQ2 = 0: NRIGHT = 0: C = 0
```

```
IF OUTOF$ = "1" THEN COLOR 0, 7: LOCATE 22, 22: INPUT "HIT RETURN TO
CONTINUE"; GARB$: COLOR 7, 0: CLS
GOSUB ALTERNATESUMMARY: 'WILL GIVE YOU COPY AND SUBTRACTION INDIVIDUALLY FOR
ALTERNATION
NEXT B
 'PRINT #1, STRING$(80, "_")
 PRINT #1, STRING$(80, "-")
 PRINT #1, CHR$(12): 'FORM FEED
RETURN

DISKSAVE:
 CLS : CODENUM = 1: TryChoice = 0: 'GOTO SendOut
 '''DEMO''' LOCATE 4, 35: COLOR 0, 7: PRINT " DATA OUTPUT "; : COLOR 7, 0
 '''DEMO''' T = 8: B = 16: L = 12: R = 70: CALL BOX(T, L, R, B): ON ERROR
GOTO GETCHOICE
 PR1$ = "Too many errors!":   ''' "Percent correct was below ":   ''' "Percent
Correct Values are Below "
 PR2$ = "Please wait for menu, then try again": ''''"You must Do Another Trial
Block"
 '''DEMO''' IF PassRun$ = "N" THEN LOCATE 18, 40 - ((LEN(PR1$) + 4) / 2):
PRINT PR1$; : COLOR 31, 0: PRINT USING "###"; PassPercent; : PRINT "%"; :
COLOR 7, 0
 '''DEMO''' IF PassRun$ = "N" THEN LOCATE 20, 40 - ((LEN(PR2$)) / 2): PRINT
PR2$; : COLOR 7, 0
 '''DEMO''' LOCATE 6, 16: PRINT "PRESS "; : COLOR 0, 7: PRINT " RETURN "; :
COLOR 7, 0: PRINT " FOR <DEFAULT> "; : LOCATE 6, 48: PRINT "PRESS "; : COLOR
0, 7: PRINT " * "; : COLOR 7, 0: PRINT " TO REDO"
 CALL CLEARKEYBOARD: KEYHIT$ = "Y": NAMEFILE$ = OUTFIL$: DRIVE$ = "C:": GOTO
DEMOOUT GETCHOICE: LOCATE 9, 14, 1, 6, 10: INPUT "SAVE ON DISK <Y>: "; KEYHIT$
 KEYHIT$ = UCASE$(KEYHIT$)
 IF KEYHIT$ = "" THEN KEYHIT$ = "Y"
 IF KEYHIT$ <> "Y" AND KEYHIT$ <> "N" THEN LOCATE 9, 35: PRINT SPC(6); :
BEEP: GOTO GETCHOICE
 IF KEYHIT$ = "N" AND TryChoice = 0 THEN LOCATE 10, 14: COLOR 0, 7: PRINT "
TO SEE RESULTS MUST SAVE FILE "; : COLOR 7, 0: LOCATE 9, 34: PRINT SPC(4); :
BEEP: TryChoice = TryChoice + 1: GOTO GETCHOICE
 IF KEYHIT$ = "N" THEN GOTO NODISK
 IF KEYHIT$ = "Y" THEN LOCATE 17, 29: PRINT "PRESS "; : COLOR 0, 7: PRINT " ?
"; : COLOR 7, 0: PRINT " TO SEE FILE NAMES "

GETFILE: LOCATE 11, 14: PRINT SPC(40); : LOCATE 10, 14, 1, 6, 10: PRINT
SPC(45); : LOCATE 10, 14: PRINT "ENTER FILE NAME <"; OUTFIL$; : INPUT ".SPD>:
"; NAMEFILE$
 IF NAMEFILE$ = "*" THEN FOR LI = 9 TO 11: LOCATE LI, 14: PRINT SPC(45); :
NEXT LI: FOR LI = 17 TO 23: LOCATE LI, 1: PRINT SPC(78); : NEXT LI: GOTO
GETCHOICE
 IF NAMEFILE$ = "" THEN NAMEFILE$ = OUTFIL$
 IF NAMEFILE$ = "" THEN GOTO GETFILE
 IF LEN(NAMEFILE$) > 8 THEN LOCATE 11, 14: COLOR 0, 7: PRINT " NAME TOO LONG
"; : COLOR 7, 0: GOTO GETFILE
 IF INSTR(NAMEFILE$, ".") > 0 THEN LOCATE 11, 14: COLOR 0, 7: PRINT " SUFFIX
[.SPD] NOT NEEDED"; : COLOR 7, 0: GOTO GETFILE
 LOCATE 11, 14, 0: PRINT SPC(36);
LOCATE 17, 29: PRINT SPC(45); : FOR LI = 17 TO 23: LOCATE LI, 1: PRINT
SPC(78); : NEXT LI
GETDRIVE: IF INSTR(OLDDRIVE$, ":") > 0 THEN OLDDRIVE$ = LEFT$(OLDDRIVE$, 1)
 LOCATE 11, 14, 1, 6, 10: PRINT SPC(30); : LOCATE 11, 14: PRINT "ENTER DRIVE
<"; OLDDRIVE$; : INPUT ">: "; DRIVE$
 IF DRIVE$ = "*" THEN FOR LI = 9 TO 11: LOCATE LI, 14: PRINT SPC(45); : NEXT
LI: GOTO GETCHOICE
 IF DRIVE$ = "" THEN DRIVE$ = OLDDRIVE$
 IF NAMEFILE$ = "?" THEN LOCATE 16, 1, 0: SHELL "DIR " + DRIVE$ + "*.S/W":
GOTO GETFILE:

DRIVE$ = UCASE$(DRIVE$)
IF INSTR(DRIVE$, ":") = 0 THEN DRIVE$ = DRIVE$ + ":"
OLDDRIVE$ = DRIVE$
IF ((DRIVE$ <> "A:") AND (DRIVE$ <> "B:") AND (DRIVE$ <> "C:") AND (DRIVE$
```

```
        <> "D:")) THEN BEEP: GOTO GETDRIVE
       FOR LI = 17 TO 23: LOCATE LI, 1, 0: PRINT SPC(78); : NEXT LI

DEMOOUT: DAY$ = LEFT$(DATE$, 6) + RIGHT$(DATE$, 2): TYME$ = LEFT$(TIME$, 2) +
".". + MID$(TIME$, 4, 2)
  HOMEDRIVE$ = DRIVE$: OUTFIL$ = NAMEFILE$
    IF ((PassRun$ = "N") OR (ESCAPE$ = "Y")) THEN LOCATE 12, 40 - ((LEN(PR1$) +
4) / 2): PRINT PR1$; : COLOR 7, 0: '''<<<DEMO''' COLOR 31, 0: PRINT USING
"###"; PassPercent; : PRINT "%"; : COLOR 7, 0
    IF ((PassRun$ = "N") OR (ESCAPE$ = "Y")) THEN LOCATE 14, 40 - ((LEN(PR2$))
/ 2): PRINT PR2$; :   COLOR 7, 0
    IF ((PassRun$ = "Y") AND (ESCAPE$ = "N")) THEN LOCATE 12, 24, 0: PRINT
"Please wait....scoring....": '''<<<DEMO'''

SendOut: ERRFLAG = 4: ON ERROR GOTO Trouble
  '''DEMO''' OPEN HOMEDRIVE$ + OUTFIL$ + ".S" FOR APPEND AS #1
  '''DEMO''' GOSUB SAVERAWDATA
  '''DEMO''' CLOSE #1
  OPEN "NUL" FOR APPEND AS #1: '''<<<DEMO''' OPEN HOMEDRIVE$ + OUTFIL$ + ".SF"
FOR APPEND AS #1
  GOSUB FORM
  GOSUB NEWERPRINT
  CLOSE #1: '''<<<DEMO''' COLOR 31, 0: LOCATE 14, 14, 0: PRINT "SAVING..[";
OUTFIL$ + ".S"; ", "; OUTFIL$ + ".SF"; "]"; : COLOR 7, 0
  IF DAYRUN$ = "1" THEN SUMFILE$ = "SPEED1.SUM" ELSE IF DAYRUN$ = "2" THEN
SUMFILE$ = "SPEED2.SUM" ELSE SUMFILE$ = "SPEED.SUM"
  '''DEMO''' OPEN HOMEDRIVE$ + SUMFILE$ FOR APPEND AS #1
  '''DEMO''' GOSUB SAVESUMS
  '''DEMO''' CLOSE #1
  OPEN HOMEDRIVE$ + OUTFIL$ + ".SS" FOR APPEND AS #1
  GOSUB SAVESUMS
  CLOSE #1
NODISK: REM JUST GET OUT
RETURN Trouble:
LOCATE 22, 26: PRINT "ERROR NUMBER "; ERR; " HAS OCCURRED.["; ERL; "]"
LOCATE 23, 30: CLOSE #1

SELECT CASE ERR
   CASE 54
   DE$ = "BAD FILE MODE "
   CASE 64
   DE$ = "BAD FILE NAME"
   CASE 68
   DE$ = "DEVICE UNAVAILABLE"
   CASE 61
   DE$ = "DISK FULL"
   CASE 71
   DE$ = "DISK NOT READY"
   CASE 53
   DE$ = "FILE NOT FOUND"
   CASE ELSE
   DE$ = "NOT IN LIBRARY"
END SELECT
  SKP = CINT(LEN(DE$) / 2)
  LOCATE 23, 40 - SKP: COLOR 31, 0: PRINT DE$: COLOR 7, 0
  '''IF ERRFLAG = 8 OR NoTimer$ = "Y" THEN LOCATE 23, 40 + SKP + 2: PRINT "
[TIME.DIV] "
  '''LOCATE 24, 25: LINE INPUT " PRESS RETURN KEY TO CONTINUE "; XX$
  LOCATE 22, 1: PRINT STRING$(70, " ")
  LOCATE 23, 1: PRINT STRING$(70, " ")
  LOCATE 24, 1: PRINT STRING$(70, " ")
  IF ((ERRFLAG = 1) OR (ERRFLAG = 3) OR (ERRFLAG = 4)) THEN CLOSE #1
  '''IF NoTimer$ = "Y" THEN RUN "C:$MENU.EXE"
  IF NoTimer$ = "Y" THEN CLS : LOCATE 12, 14: PRINT "No timing file
found...Loading $MENU to make it...": RUN "$MENU": END REM IF ERR=71 THEN RESUME GETMEFILES
  REM IF ERRFLAG=1 THEN RESUME GETMEFILES
```

```
     REM IF ERRFLAG=2 THEN RESUME OPENDIRFILE
     REM IF ERRFLAG=3 THEN RESUME GETMEFILES
     IF ERRFLAG = 4 THEN RESUME DISKSAVE
     REM IF ERRFLAG=5 THEN RESUME GETOLDDATA
     RESUME 0
RETURN

RESORTBLOCKS:
RETURN

SAVERAWDATA:
 FOR B = 1 TO Block%
  S$ = ","
  IF ((BlFormat(B, 1) = 0) OR (BlFormat(B, 1) = 3)) THEN PRINT #1, " C"; S$;
  IF BlFormat(B, 1) = 1 THEN PRINT #1, "+"; : PRINT #1, USING "#";
BlFormat(B, 2); : PRINT #1, S$;
  IF BlFormat(B, 1) = 2 THEN PRINT #1, "-"; : PRINT #1, USING "#";
BlFormat(B, 2); : PRINT #1, S$;
  IF BlFormat(B, 1) = 4 THEN PRINT #1, "ALT"; : PRINT #1, USING "#";
BlFormat(B, 2); : PRINT #1, S$;
  IF BlFormat(B, 1) = 5 THEN PRINT #1, "RND"; : PRINT #1, USING "#";
BlFormat(B, 2); : PRINT #1, S$;
  TRLS% = Trials%
  FOR T = 1 TO TRLS%
   PRINT #1, STIM(B, T); S$; CHOICE(B, T); S$; : PRINT #1, USING "#####";
TimeArray(B, T); : PRINT #1, S$;
  NEXT T
 NEXT B
 PRINT #1, " "
RETURN REVISEDMENU: COLOR 7, 0
' CLS : RUN "C:MENUDX": END
' PassRun$ = "Y"

9000   CLS : ON ERROR GOTO 9000: CC$ = ""
       LOCATE 8, 32: COLOR 0, 7: PRINT " COGNOMETER MENU "; : COLOR 7, 0
       'LOCATE 4, 12: PRINT " PRESS "; : COLOR 0, 7: PRINT " 3 "; : COLOR 7,
       0: PRINT " OR "; : COLOR 0, 7: PRINT " 4 "; : COLOR 7, 0: PRINT " FOR
       SUMMARIES "; : LOCATE 4, 46: COLOR 0, 7: PRINT " 5 "; : COLOR 7, 0:
       PRINT " TO CHANGE PARAMETERS"
9001   T = 9: B = 17: L = 29: R = 51: CALL BOX(T, L, R, B): GOTO 9007: X$ =
STRING$(19, 205)
9002   LOCATE 10, 30: PRINT CHR$(201); : LOCATE 10, 50: PRINT CHR$(187); :
LOCATE 16, 30: PRINT CHR$(200);
9003   LOCATE 16, 50: PRINT CHR$(188);
9004   LOCATE 10, 31: PRINT X$;
9005   LOCATE 16, 31: PRINT X$;
9006   FOR X = 11 TO 15: LOCATE X, 30: PRINT CHR$(186); : LOCATE X, 50: PRINT
CHR$(186); : NEXT X
9007   LOCATE 10, 35: COLOR 0, 7: PRINT " R "; : COLOR 7, 0: PRINT " Recall";
9008   LOCATE 12, 35: COLOR 0, 7: PRINT " C "; : COLOR 7, 0: PRINT "   Copy";
       LOCATE 14, 35: COLOR 0, 7: PRINT " S "; : COLOR 31, 0: PRINT " Speed";
       IF PassRun$ = "N" OR BADRUN$ = "Y" THEN LOCATE 14, 32: PRINT CHR$(16);

'''LOCATE 13, 34: COLOR 0, 7: PRINT " A "; : COLOR 7, 0: PRINT "
Analysis";
       '''LOCATE 15, 34: COLOR 0, 7: PRINT " N "; : COLOR 7, 0: PRINT "   New
Subject";
       '''LOCATE 17, 34: COLOR 0, 7: PRINT " P "; : COLOR 7, 0: PRINT "
Parameters";
9011   LOCATE 16, 35: COLOR 0, 7: PRINT " Q "; : COLOR 7, 0: PRINT "   Quit";
       PassRun$ = "Y"
       BADRUN$ = "N"
       ESCAPE$ = "N"
9012   LOCATE 17, 41, 0
9013   CC$ = INKEY$: IF CC$ = "" THEN 9013
       CC$ = UCASE$(CC$)
9014   IF ((CC$ = "R") OR (CC$ = "C") OR (CC$ = "S") OR (CC$ = "Q")) THEN
```

```
9016 ELSE LOCATE 19, 33: PRINT "MUST BE R,C,S,Q"; : GOTO 9012
9016    IF ((CC$ = "R")) THEN CLS : RUN DRIVE$ + "$RECALL": END
9018    IF ((CC$ = "C")) THEN CLS : RUN DRIVE$ + "$COPY": END
        IF ((CC$ = "S")) THEN CLS : GOTO NEWRUN: 'END
        '''IF ((CC$ = "A")) THEN CLS : RUN DRIVE$ + "RXSTATS": END

'''IF ((CC$ = "N")) THEN CLS : EDIT.IT$ = "Y": CALL
givemesubjectstory(DRIVE$, EDIT.IT$, Subject.Lastname$, Subject.Firstname$,
subject.id$, subject.age$, subject.sex$, subject.date$, subject.study$,
subject.studyname$): GOSUB GETSUBJECTFILE: GOTO RE VISEDMENU
        '''IF ((CC$ = "N")) THEN SI$ = LEFT$(Subject.Firstname$, 1): SI$ = SI$
+ LEFT$(Subject.Lastname$, 1): SI$ = SI$ + LEFT$(subject.id$, 4): GOTO
BEGINRUN
        '''IF CC$ = "P" THEN GOTO TOPOFRUN
9020    IF ((CC$ = "Q")) THEN CLS : LOCATE 1, 1, 0: END:   '''DEMO
9040    IF MODESET$ = "1" THEN SHELL "MODE 40"
        RETURN SAVESUMS:
 'SAVE SUMMARY DATA
 'ON ERROR GOTO 0
 Missval = -1
 S$ = ",": DAY$ = LEFT$(DATE$, 6) + RIGHT$(DATE$, 2): TYME$ = LEFT$(TIME$, 2)
+ "." + MID$(TIME$, 4, 2)
 PRINT #1, Subject.Lastname$; S$; Subject.Firstname$; S$; subject.id$; S$;
subject.age$; S$; subject.sex$; S$; DAY$; S$; TYME$; S$; DIGSIZE; S$;
TYPEBLOCK$; S$; TBORDER$; S$; Block%; S$;
 FOR NB = 1 TO Block% + 0: ' FOR COPY AND SUBTRACTION SCORES ON ALTERNATION
BLOCK
 IF PassRun$ = "Y" THEN GOTO savegood ELSE GOTO savebad
savegood:
 BLO = (2 * NB) - 1:   'BLOCK = 3
 'COPY,SUBTRACTION,ALTERNATION,COPY,SUBTRACTION,COPY1,COPY2,SUB1,SUB2
   PRINT #1, BlFormat(NB, 1); S$; NUMCORRECT(NB); S$; Meanright(NB); S$;
STANDRIGHT(NB); S$; BWM(NB); S$; MED(NB); S$; QUART(NB); S$; LO(NB); S$;
HI(NB); S$;
   PRINT #1, NUMALTCORRECT(BLO); S$; MeanALTright(BLO); S$;
STANDALTRIGHT(BLO); S$; ALTBWM(BLO); S$; ALTMED(BLO); S$; ALTQUART(BLO); S$;
ALTLO(BLO); S$; ALTHI(BLO); S$;
   PRINT #1, NUMALTCORRECT(BLO + 1); S$; MeanALTright(BLO + 1); S$;
STANDALTRIGHT(BLO + 1); S$; ALTBWM(BLO + 1); S$; ALTMED(BLO + 1); S$;
ALTQUART(BLO + 1); S$; ALTLO(BLO + 1); S$; ALTHI(BLO + 1);
   IF NB < Block% THEN PRINT #1, S$;
   GOTO skipbad
savebad:
   FOR nval = 1 TO 25: PRINT #1, Missval;
   IF nval <= 24 THEN PRINT #1, S$;  ELSE IF nval = 25 AND NB < Block% THEN
PRINT #1, S$;
   NEXT nval
skipbad:   '
 NEXT NB
 PRINT #1, " "
RETURN GETSUMS:
COMPTYPE$ = "": ' was No Comparison before Jan 10, 1990
 'READ PRIOR SUMMARY DATA
 STARTTR = 4: ENDTR = 6: COPTR = 0: SUBTR = 0: TOTTR = 0: DIFFTR = 0
 ' Previously was STARTTR=1:ENDTR=20:next line remarked:then MAXREC=3
 MAXREC = ENDTR - STARTTR + 1
 'MAXREC = 3
 OPEN HOMEDRIVE$ + OUTFIL$ + ".SS" FOR INPUT AS #1
 'OPEN HOMEDRIVE$ + "SPEED.SUM" FOR INPUT AS #1

WHILE NOT EOF(1)
 GoodRun$ = "Y"
 TOTTR = TOTTR + 1
 INPUT #1, Subject.Lastname$, Subject.Firstname$, subject.id$, subject.age$,
```

```
subject.sex$, DAY$, TYME$, DSIZE, TBLOCK$, TBORD$, Block%
  IF DSIZE <> DIGSIZE OR TBLOCK$ <> TYPEBLOCK$ OR TBORD$ <> TBORDER$ THEN
GoodRun$ = "N"
  FOR NB = 1 TO Block%:   ' FOR COPY AND SUBTRACTION SCORES ON ALTERNATION
BLOCK
    INPUT #1, Blform, NUMCOR, Mea, ST, BW, OLDMED, QUAT, LO(NB), HI(NB),
NUMALTCORRECT(BLO), MeanALTright(BLO), STANDALTRIGHT(BLO), ALTBWM(BLO),
ALTMED(BLO), QUART(BLO), ALTLO(BLO), ALTHI(BLO), NUMALT, MBLO, STAND, ALT,
ALT, QUA, ALT, ALTHI
    IF OLDMED = -1 THEN GoodRun$ = "N": ' 12-13-89 to deal with runs less than
80%
    IF BlFormat(1, 1) = 3 AND BlFormat(2, 1) = 2 THEN GOTO COPSUB ELSE GOTO
SUBCOP
COPSUB:
   IF GoodRun$ = "N" THEN GOTO NEXTBLOCK
   IF TOTTR >= STARTTR AND TOTTR <= ENDTR AND COPTR < MAXREC AND NB = 1 AND
Blform = 3 THEN COPTR = COPTR + 1: COPRT(COPTR) = OLDMED:  '   PRINT "C";
MED(NB); ",";
   IF TOTTR >= STARTTR AND TOTTR <= ENDTR AND NB = 2 AND SUBTR < MAXREC AND
Blform = 2 THEN SUBTR = SUBTR + 1: SUBRT(SUBTR) = OLDMED: ' PRINT "S";
MED(NB); ",";
   IF TOTTR >= STARTTR AND TOTTR <= ENDTR AND DIFFTR < MAXREC AND NB = 2 THEN
DIFFTR = DIFFTR + 1: DIFFRT(DIFFTR) = SUBRT(SUBTR) - COPRT(COPTR): 'PRINT
"D"; DIFFRT(DIFFTR); ",";
   IF SUBTR > 0 AND SUBTR <= MAXREC AND NB = 2 AND COPRT(COPTR) > SUBRT(SUBTR)
THEN COPTR = COPTR - 1: SUBTR = SUBTR - 1: DIFFTR = DIFFTR - 1: 'PRINT "BAD
DIFF:"; DIFFRT(DIFFTR + 1)

GOTO NEXTBLOCK
SUBCOP:
   IF GoodRun$ = "N" THEN GOTO NEXTBLOCK
   IF TOTTR >= STARTTR AND TOTTR <= ENDTR AND COPTR < MAXREC AND NB = 2 AND
Blform = 3 THEN COPTR = COPTR + 1: COPRT(COPTR) = OLDMED
   IF TOTTR >= STARTTR AND TOTTR <= ENDTR AND SUBTR < MAXREC AND NB = 1 AND
Blform = 2 THEN SUBTR = SUBTR + 1: SUBRT(SUBTR) = OLDMED
   IF TOTTR >= STARTTR AND TOTTR <= ENDTR AND DIFFTR < MAXREC AND NB = 2 THEN
DIFFTR = DIFFTR + 1: DIFFRT(DIFFTR) = SUBRT(SUBTR) - COPRT(COPTR)
   IF SUBTR > 0 AND SUBTR <= MAXREC AND NB = 2 AND COPRT(COPTR) > SUBRT(SUBTR)
THEN COPTR = COPTR - 1: SUBTR = SUBTR - 1: DIFFTR = DIFFTR - 1

NEXTBLOCK: '
 NEXT NB
 'LINE INPUT #1, GARB$
 WEND
 CLOSE #1
 IF COPTR < MAXREC OR SUBTR < MAXREC THEN COPYCUT = 20000: SUBCUT = 20000:
DIFFCUT = 20000: GOTO SKIPCALC
 COMPTYPE$ = " PERSONAL COMPARISON "
 FOR X = 1 TO COPTR: AR(X) = COPRT(X): NEXT X
 CALL BYMEAN(0, StartTRCalc, RankArray(), AR(), COPTR, MEAN, SD, MED1,
BiMean, Mad, P25, P75, QUARTILE, LO1, HI1)
 'LOCATE , 1: PRINT MEAN; : PRINT SD; : INPUT XX$
 COPYCUT = MEAN + ((1.64) * SD)
 'LOCATE , 1: PRINT COPYCUT; : INPUT XX$
 FOR X = 1 TO SUBTR: AR(X) = SUBRT(X): NEXT X
 CALL BYMEAN(0, StartTRCalc, RankArray(), AR(), SUBTR, MEAN, SD, MED1,
BiMean, Mad, P25, P75, QUARTILE, LO1, HI1)
 'LOCATE , 1: PRINT MEAN; : PRINT SD; : INPUT XX$
 SUBCUT = MEAN + ((1.64) * SD)
 'LOCATE , 1: PRINT SUBCUT; : INPUT XX$ FOR X = 1 TO DIFFTR: AR(X) = DIFFRT(X): NEXT X
 CALL BYMEAN(0, StartTRCalc, RankArray(), AR(), DIFFTR, MEAN, SD, MED1,
BiMean, Mad, P25, P75, QUARTILE, LO1, HI1)
 'LOCATE , 1:  PRINT MEAN; : PRINT SD; : INPUT XX$
 DIFFCUT = MEAN + ((1.64) * SD)
 'LOCATE , 1: PRINT "DIFFCUT= "; : PRINT DIFFTR; : PRINT DIFFCUT; : PRINT
MED1; : PRINT MEAN; : PRINT SD; : INPUT XX$

IF COPYCUT <= 0 THEN COPYCUT = 20000
 IF SUBCUT <= 0 THEN SUBCUT = 20000
```

```
 IF DIFFCUT <= 0 THEN DIFFCUT = 20000
SKIPCALC: IF COPYCUT = 20000 AND SUBCUT = 20000 THEN GOTO GETNORMFILE ELSE
GOTO SKIPFILE
GETNORMFILE:
 IF DIGSIZE <> 2 OR TYPEBLOCK$ <> "2" OR TBORDER$ <> "1" THEN GOTO SKIPFILE
 ON ERROR GOTO NONORM
 OPEN "NORM.SPD" FOR INPUT AS #1
 INPUT #1, COPYCUT, SUBCUT, DIFFCUT
 CLOSE #1
 COMPTYPE$ = " NORMATIVE COMPARISON "
SKIPFILE:
 'CLS :
 'PRINT HOMEDRIVE$ + OUTFIL$ + ".SS"; TOTTR; ","; COPYCUT; ","; SUBCUT; :
 INPUT GG$
RETURN

NONORM: CLOSE #1: RESUME SKIPFILE

ALTERNATESUMMARY:
 BLO = (2 * B) - 1:   'BLOCK = 3
 FOR T = StartTRCalc TO Trials%
  IF TimeArray(B, T) <= 0 THEN GOTO SKPIT2
  IF BlFormat(B, 1) = 5 THEN IF RANDOMT(B, T) = 1 THEN GOTO SUBADD
  IF BlFormat(B, 1) = 5 THEN IF RANDOMT(B, T) = 0 THEN GOTO SUBSUBTRACT
  IF T MOD 2 = 0 THEN GOTO SUBSUBTRACT
SUBADD:
  NADD = NADD + 1
  SUMADD = SUMADD + TimeArray(B, T)
  SUMSQ1ADD = SUMSQ1ADD + (TimeArray(B, T) * TimeArray(B, T))
  GOTO SKPIT2
SUBSUBTRACT:
  NSUB = NSUB + 1
  SUMSUB = SUMSUB + TimeArray(B, T)
  SUMSQ1SUB = SUMSQ1SUB + (TimeArray(B, T) * TimeArray(B, T))
SKPIT2:  'VALUE NOT INCLUDED SINCE ERROR SCORE
 NEXT T
 IF NADD > 0 THEN MeanALTright(BLO) = CINT(SUMADD / NADD) ELSE
MeanALTright(BLO) = 0
 IF NSUB > 0 THEN MeanALTright(BLO + 1) = CINT(SUMSUB / NSUB) ELSE
MeanALTright(BLO + 1) = 0
 NUMALTCORRECT(BLO) = NADD
 NUMALTCORRECT(BLO + 1) = NSUB
 NUMT = Trials% - StartTRCalc + 1
 CALL STANDARDDEV(NADD, SUMADD, SUMSQ1ADD, SD)
 STANDALTRIGHT(BLO) = SD
 CALL STANDARDDEV(NSUB, SUMSUB, SUMSQ1SUB, SD)
 STANDALTRIGHT(BLO + 1) = SD
 SB = 0: AD = 0
 FOR X = 1 TO Trials%
  IF X MOD 2 = 0 THEN IF TimeArray(B, X) > 0 THEN SB = SB + 1: ARSUB(SB) =
TimeArray(B, X)
  IF X MOD 2 <> 0 THEN IF TimeArray(B, X) > 0 THEN AD = AD + 1: ARADD(AD) =
TimeArray(B, X)
 NEXT X
 FOR X = 1 TO AD: AR(X) = ARADD(X): NEXT X
 'CALL MEDIAN(AD, MED1, LO1, HI1, QUARTILE, P25, P75)
  CALL BYMEAN(0, StartTRCalc, RankArray(), AR(), AD, MEAN, SD, MED1, BiMean,
Mad, P25, P75, QUARTILE, LO1, HI1)
  ALTLO(BLO) = LO1: ALTHI(BLO) = HI1: ALTBWM(BLO) = BiMean
  ALTMED(BLO) = MED1: ALTQUART(BLO) = QUARTILE: ALTPERCENT(BLO, 1) = P25:
ALTPERCENT(BLO, 2) = P75
  FOR X = 1 TO SB: AR(X) = ARSUB(X): NEXT X
  'CALL MEDIAN(SB, MED1, LO1, HI1, QUARTILE, P25, P75)
  CALL BYMEAN(0, StartTRCalc, RankArray(), AR(), SB, MEAN, SD, MED1, BiMean,
Mad, P25, P75, QUARTILE, LO1, HI1)
  ALTLO(BLO + 1) = LO1: ALTHI(BLO + 1) = HI1: ALTBWM(BLO + 1) = BiMean
  ALTMED(BLO + 1) = MED1: ALTQUART(BLO + 1) = QUARTILE: ALTPERCENT(BLO + 1, 1)
  = P25: ALTPERCENT(BLO + 1, 2) = P75
 SUMRIGHT = 0: SUMWRONG = 0: SUMSQ1 = 0: SUMSQ2 = 0: NRIGHT = 0: C = 0
 NADD = 0: NSUB = 0: SUMSQ1ADD = 0: SUMSQ1SUB = 0: NADDC1 = 0: NADDC2 = 0:
```

```
NSUBS1 = 0: NSUBS2 = 0
SUMSQC1 = 0: SUMSQC2 = 0: SUMSQS1 = 0: SUMSQS2 = 0: SUMADD = 0:   SUMSUB = 0:
SUMSUBS2 = 0
RETURN

PRINTALTSUMMARY:

PRINT #1, " ": 'PRINT #1, " " .
 PRINT #1, "     BREAKDOWN OF MIXED TRIALS"
 PRINT #1, " "
 PRINT #1, "           ";
 FOR B = 1 TO Block%
  SELECT CASE BlFormat(B, 1)
   CASE IS = 3: PRINT #1, "     COPY     ";
   CASE IS = 2: PRINT #1, "    SUBTRACT  ";
   CASE IS = 1: PRINT #1, "    ADDITION  ";
   CASE IS = 4: PRINT #1, "   ALTERNATION";
   CASE IS = 5: PRINT #1, "     RANDOM   ";
   CASE ELSE: '
  END SELECT
 NEXT B: PRINT #1, " ":
 PRINT #1, " "
 PRINT #1, "           ";
 FOR B = 1 TO Block%
  SELECT CASE BlFormat(B, 1)
   CASE IS = 3: PRINT #1, "              ";
   CASE IS = 2: PRINT #1, "              ";
   CASE IS = 1: PRINT #1, "              ";
   CASE IS = 4: PRINT #1, "     C     S";
   CASE IS = 5: PRINT #1, "     C     S";
   CASE ELSE: '
  END SELECT
 NEXT B: PRINT #1, " ":
 PRINT #1, STRING$(80, "-")
 PRINT #1, "CORRECT";
 FOR B = 1 TO Block% * 2
  PRINT #1, USING "######"; NUMALTCORRECT(B);
 NEXT B
 PRINT #1, " "
 PRINT #1, " "
 PRINT #1, "MEAN    ";
 FOR B = 1 TO Block% * 2
  PRINT #1, USING "######"; MeanALTright(B);
 NEXT B
 PRINT #1, " ": PRINT #1, "SD    ";
 FOR B = 1 TO Block% * 2
  PRINT #1, USING "######"; STANDALTRIGHT(B);
 NEXT B
 PRINT #1, " "
 'PRINT #1, STRING$(12 * BLOCK%, "_")
 PRINT #1, STRING$(80, "-")
 PRINT #1, " ": PRINT #1, "MED    ";
 FOR B = 1 TO Block% * 2
  PRINT #1, USING "######"; ALTMED(B);
 NEXT B
 PRINT #1, " ": PRINT #1, "SINTQRT";
 FOR B = 1 TO Block% * 2
  PRINT #1, USING "######"; ALTQUART(B);
 NEXT B
 PRINT #1, " ": PRINT #1, "LOW    ";
 FOR B = 1 TO Block% * 2
  PRINT #1, USING "######"; ALTLO(B);
 NEXT B
 PRINT #1, " ": PRINT #1, " 25%ile";
 FOR B = 1 TO Block% * 2
  PRINT #1, USING "######"; ALTPERCENT(B, 1);
 NEXT B
 PRINT #1, " ": PRINT #1, " 75%ile";
 FOR B = 1 TO Block% * 2
```

```
  PRINT #1, USING "#######"; ALTPERCENT(B, 2);
 NEXT B
 PRINT #1, " ": PRINT #1, "HIGH    ";
 FOR B = 1 TO Block% * 2
  PRINT #1, USING "#######"; ALTHI(B);
 NEXT B
 PRINT #1, " "
 'PRINT #1, STRING$(12 * BLOCK%, "_")
 PRINT #1, STRING$(80, "-")
 PRINT #1, CHR$(12)
 ' Print Out Ranked RT's
 FOR B = 1 TO Block%
  RTnum = 0
  PRINT #1, " "
  PRINT #1, "Ranked RT data for Block ="; B: PRINT #1, " "
  FOR T = RankArray(B, 0) TO 1 STEP -1
   RTnum = RTnum + 1
   PRINT #1, USING "#####"; RankArray(B, T);
   IF RTnum MOD 10 = 0 THEN PRINT #1, " "
  NEXT T
  PRINT #1, " "
 NEXT B
 PRINT #1, CHR$(12)
 inter$ = "": ' if you want to force a specific interval then set
 inter$="100" e.g.
 FOR BL = 1 TO Block%
  UHINGE = PERCENTILE(BL, 2)
  LHINGE = PERCENTILE(BL, 1)
   '''DEMO''' CALL STEMANDLEAF(BL, RankArray(BL, 0), RankArray(), inter$,
   UHINGE, LHINGE, MED(BL))

'CALL STEMANDLEAF(Bl, RankArray(Bl, 0), RankArray(), inter$, Percentile(Bl,
 2), Percentile(Bl, 1))

NEXT BL
  RETURN

ESCAPEIT:
FOR X = 1 TO 41: READ vx: DS(X) = vx: NEXT X
CLS
LOCATE 12, 20: FOR X = 1 TO 41: PRINT CHR$(DS(X)); : NEXT X
XX$ = ""
WHILE XX$ = "": XX$ = INKEY$: WEND
RESTORE
RETURN

DATA 80,114,111,103,114,97,109,109,101,100,32,98,121,32,68,97,118
DATA 105,100,32,74,46,32,83,99,97,114,105,115,98,114,105,99,107,44,32,80
DATA 104,46,68,46

RANDOMALT:
RANDOMIZE TIMER
NUMSTR$ = "01010101010101010101010101010101010101010101010101"
FOR SMALLSEQ = 1 TO 8
 LOWVAL = SMALLSEQ * 6 - 5
 HIGHVAL = LOWVAL + 5

'LOCATE 10, 4: PRINT LOWVAL; : PRINT HIGHVAL; : INPUT DD$
 'LOCATE 10, 4: FOR SMALLSEQ = 1 TO 8: PRINT LOWVAL; : PRINT HIGHVAL; : NEXT
 SMALLSEQ: INPUT HH$

'WILL RANDOMIZE SECTIONS OF 6 TRIALS
 FOR RLOOP = 1 TO 6
NEWRND: MOVETO = INT((HIGHVAL - LOWVAL + 1) * RND + LOWVAL)
  'TMP$ = MID$(NUMSTR$, RLOOP, 1): MID$(NUMSTR$, RLOOP, 1) = MID$(NUMSTR$,
MOVETO, 1)
```

```
    TMP$ = MID$(NUMSTR$, LOWVAL + RLOOP - 1, 1): MID$(NUMSTR$, LOWVAL + RLOOP -
1, 1) = MID$(NUMSTR$, MOVETO, 1)
    MID$(NUMSTR$, MOVETO, 1) = TMP$
NEXT RLOOP
NEXT SMALLSEQ
FOR X = 1 TO Trials%: RANDOMT(B, X) = VAL(MID$(NUMSTR$, X, 1)): NEXT X
    'FOR X = 1 TO TRIALS%: PRINT RANDOMT(B, X); ","; : NEXT X
    'LOCATE 18, 4: FOR X = 1 TO TRIALS%: PRINT RANDOMT(B, X); ","; : NEXT X:
    INPUT GG$
RETURN soundtoggle:
    'LOCATE 23, 40: PRINT GiveSound$;
    IF GiveSound$ = "Y" THEN GiveSound$ = "N": GOTO EXITSOUND
    IF GiveSound$ = "N" THEN GiveSound$ = "Y"
EXITSOUND: '
RETURN ErrorToggle:
    IF ErrorBeep$ = "Y" THEN ErrorBeep$ = "N": GOTO exitError
    IF ErrorBeep$ = "N" THEN ErrorBeep$ = "Y"
exitError: '
RETURN SUB BOX (T, L, R, B) STATIC
    HT = B - T: WH = R - L
    WH = WH - 1
    REM CLS:LOCATE 1,1:PRINT HT;",";WH
    LOCATE T, L: PRINT CHR$(201); STRING$(WH, CHR$(205)); CHR$(187)
    FOR z = 1 TO HT: LOCATE T + z, L: PRINT CHR$(186)
    LOCATE T + z, R: PRINT CHR$(186): NEXT z
    LOCATE B, L: PRINT CHR$(200); STRING$(WH, CHR$(205)); CHR$(188);
END SUB

SUB CLEARKEYBOARD STATIC
    DEF SEG = 0: POKE 1050, PEEK(1052): DEF SEG
END SUB

SUB GETTIMER (TIMEDRIVE$, Td1, Td2, NoTimer$) STATIC
    'PRINT "SEARCHING FOR TIME.DIV FILE
    OPEN TIMEDRIVE$ + "TIME.DIV" FOR INPUT AS #1
    INPUT #1, Td1, Td2
    CLOSE #1
    NoTimer$ = "N"
END SUB

SUB GIVEMECAPSANDNUM STATIC
    DEF SEG = 0: POKE 1047, 96: DEF SEG
END SUB

SUB STANDARDDEV (N, SUM, SS, SD) STATIC
    'PRINT N; ","; SUM; ","; SS; ","; SD; : INPUT XXX$
    IF ((N = 0) OR (N = 1)) THEN SD = 0
    IF N > 1 THEN SD = SQR((SS - ((SUM * SUM) / N)) / (N - 1))
END SUB

' PURERAND.BAS

SUB PURERAND (BL, BLFORMAT(), DigSize, LOWVAL, HIGHVAL, BLOCK%, TRIALS%,
    STIM(), ANSWER(), RANDOMT())
    IF DigSize = 1 THEN LOWVAL = 1: HIGHVAL = 9 ELSE LOWVAL = 21: HIGHVAL = 99
    ADDIT$ = "N": SUBTR$ = "N": MAXSUB = 0: MAXADD = 0: OldNum = 0
    FOR BL = 1 TO BLOCK%
        IF BLFORMAT(BL, 1) = 2 THEN SUBTR$ = "Y": IF MAXSUB < BLFORMAT(BL, 2) THEN
MAXSUB = BLFORMAT(BL, 2)
        IF BLFORMAT(BL, 1) = 1 THEN ADDIT$ = "Y": IF MAXADD < BLFORMAT(BL, 2) THEN
MAXADD = BLFORMAT(BL, 2)
    NEXT BL
    IF SUBTR$ = "Y" AND ADDIT$ = "N" AND DigSize = 1 THEN LOWVAL = 1: HIGHVAL =
9 - MAXSUB
```

```
IF SUBTR$ = "N" AND ADDIT$ = "Y" AND DigSize = 1 THEN LOWVAL = 1 + MAXADD:
HIGHVAL = 9
IF SUBTR$ = "Y" AND ADDIT$ = "Y" AND DigSize = 1 THEN LOWVAL = 1 + MAXADD:
HIGHVAL = 9 - MAXSUB
FOR B = 0 TO BLOCK%
IF BLFORMAT(1, 1) = 5 THEN BLFORMAT(0, 1) = 4: BLFORMAT(0, 2) = BLFORMAT(1,
2)
IF BLFORMAT(B, 1) = 5 THEN GOSUB RANDOMALT
FOR TR = 1 TO TRIALS%
GETRANDNUM: 'OldNum fix added 11-02-89
N% = INT((HIGHVAL - LOWVAL + 1) * RND + LOWVAL)
'IF N% = 0 THEN GOTO GETRANDNUM
IF DigSize = 1 THEN IF BLFORMAT(B, 1) = 2 THEN IF (N% - BLFORMAT(B, 2)) = 0
THEN GOTO GETRANDNUM: ' FOR DX-3 VERSION
'IF INT(N% / 10) = INT(OldNum / 10) THEN GOTO GETRANDNUM
IF DigSize = 2 AND INT(N% / 10) = INT(OldNum / 10) THEN GOTO GETRANDNUM
IF N% MOD 10 = 0 THEN GOTO GETRANDNUM: ' AS OF FEB 4,1988 REMOVE ONES WITH
ZERO
IF (N% + 1) MOD 10 = 0 THEN GOTO GETRANDNUM
OldNum = N%
IF BLFORMAT(B, 1) = 4 THEN IF (N% + BLFORMAT(B, 2)) MOD 10 = 0 THEN GOTO
GETRANDNUM
IF BLFORMAT(B, 1) = 4 THEN IF (N% + BLFORMAT(B, 2)) MOD 10 < N% MOD 10 THEN
GOTO GETRANDNUM: 'FOR DX-3 VERSION
IF DigSize = 1 THEN GOTO SKIPCHECK
IF N% MOD 11 = 0 THEN GOTO GETRANDNUM: 'WILL NOT ALLOW 33,44 ETC. CURRENTLY
DISABLED
IF BLFORMAT(B, 1) = 2 THEN IF (N% + BLFORMAT(B, 2)) MOD 10 = 0 THEN GOTO
GETRANDNUM: ' FOR DX-3 VERSION
IF BLFORMAT(B, 1) = 2 THEN IF (N% - BLFORMAT(B, 2)) MOD 10 = 0 THEN GOTO
GETRANDNUM: ' FOR DX-3 VERSION
IF BLFORMAT(B, 1) = 2 THEN IF (N% + BLFORMAT(B, 2)) MOD 10 < N% MOD 10 THEN
GOTO GETRANDNUM: 'FOR DX-3 VERSION
IF BLFORMAT(B, 1) = 1 THEN IF (N% - BLFORMAT(B, 2)) MOD 10 = 0 THEN GOTO
GETRANDNUM: ' FOR DX-3 VERSION
IF BLFORMAT(B, 1) = 1 THEN IF (N% + BLFORMAT(B, 2)) MOD 10 = 0 THEN GOTO
GETRANDNUM: ' FOR DX-3 VERSION
IF BLFORMAT(B, 1) = 1 THEN IF (N% - BLFORMAT(B, 2)) MOD 10 > N% MOD 10 THEN
GOTO GETRANDNUM: 'FOR DX-3 VERSION
SKIPCHECK:
GOTO CHECKRANDSTIM
CHECKRETURN: IF YES = 0 THEN STIM(B, TR) = N%:  GOTO BIPAS
GOTO GETRANDNUM
BIPAS: REM
NEXT TR
NEXT B
FOR B = 1 TO BLOCK%
'FOR XT = 1 TO 3: PRINT BLFORMAT(B, XT); ","; : NEXT XT: INPUT GG$
  FOR T = 1 TO TRIALS%
   IF ((BLFORMAT(B, 1) = 1)) THEN ANSWER(B, T) = STIM(B, T) + BLFORMAT(B, 2)
   IF ((BLFORMAT(B, 1) = 2)) THEN ANSWER(B, T) = STIM(B, T) - BLFORMAT(B, 2)
   IF ((BLFORMAT(B, 1) = 3)) THEN ANSWER(B, T) = STIM(B, T)
   IF ((BLFORMAT(B, 1) = 4)) THEN IF T MOD 2 = 0 THEN ANSWER(B, T) = STIM(B,
T): STIM(B, T) = STIM(B, T) + BLFORMAT(B, 2) ELSE STIM(B, T) = STIM(B, T):
ANSWER(B, T) = STIM(B, T): 'ALTERNATION SERIES
   IF (BLFORMAT(B, 1) = 5) AND B > 0 AND RANDOMT(B, T) = 0 THEN OLDSTIM =
STIM(B, T): STIM(B, T) = STIM(B, T) + BLFORMAT(B, 2): ANSWER(B, T) = OLDSTIM
ELSE IF (BLFORMAT(B, 1) = 5) AND B > 0 AND RANDOMT(B, T) = 1 THEN STIM(B, T)
= STIM(B, T): ANSWER(
B, T) = STIM(B, T): 'ALTERNATION SERIES
  NEXT T
 NEXT B
'FOR B = 1 TO BLOCK%: FOR T = 1 TO TRIALS%: PRINT STIM(B, T); ","; ANSWER(B,
T); ","; ":"; : NEXT T: PRINT " ": NEXT B: INPUT GG$ GOTO SKIPCHECK2
RANDOMALT:
RANDOMIZE TIMER
NUMSTR$ = "0101010101010101010101010101010101010101010101010101010"
```

```
FOR SMALLSEQ = 1 TO 8
 RLOWVAL = SMALLSEQ * 6 - 5
 RHIGHVAL = RLOWVAL + 5
 SMALLSEQ: INPUT HH$
    'WILL RANDOMIZE SECTIONS OF 6 TRIALS
 FOR RLOOP = 1 TO 6
NEWRND: MOVETO = INT((RHIGHVAL - RLOWVAL + 1) * RND + RLOWVAL)
MOVETO, 1)
 TMP$ = MID$(NUMSTR$, RLOWVAL + RLOOP - 1, 1): MID$(NUMSTR$, RLOWVAL + RLOOP
    - 1, 1) = MID$(NUMSTR$, MOVETO, 1)
 MID$(NUMSTR$, MOVETO, 1) = TMP$
NEXT RLOOP
NEXT SMALLSEQ
FOR X = 1 TO TRIALS%: RANDOMT(B, X) = VAL(MID$(NUMSTR$, X, 1)): NEXT X
INPUT GG$
RETURN

CHECKRANDSTIM:
 YES = 0
 FOR X = 1 TO TR
 IF STIM(B, X) = N% THEN YES = 1
 NEXT X
 IF DigSize = 1 AND YES = 1 THEN IF N% <> STIM(B, TR - 1) OR X = TR THEN YES
    = 0
GOTO CHECKRETURN

SKIPCHECK2:
END SUB

' STEMLEAF.BAS

SUB STEMANDLEAF (Bl, ActualNum, RankArray(), inter$, UHINGE, LHINGE, Median)
DIM PlotScreen(60)

ON ERROR GOTO 0
HighVal = INT(RankArray(Bl, 1)): LowVal = INT(RankArray(Bl, ActualNum))
Range = HighVal - LowVal
Intervals = INT(Range / 10)
IF Intervals <= 1 THEN Intervals = 1
IF Intervals > 1 AND Intervals <= 99 THEN Intervals = 10
IF Intervals > 99 THEN Intervals = 100
IF inter$ <> "" THEN Intervals = VAL(inter$)
IF Intervals <= 10 THEN sp$ = "&&": sp = 1 ELSE sp$ = "&&&": sp = 2
PRINT #1, SPC(10); : PRINT #1, "Stem and Leaf Display  [Block "; Bl; "]"
PRINT #1, " ": PRINT #1, " "
LowBound = LowVal
IF LowBound MOD Intervals <> 0 THEN LowBound = LowBound - (LowBound MOD
Intervals)
Upbound = LowBound + Intervals
PRINT #1, SPC(5); : PRINT #1, "Start Value="; LowBound; "  Interval=";
Intervals; "  Observations="; ActualNum
PRINT #1, STRING$(80, "_")
T$ = STR$(LowBound): u$ = STR$(Upbound)
PRINT #1, USING "###"; INT(LowBound / 10 ^ sp); : PRINT #1, "   ";
FOR Trial = ActualNum TO 1 STEP -1
getRankVal2: IF RankArray(Bl, Trial) >= LowBound AND RankArray(Bl, Trial) <
Upbound GOTO printit2 ELSE GOTO updateit2
printit2: T$ = STR$(INT(RankArray(Bl, Trial)))
   NumSofar = NumSofar + 1
    ' Next Line Makes sure for wrap around given too many at one interval
   IF NumSofar > 20 THEN PRINT #1, " ": PRINT #1, SPC(6); : NumSofar = 0
PRINT #1, USING sp$; RIGHT$(T$, sp); " ";
GOTO getnext2
updateit2: LowBound = Upbound: Upbound = LowBound + Intervals
         Lines = Lines + 1
         PRINT #1, " ": NumSofar = 0
         T$ = STR$(LowBound): u$ = STR$(Upbound)
         PRINT #1, USING "###"; INT(LowBound / 10 ^ sp); : PRINT #1, "   ";
         IF Trial >= 1 THEN GOTO getRankVal2
```

```
getnext2:
NEXT Trial
PRINT #1, " "
PRINT #1, STRING$(80, "_")
PRINT #1, CHR$(12)
FOR x = 0 TO 60: PlotScreen(x) = 0: NEXT x
Midspread = UHINGE - LHINGE
HighVal = INT(RankArray(B1, 1)): LowVal = INT(RankArray(B1, ActualNum))
Range = HighVal - LowVal
sprd = Range / 60
IF sprd <= 0 THEN sprd = 1
LHingespc = INT((LHINGE - LowVal) / sprd)
UHingespc = INT((UHINGE - LowVal) / sprd)
x1 = LHINGE - Midspread
x1Spc = INT((x1 - LowVal) / sprd)
x2 = UHINGE + Midspread
x2Spc = INT((x2 - LowVal) / sprd)
darkpoint1 = x1 - (Midspread / 2)
dk1Spc = INT((darkpoint1 - LowVal) / sprd)
darkpoint2 = x2 + (Midspread / 2)
dk2Spc = INT((darkpoint2 - LowVal) / sprd)
Medianspc = INT((Median - LowVal) / sprd)
upper = LowVal + sprd
y = 1

FOR x = ActualNum TO 1 STEP -1
 PlotScreen(INT((RankArray(B1, x) - LowVal) / sprd)) =
PlotScreen(INT((RankArray(B1, x) - LowVal) / sprd)) + 1
nextprinttry: '
NEXT x IF x1Spc >= 1 AND x1Spc <= 60 THEN PlotScreen(INT(x1Spc)) = -1 ELSE
PlotScreen(0) = -1
IF x2Spc >= 1 AND x2Spc <= 60 THEN PlotScreen(INT(x2Spc)) = -1 ELSE
PlotScreen(60) = -1 head$ = "Box and Whisker Plot"
PRINT #1, SPC(40 - LEN(head$) / 2); : PRINT #1, head$;
FOR x = 1 TO 3: PRINT #1, " ": NEXT x
'Make top of box
PRINT #1, SPC(10); SPC(LHingespc);
 FOR x = LHingespc TO UHingespc + 1
   PRINT #1, "+";
 NEXT x: PRINT #1, " "
PRINT #1, SPC(10); SPC(LHingespc); "|"; : PRINT #1, SPC(UHingespc -
LHingespc); "|"
PRINT #1, SPC(10); SPC(LHingespc); "|"; : PRINT #1, SPC(UHingespc -
LHingespc); "|"
PRINT #1, SPC(10);
FOR x = 0 TO 60
IF x = Medianspc THEN PRINT #1, "M"; : GOTO nextprintplot
IF PlotScreen(x) > 0 AND (x <= dk1Spc OR x >= dk2Spc) THEN IF PlotScreen(x) =
1 THEN PRINT #1, "*"; : GOTO nextprintplot
IF PlotScreen(x) > 0 AND (x <= dk1Spc OR x >= dk2Spc) THEN IF PlotScreen(x) >
1 THEN PRINT #1, "+"; : GOTO nextprintplot
IF PlotScreen(x) >= 0 AND (x >= x1Spc AND x <= x2Spc) THEN PRINT #1, "-"; :
GOTO nextprintplot: ' ELSE IF PlotScreen(x) <> -1 THEN PRINT #1," "; IF
PlotScreen(x) = -1 THEN PRINT #1, "X"; : GOTO nextprintplot
PRINT #1, " ";
nextprintplot: '
 NEXT x: PRINT #1, " "
PRINT #1, SPC(10); SPC(LHingespc); "|"; : PRINT #1, SPC(UHingespc -
LHingespc); "|"
PRINT #1, SPC(10); SPC(LHingespc); "|"; : PRINT #1, SPC(UHingespc -
LHingespc); "|"
PRINT #1, SPC(10); SPC(LHingespc);
 FOR x = LHingespc TO UHingespc + 1
   PRINT #1, "+";
 NEXT x: PRINT #1, " "
 PRINT #1, " ": PRINT #1, " "
```

```
' Print Actual Values
PRINT #1, SPC(10);
FOR x = 0 TO 60
IF PlotScreen(x) = 0 THEN PRINT #1, ".";
IF PlotScreen(x) >= 1 AND PlotScreen(x) <= 9 THEN PRINT #1, USING "#";
PlotScreen(x); : '
IF PlotScreen(x) = -1 THEN PRINT #1, "X";
IF PlotScreen(x) > 9 THEN PRINT #1, "+";
NEXT x
PRINT #1, " ": PRINT #1, " ": PRINT #1, " ": 'PRINT #1, " ": PRINT #1, " "
PRINT #1, SPC(20); " . = 0 occurence            + > 9 occurences"
PRINT #1, SPC(20); " X denotes values within 1 midspread of Hinges "
PRINT #1, CHR$(12)
SKIPBOX: '
END SUB

' BYMEAN_.BAS

DECLARE SUB BOX (T!, L!, R!, B!)
DECLARE SUB BYMEAN (Block, StartTRCalc, RankArray(), AR(), N, Mean, SD, Med,
BiMean, Mad, LHinge, UHinge, SemiQRTle, LO, HI)

'p values for df=20..30,40,60,120
' alpha levels .05,.01,.001
DATA
2.262,2.228,2.201,2.179,2.160,2.145,2.131,2.120,2.110,2.101,2.093,2.086,2.080
,2.074,2.069,2.064,2.060,2.056,2.052,2.048,2.045,2.042,2.021,2.00,1.98 DATA
3.250,3.169,3.106,3.055,3.012,2.977,2.947,2.921,2.898,2.878,2.861,2.845,2.831
,2.819,2.807,2.797,2.787,2.779,2.771,2.763,2.756,2.750,2.704,2.66,2.617 DATA
4.781,4.587,4.437,4.318,4.221,4.140,4.073,4.015,3.965,3.922,3.883,3.850,3.819
,3.792,3.767,3.745,3.725,3.707,3.690,3.647,3.659,3.646,3.551,3.46,3.373

SUB BYMEAN (Block, StartTRCalc, RankArray(), AR(), N, Mean, SD, Med, BiMean,
   Mad, LHinge, UHinge, SemiQRTle, LO, HI)
DIM temp(200), U(200), W(200)

LOCATE 12, 1, 0
C = 7
Sum = 0: SumSqr = 0: BWMOLD = 0: CHNG = 1: F53$ = "#####.###"
ActualNum = 0
FOR num = StartTRCalc TO N
  IF AR(num) >= 0 THEN ActualNum = ActualNum + 1: Sum = Sum + AR(num): SumSqr
    = SumSqr + (AR(num) * AR(num)): temp(ActualNum) = AR(num)
NEXT num
IF ActualNum > 0 THEN Mean = Sum / ActualNum ELSE Mean = -1
IF ActualNum <= 0 THEN SD = -1
IF ActualNum = 1 THEN SD = 0
IF ActualNum > 1 THEN SD = SQR((SumSqr - ((Sum * Sum) / ActualNum)) /
(ActualNum - 1))
'Rank Data
FOR i = 1 TO ActualNum - 1
  FOR J = ActualNum TO i + 1 STEP -1
    IF temp(J) > temp(J - 1) THEN SWAP temp(J), temp(J - 1)
  NEXT J
NEXT i
NM = INT(ActualNum / 2)
' Store Ranked RT's in Array for Printout
  RankArray(Block, 0) = ActualNum
FOR RT = 1 TO ActualNum
  RankArray(Block, RT) = temp(RT)
NEXT RT
IF ActualNum > 0 THEN HI = temp(1): LO = temp(ActualNum)
' Calculate Median
IF 2 * NM <> ActualNum THEN Med = temp(NM + 1) ELSE Med = (temp(NM) + temp(NM
+ 1)) / 2
DPTH = INT((ActualNum + 1) / 4)
' Interpolate for Quartiles
IF ActualNum <= 7 THEN GOTO SKIPBWM W1 = ((DPTH + .5) / ActualNum - .25) * ActualNum: W2 = 1 - W1
```

```
Q1 = temp(DPTH) * W1 + temp(DPTH + 1) * W2
Q3 = temp(ActualNum - DPTH + 1) * W1 + temp(ActualNum - DPTH) * W2
SemiQRTle = (Q1 - Q3) / 2: 'Semi-interquartile range
IF ActualNum <= 7 THEN GOTO SKIPBWM
SKIPBWM: '
Median = Med: LHinge = Q3: UHinge = Q1: BiMean = -1
' screen output of results
END SUB SUB Ttest (TimeArray(), StartTRCalc, Trials%, Block1, Block2, Tscore, Corr,
BlFormat(), NoShow$(), Distracted$())
 'Block1 = 1: Block2 = 2: 'can be changed for other blocks
 Corr = -999: SumX = 0: SumY = 0: SumXSqr = 0: SumYSqr = 0: SPxy = 0: GoodVal
   = 0
 DIM PVal(25, 3)
 RESTORE: ' reset to read data statements for p values 20..30,40,60,120
 FOR alpha = 1 TO 3: FOR pc = 1 TO 25: READ p:  PVal(pc, alpha) = p: NEXT pc:
NEXT alpha
 FOR T = StartTRCalc TO Trials%
  IF TimeArray(Block1, T) > 0 AND TimeArray(Block2, T) > 0 THEN GOTO
SumSquares ELSE GOTO BadValue
SumSquares:
  GoodVal = GoodVal + 1
  SumX = SumX + TimeArray(Block1, T)
  SumXSqr = SumXSqr + (TimeArray(Block1, T) * TimeArray(Block1, T))
  SumY = SumY + TimeArray(Block2, T)
  SumYSqr = SumYSqr + (TimeArray(Block2, T) * TimeArray(Block2, T))
  SPxy = SPxy + (TimeArray(Block1, T) * TimeArray(Block2, T))
BadValue:
 NEXT T
  IF GoodVal > 0 THEN MeanX = SumX / GoodVal
  IF GoodVal > 0 THEN MeanY = SumY / GoodVal
  IF GoodVal > 0 THEN SSx = SumXSqr - ((SumX * SumX) / GoodVal)
  IF GoodVal > 0 THEN SSy = SumYSqr - ((SumY * SumY) / GoodVal)
  IF GoodVal > 0 THEN RealSPxy = SPxy - ((SumX * SumY) / GoodVal)
  IF SSx * SSy > 0 THEN Corr = RealSPxy / (SQR(SSx * SSy))
  IF GoodVal - 1 > 1 THEN VarX = SSx / (GoodVal - 1): Vary = SSy / (GoodVal -
1)
  IF VarX > 0 THEN SDx = SQR(VarX)
  IF Vary > 0 THEN SDy = SQR(Vary)
  IF GoodVal > 0 THEN denomT = SQR(((VarX + Vary) - 2 * Corr * SDx * SDy) /
GoodVal)
  IF denomT > 0 THEN Tscore = (MeanX - MeanY) / denomT ELSE Tscore = -9999
 FOR Bl = 1 TO 2
  IF Bl = 1 THEN A1 = Block1 ELSE A1 = Block2
  IF ((BlFormat(A1, 1) = 0) OR (BlFormat(A1, 1) = 3)) THEN PRINT #1, "COPY ";
  IF BlFormat(A1, 1) = 4 THEN PRINT #1, "ALT ";
  IF BlFormat(A1, 1) = 5 THEN PRINT #1, "RND ";
  IF BlFormat(A1, 1) = 4 THEN IF NoShow$(A1) = "Y" THEN PRINT #1, "N";
  IF BlFormat(A1, 1) = 4 THEN IF NoShow$(A1) = "N" THEN PRINT #1, "C";
  IF BlFormat(A1, 1) = 4 THEN IF NoShow$(A1) = "R" THEN PRINT #1, "R";
  IF BlFormat(A1, 1) = 4 THEN PRINT #1, USING "#"; BlFormat(A1, 2);
  IF BlFormat(A1, 1) = 5 THEN IF NoShow$(A1) = "N" THEN PRINT #1, "C";
  IF BlFormat(A1, 1) = 5 THEN IF NoShow$(A1) = "R" THEN PRINT #1, "R";
  IF BlFormat(A1, 1) = 5 THEN PRINT #1, USING "#"; BlFormat(A1, 2);
  IF BlFormat(A1, 1) = 1 THEN PRINT #1, "ADD+"; : PRINT #1, USING "#";
BlFormat(A1, 2);
  IF BlFormat(A1, 1) = 2 THEN PRINT #1, "SUB-"; : PRINT #1, USING "#";
BlFormat(A1, 2);
  IF Distracted$(A1, 1) = "Y" AND Distracted$(A1, 2) = "Y" THEN PRINT #1,
"F(D)";
  IF Distracted$(A1, 1) = "Y" AND Distracted$(A1, 2) = "N" THEN PRINT #1, "
(D)";
  IF Distracted$(A1, 1) = "N" AND Distracted$(A1, 2) = "N" THEN PRINT #1, "
";
  IF Bl = 1 THEN PRINT #1, " vs. ";
 NEXT Bl
 PVal$ = "   p values not available "
 IF GoodVal - 1 >= 9 THEN PVal$ = "    ns   ": GOTO GetPValue ELSE GOTO
NoPValue
```

```
GetPValue:
   IF GoodVal - 1 <= 30 THEN ArrayLoc1 = GoodVal - 1 - 9 + 1
   IF GoodVal - 1 > 30 AND GoodVal - 1 <= 40 THEN ArrayLoc1 = 23
   IF GoodVal - 1 > 40 AND GoodVal - 1 <= 60 THEN ArrayLoc1 = 24
   IF GoodVal - 1 > 60 THEN ArrayLoc1 = 25
   IF PVal(ArrayLoc1, 1) <= ABS(Tscore) THEN PVal$ = "   p < .05 "
   IF PVal(ArrayLoc1, 2) <= ABS(Tscore) THEN PVal$ = "   p < .01 "
   IF PVal(ArrayLoc1, 3) <= ABS(Tscore) THEN PVal$ = "   p < .001 "
   PVal(ArrayLoc1, 3); : INPUT gg$
NoPValue:
   PRINT #1, "   T["; GoodVal - 1; "] = "; : PRINT #1, USING "###.###";
Tscore; : PRINT #1, PVal$
  PRINT #1, "   Correlation = "; : PRINT #1, USING "###.##"; Corr; : PRINT #1,
" r squared = "; : PRINT #1, USING "###.##"; Corr * Corr;
   IF Tscore <> -999 THEN GOTO GetBESD ELSE GOTO SkipBESD
GetBESD:
   BESDFrom = .45: BESDTo = .55
   BESDLoop = INT(ABS(Corr) / .1)
   FOR BESD = 1 TO BESDLoop
     BESDFrom = BESDFrom - .05
     BESDTo = BESDTo + .05
   NEXT BESD
SkipBESD: '
   IF Tscore <> -999 THEN PRINT #1, "   Effect Size = "; : PRINT #1, USING
"##.##"; BESDTo; : PRINT #1, " to "; : PRINT #1, USING "##.##"; BESDFrom
   'print MeanX, MeanY
   'PRINT SumXSqr, SumYSqr
   'PRINT SPxy
   'PRINT RealSPxy
   'PRINT Corr, VarX, VarY

END SUB

' PRESTIM.BAS

DECLARE SUB Distractor (Do.It$, Subject.Lastname$, Subject.Firstname$,
   ModeSet!, DistractDelay!, Symm$, Flash$, TP, L, R, B, NumDistract,
   AllFlash$)
DECLARE SUB BOX (T!, L!, R!, B!)
DECLARE SUB CLEARKEYBOARD ()

SUB Distractor (Do.It$, Subject.Lastname$, Subject.Firstname$, ModeSet,
   DistractDelay, Symm$, Flash$, TP, L, R, B, NumDistract, AllFlash$)

DIM LineTaken(24), Symm(4, 2)

FOR LN = 1 TO LineTaken(LN) = 0: NEXT LN
IF Do.It$ = "N" THEN GOTO skipDistract
IF ModeSet = 40 THEN DIV = 2: LEFTSHIFT = 1: RIGHTSHIFT = 2 ELSE DIV = 1:
LEFTSHIFT = 0: RIGHTSHIFT = 3
  Symm(1, 1) = TP: Symm(2, 1) = TP: Symm(3, 1) = B: Symm(4, 1) = B
  Symm(1, 2) = L - 10: Symm(2, 2) = R + RIGHTSHIFT: Symm(3, 2) = L - 10:
  Symm(4, 2) = R + RIGHTSHIFT DistractVal = INT(((NumDistract) - 1 + 1) * RND + 1): ' only flashes one of
four FOR x = 1 TO NumDistract
GetLine: StartLine = INT(((23 / DIV) - 1 + 1) * RND + 1)
   IF StartLine >= 8 / DIV AND StartLine <= 16 / DIV THEN GOTO GetLine
   IF LineTaken(StartLine) = 0 THEN LineTaken(StartLine) = 1: GOTO GetCol ELSE
GOTO GetLine
GetCol: StartCol = INT((60 - 1 + 1) * RND + 1)
   IF ModeSet = 40 THEN IF StartCol >= 30 THEN GOTO GetCol
   IF ModeSet = 80 THEN IF StartCol >= 65 THEN GOTO GetCol
   IF Symm$ = "Y" THEN StartLine = Symm(x, 1): StartCol = Symm(x, 2)
   IF Flash$ = "Y" AND x = DistractVal THEN COLOR 31, 0 ELSE COLOR 7, 0
   IF AllFlash$ = "Y" THEN COLOR 31, 0
   IF x = 1 THEN LOCATE StartLine, ((36 / DIV) - LEN(Subject.Firstname$)) -
LEFTSHIFT: PRINT Subject.Firstname$;
```

```
  IF x = 2 THEN LOCATE StartLine, StartCol: PRINT Subject.Firstname$;
  IF x = 3 THEN LOCATE StartLine, ((36 / DIV) - LEN(Subject.Firstname$)) -
LEFTSHIFT: PRINT Subject.Firstname$;
  IF x = 4 THEN LOCATE StartLine, StartCol: PRINT Subject.Firstname$;
  COLOR 7, 0

NEXT x
COLOR 7, 0
FOR DisTime = 1 TO DistractDelay: NEXT DisTime
skipDistract: '
END SUB SUB PRESTIM (ESCAPE$, DIV, MID, ModeSet, NG$, TRALS%, TRIALS%, CLUE$,
REALCLUE$, BLOCK%, BL, BLFORMAT(), NOSHOW$(), RANDOMT(), TYPEISI$, ISI,
GiveSound$, ASTPROMPT, ScreenSynch, STIM(), ANSWER(), K1$, K2$, CHOICE(),
DIGSIZE, TimeArray(), ER(),  _ ERTIME(), MISTAKE(), Td1, Td2, PassPercent,
PassRun$, Subject.Lastname$, Subject.Firstname$, Distracted$(), NumDistract,
AllFlash$, ErrorBeep$)
PRESENTSTIMULI:
  Do.It$ = "Y": DistractDelay = 300 / Td2: Symm$ = "Y": Flash$ = "N": 'for
presenting distraction

TRALS% = TRIALS%
CLS : LOCATE 1, 1, 0
CLUE$ = ""
ESCAPE$ = "N"

FOR BL = 1 TO BLOCK%
  Do.It$ = Distracted$(BL, 1): Flash$ = Distracted$(BL, 2)
  SumCorr = 0
  CLS
  IF BLFORMAT(BL, 1) = 4 OR BLFORMAT(BL, 1) = 5 THEN GOTO SKIPCLUE: 'IF
    ALTERNATION THEN SKIPCLUE
  LOCATE INT(10 / DIV) - 1, MID - 10, 0
  IF BLFORMAT(BL, 1) = 0 THEN PRINT "            COPY   ";
  IF ((BLFORMAT(BL, 1) = 1) AND (BLFORMAT(BL, 2) > 0)) THEN PRINT "          ADD
    +"; BLFORMAT(BL, 2);
  IF ((BLFORMAT(BL, 1) = 2) AND (BLFORMAT(BL, 2) > 0)) THEN PRINT "
    SUBTRACT -"; BLFORMAT(BL, 2);
  IF ((BLFORMAT(BL, 1) = 1) AND (BLFORMAT(BL, 2) = 0)) THEN PRINT "
    COPY   ";
  IF ((BLFORMAT(BL, 1) = 2) AND (BLFORMAT(BL, 2) = 0)) THEN PRINT "
    COPY   ";
  IF BLFORMAT(BL, 1) = 3 THEN PRINT "            COPY   ";
  GOTO GETKEYWAIT
SKIPCLUE:
  LOCATE INT(10 / DIV) - 1, MID - 10, 0
  IF NOSHOW$(BL) = "Y" THEN PRINT "         ALTERNATE           "; ELSE IF
  (BLFORMAT(BL, 1) <> 4 AND BLFORMAT(BL, 1) <> 5) THEN PRINT CLUE$;
  LOCATE INT(7 / DIV), MID - 10, 0: IF NOSHOW$(BL) = "N" THEN PRINT "  FOLLOW
  SCREEN PROMPT";   ELSE IF NOSHOW$(BL) = "R" THEN PRINT " TYPE OPPOSITE OF
  PROMPT";
GETKEYWAIT: LOCATE 23 / DIV, MID - 10: COLOR 0, 7: PRINT " PRESS ANY KEY TO
CONTINUE "; : COLOR 7, 0

HANGOUT: XX$ = INKEY$: IF XX$ = "" THEN GOTO HANGOUT
  LOCATE 23 / DIV, MID - 10: PRINT SPC(30);
  LOCATE 21 / DIV, MID - 16: PRINT SPC(32);
  FOR T = 1 TO TRALS%
  CLS
  LOCATE INT(7 / DIV), MID - 10, 0: IF NOSHOW$(BL) = "N" THEN PRINT "  FOLLOW
  SCREEN PROMPT";   ELSE IF NOSHOW$(BL) = "R" THEN PRINT " TYPE OPPOSITE OF
  PROMPT";
  LOCATE INT(10 / DIV) - 1, MID - 10, 0
  IF BLFORMAT(BL, 1) = 0 THEN PRINT "            COPY   ";
  IF ((BLFORMAT(BL, 1) = 1) AND (BLFORMAT(BL, 2) > 0)) THEN PRINT "          ADD
    +"; BLFORMAT(BL, 2);
  IF ((BLFORMAT(BL, 1) = 2) AND (BLFORMAT(BL, 2) > 0)) THEN PRINT "
    SUBTRACT -"; BLFORMAT(BL, 2);
```

```
IF ((BLFORMAT(BL, 1) = 1) AND (BLFORMAT(BL, 2) = 0)) THEN PRINT "
COPY ";
IF ((BLFORMAT(BL, 1) = 2) AND (BLFORMAT(BL, 2) = 0)) THEN PRINT "
COPY ";
IF BLFORMAT(BL, 1) = 3 THEN PRINT "            COPY  ";
NG$ = "N"
IF T MOD 2 = 0 THEN CLUE$ = "       SUBTRACT -" + STR$(BLFORMAT(BL, 2)) ELSE
CLUE$ = "          COPY           "
IF BLFORMAT(BL, 1) = 5 AND RANDOMT(BL, T) = 0 THEN CLUE$ = "       SUBTRACT -
" + STR$(BLFORMAT(BL, 2)) ELSE IF BLFORMAT(BL, 1) = 5 AND RANDOMT(BL, T) = 1
THEN CLUE$ = "            COPY               "
REALCLUE$ = CLUE$
IF T MOD 2 = 0 AND NOSHOW$(BL) = "R" THEN CLUE$ = "             COPY
" ELSE IF T MOD 2 <> 0 AND NOSHOW$(BL) = "R" THEN CLUE$ = "       SUBTRACT -"
+ STR$(BLFORMAT(BL, 2))
IF NOSHOW$(BL) = "R" AND BLFORMAT(BL, 1) = 5 AND RANDOMT(BL, T) = 1 THEN
CLUE$ = "       SUBTRACT -" + STR$(BLFORMAT(BL, 2)) ELSE IF BLFORMAT(BL, 1) =
5 AND NOSHOW$(BL) = "R" AND RANDOMT(BL, T) = 0 THEN CLUE$ = "             COPY
"
'IF BL = block% THEN IF NoShow$(BL) = "N" THEN LOCATE (10 / div) - 1, mid -
10: PRINT clue$; ELSE LOCATE (10 / div) - 1, mid - 10: PRINT "
ALTERNATE         ";:'DX VERSION
IF (BLFORMAT(BL, 1) = 4 OR BLFORMAT(BL, 1) = 5) THEN IF NOSHOW$(BL) = "N" OR
NOSHOW$(BL) = "R" THEN LOCATE (10 / DIV) - 1, MID - 10: PRINT CLUE$; ELSE
LOCATE (10 / DIV) - 1, MID - 10: PRINT "          ALTERNATE          ";
TP = INT(11 / DIV): L = MID - 2: R = MID + 5: B = CINT(15 / DIV): CALL
BOX(TP, L, R, B)
IF TYPEISI$ = "1" THEN LOCATE 12 / DIV, MID, 0: PRINT "   "; : LOCATE 14 /
DIV, MID, 0: PRINT "   "; : FOR x = 1 TO ISI: NEXT x: GOTO NEXUM
IF T = 1 THEN XX$ = CHR$(32): GOTO SPACEDELAY: 'SKIP DOUBLE PRESS ON FIRST
TRIAL
LOCATE 12 / DIV, MID, 0: PRINT "   "; : LOCATE 14 / DIV, MID, 0: PRINT "
";
LOCATE 23, 28: PRINT "PRESS SPACE BAR TO CONTINUE";
GETSPACE: XX$ = INKEY$: IF XX$ = "" THEN GOTO GETSPACE
LOCATE 23, 28: PRINT SPC(50);
SPACEDELAY: IF XX$ = CHR$(32) THEN FOR X1 = 1 TO KISI: NEXT X1: GOTO NEXUM
ELSE GOTO GETSPACE
NG$ = "N"
NEXUM: CALL CLEARKEYBOARD
'IF GiveSound$ = "Y" THEN SOUND 5000, 2: SOUND 3000, 2
'IF GiveSound$ = "Y" THEN SOUND 2000, 2: SOUND 4000, 7
IF GiveSound$ = "Y" THEN SOUND 800, 2
LOCATE 12 / DIV, MID, 0: PRINT " "; CHR$(16); CHR$(17); : FOR ASTD = 1 TO
ASTPROMPT: NEXT ASTD
LOCATE 14 / DIV, MID + 1, 0: COLOR 0, 7: PRINT SPC(2); : COLOR 7, 0
LOCATE 12 / DIV, MID, 0
'IF ScreenFresh$ = "Y" THEN ScreenSynch = 8: WHILE ScreenSynch = 8:
ScreenSynch = INP(986) AND 8: WEND
CALL Distractor(Do.It$, Subject.Lastname$, Subject.Firstname$, ModeSet,
DistractDelay, Symm$, Flash$, TP, L, R, B, NumDistract, AllFlash$)
LOCATE 12 / DIV, MID, 0
IF ScreenFresh$ = "Y" THEN GOTO Synch ELSE GOTO NoSynch
Synch: ScreenSynch = INP(986) AND 8: IF ScreenSynch = 8 THEN GOTO Synch
NoSynch: PRINT USING "###"; STIM(BL, T);

LOCATE 14 / DIV, MID, 0: TT = 0
FIRSTDIGIT: K1$ = INKEY$: TT = TT + 1: IF K1$ = "" THEN GOTO FIRSTDIGIT
  IF K1$ = CHR$(27) THEN BLOCK% = BL: ESCAPE$ = "Y": GOTO SKIPBL
  IF ((ASC(K1$) >= 48) AND (ASC(K1$) <= 57)) THEN GOTO PRINTDIGIT ELSE GOTO
FIRSTDIGIT
PRINTDIGIT: LOCATE 14 / DIV, MID + 1, 0: PRINT K1$;
  IF VAL(K1$) <> INT(ANSWER(BL, T) / 10) THEN K2$ = "0": GOTO SAVEIT: 'FOR
FIRST KEY ERRORS
SECDIGIT: K2$ = INKEY$: IF K2$ = "" THEN GOTO SECDIGIT
  IF K2$ = CHR$(27) THEN BLOCK% = BL: ESCAPE$ = "Y": GOTO SKIPBL
  IF ((ASC(K2$) >= 48) AND (ASC(K2$) <= 57)) THEN GOTO PRINTsecDIGIT ELSE GOTO
SECDIGIT
PRINTsecDIGIT: LOCATE 14 / DIV, MID + 2, 0: PRINT K2$
```

```
SAVEIT: CHOICE(BL, T) = ((VAL(K1$) * 10) + VAL(K2$)): IF DIGSIZE = 1 THEN
CHOICE(BL, T) = INT(CHOICE(BL, T) / 10)

'IF BL = block% THEN IF CHOICE(BL, T) <> ANSWER(BL, T) THEN BEEP: NG$ = "Y":
LOCATE (10 / div) - 1, mid - 10: PRINT clue$; : GOTO NEXUM
    IF ErrorBeep$ = "Y" THEN IF CHOICE(BL, T) <> ANSWER(BL, T) THEN LOCATE 14 /
DIV, MID, 0: PRINT "  "; : BEEP IF BLFORMAT(BL, 1) = 4 THEN IF CHOICE(BL, T) <> ANSWER(BL, T) THEN BEEP: NG$
= "Y": ActualKey = CHOICE(BL, T): COLOR 7, 0: IF NOSHOW$(BL) = "Y" THEN
LOCATE (10 / DIV) - 1, MID - 10: COLOR 7, 0: PRINT CLUE$; : GOTO NEXUM ELSE
GOTO NEXUM
    IF BLFORMAT(BL, 1) = 5 THEN IF CHOICE(BL, T) <> ANSWER(BL, T) THEN NG$ =
"Y": ActualKey = CHOICE(BL, T): COLOR 7, 0
    IF NG$ = "Y" THEN TimeArray(BL, T) = -TT * Td1: CHOICE(BL, T) = ActualKey:
'ERRORS ON ALTERNATION EXCLUDED
    IF NG$ = "N" THEN IF (CHOICE(BL, T) = ANSWER(BL, T)) THEN TimeArray(BL, T) =
TT * Td1
    IF NG$ = "N" THEN IF (CHOICE(BL, T) <> ANSWER(BL, T)) THEN LOCATE 14 / DIV,
MID + 1, 0: TimeArray(BL, T) = -TT * Td1: COLOR 0, 7: PRINT SPC(2); : COLOR
7, 0: ER(BL) = ER(BL) + 1: ERTIME(BL, ER(BL)) = TT * Td1: EROR = EROR + 1:
MISTAKE(EROR, 1) = BL
: MISTAKE(EROR, 2) = T: REM BEEP
    IF CHOICE(BL, T) = ANSWER(BL, T) THEN SumCorr = SumCorr + 1
  NEXT T
LOCATE 1, 1, 0: CLS
    IF INT((SumCorr / TRIALS%) * 100) < PassPercent THEN PassRun$ = "N"

IF BL < BLOCK% THEN LOCATE 9 / DIV, MID: PRINT "STOP"; : LOCATE 23 / DIV, MID
- 13: PRINT "PRESS ANY KEY TO BEGIN BLOCK"; BL + 1;   ELSE GOTO PASSOVER
GETBREAKEY: XX$ = INKEY$: IF XX$ = "" THEN GOTO GETBREAKEY
PASSOVER: REM JUST SKIP
IF XX$ = CHR$(27) THEN BLOCK% = BL: GOTO SKIPBL
NEXT BL
SKIPBL: ''' ESCAPE KEY PRESSED JUMP OVER
LOCATE 1, 1, 0: 'RETURN
REPRESENT: ' FOR STIMULI MISSED ON FIRST GO ROUND, CURRENTLY DISABLED VIA REM
LOCATE 1, 1, 0: 'RETURN

END SUB

' PERINFO.BAS

DECLARE SUB BOX (T!, L!, R!, B!)

NoSubFile:
INPUT "No file found"; gg$
FoundSubjectFile$ = "N": RESUME NEXT

SUB givemesubjectstory (Drive$, Edit.it$, subject.lastname$,
    subject.firstname$, subject.id$, subject.age$, subject.sex$, subject.date$,
    subject.study$, subject.studyname$) STATIC getsubjectfile:
 IF Edit.it$ = "M" THEN Edit.it$ = "Y": GOTO getsubjectinfo
 OPEN Drive$ + "SUBINFO.ID" FOR INPUT AS #1
    INPUT #1, subject.lastname$, subject.firstname$, subject.id$, subject.age$,
subject.sex$, subject.date$, subject.study$, subject.studyname$
    CLOSE #1
    FoundSubjectFile$ = "Y"
IF Edit.it$ = "Y" THEN GOTO getsubjectinfo ELSE EXIT SUB getsubjectinfo:
'startsubinfo: IF foundsubJECTfile$ = "Y" THEN LOCATE 7, 19: COLOR 0, 7:
PRINT " DATA CURRENTLY IN SUBJECT FILE "; : COLOR 7, 0 startsubinfo: IF FoundSubjectFile$ = "Y" THEN LOCATE 7, 27: COLOR 0, 7: PRINT
" CURRENT SUBJECT FILE "; : COLOR 7, 0
    LOCATE 3, 15: PRINT "Enter new subject data by overwriting old data"
    LOCATE 4, 23: PRINT "Press return key to enter data"
```

```
IF FoundSubjectFile$ = "N" THEN LOCATE 7, 22: COLOR 0, 7: PRINT " UNABLE TO
FIND SUBJECT FILE    "; : COLOR 7, 0

LOCATE 9, 20:  PRINT "Enter Last Name   : "; subject.lastname$
  LOCATE 10, 20: PRINT "Enter First Name  : "; subject.firstname$
  LOCATE 11, 20: PRINT "Enter Subject ID# : "; subject.id$
  LOCATE 12, 20: PRINT "Enter Age         : "; subject.age$
  LOCATE 13, 20: PRINT "Enter Gender      : "; subject.sex$
  LOCATE 14, 20: PRINT "Enter Study       : "; subject.studyname$
  LOCATE 15, 1: PRINT STRING$(79, ".");
getsubLASTname: COLOR 7, 0: LOCATE 9, 40: LINE INPUT S.N$
  IF S.N$ = "" THEN S.N$ = subject.lastname$ ELSE subject.lastname$ = S.N$
  LOCATE 9, 40: PRINT SPC(25); : LOCATE 9, 40: COLOR 0, 7: PRINT
subject.lastname$; : COLOR 7, 0
  IF subject.lastname$ = "" THEN GOTO getsubLASTname
getsubFIRSTname: COLOR 7, 0: LOCATE 10, 40: LINE INPUT S.NF$
  IF S.NF$ = "" THEN S.NF$ = subject.firstname$ ELSE subject.firstname$ =
S.NF$
  LOCATE 10, 40: PRINT SPC(25); : LOCATE 10, 40: COLOR 0, 7: PRINT
subject.firstname$; : COLOR 7, 0
  IF subject.firstname$ = "" THEN GOTO getsubFIRSTname getsubid: LOCATE 11, 40: LINE INPUT s.id$
  IF s.id$ = "" THEN s.id$ = subject.id$ ELSE subject.id$ = s.id$
  LOCATE 11, 40: PRINT SPC(25); : LOCATE 11, 40: COLOR 0, 7: PRINT
subject.id$; : COLOR 7, 0
  IF subject.id$ = "" THEN GOTO getsubid
getsubage: LOCATE 12, 40: LINE INPUT s.age$
  IF s.age$ = "" THEN s.age$ = subject.age$ ELSE subject.age$ = s.age$
  LOCATE 12, 40: PRINT SPC(25); : LOCATE 12, 40: COLOR 0, 7: PRINT
subject.age$; : COLOR 7, 0
  IF subject.age$ = "" THEN GOTO getsubage
getsubsex: LOCATE 13, 40: LINE INPUT s.sex$
  IF s.sex$ = "" THEN s.sex$ = subject.sex$ ELSE subject.sex$ = s.sex$
  LOCATE 13, 40: PRINT SPC(25); : LOCATE 13, 40: COLOR 0, 7: PRINT
subject.sex$; : COLOR 7, 0
  IF subject.sex$ = "" THEN GOTO getsubsex
GETSUBSTUDY: LOCATE 14, 40: LINE INPUT S.STUDY$
  IF S.STUDY$ = "" THEN S.STUDY$ = subject.studyname$ ELSE subject.studyname$
= S.STUDY$
  'IF ((VAL(S.STUDY$) < 1) OR (VAL(S.STUDY$) > 5)) THEN BEEP: LOCATE 14, 40:
PRINT SPC(40); : LOCATE 14, 45: PRINT "1..5": GOTO GETSUBSTUDY
  LOCATE 14, 40: PRINT SPC(25); : LOCATE 14, 40: COLOR 0, 7: PRINT
subject.studyname$; : COLOR 7, 0
  IF subject.studyname$ = "" THEN GOTO GETSUBSTUDY
getfix: LOCATE 21, 20: PRINT SPC(40); : LOCATE 20, 20: LINE INPUT "Fix Errors
<Y/N>: "; fix$
  IF ((fix$ <> "Y") AND (fix$ <> "y") AND (fix$ <> "n") AND (fix$ <> "N"))
THEN BEEP: LOCATE 20, 20: PRINT SPC(45); : GOTO getfix
  IF ((fix$ = "Y") OR (fix$ = "y")) THEN LOCATE 20, 20: PRINT SPC(35); : GOTO
startsubinfo
  LOCATE 20, 10, 0
  subject.date$ = DATE$
  'LOCATE 17, 20: PRINT "Saving Subject Information in file C:SUBINFO.DAT"
  OPEN Drive$ + "SUBINFO.ID" FOR OUTPUT AS #1
  PRINT #1, subject.lastname$; ","; subject.firstname$; ","; subject.id$;
    ","; subject.age$; ","; subject.sex$; ","; subject.date$; ",";
    subject.study$; ","; subject.studyname$
  CLOSE #1
  subid$ = LEFT$(subject.firstname$, 1)
  subid$ = subid$ + LEFT$(subject.lastname$, 1)
  subid$ = subid$ + LEFT$(subject.id$, 4)
  subid$ = subid$ + ".ID"
  OPEN Drive$ + subid$ FOR APPEND AS #1
  PRINT #1, subject.lastname$; ","; subject.firstname$; ","; subject.id$;
    ","; subject.age$; ","; subject.sex$; ","; subject.date$; ",";
    subject.study$; ","; subject.studyname$
  CLOSE #1

END SUB
```

' MINUSVAL.BAS

```
SUB MINUSVAL (MED(), BLOCK%)
'MINUSVALUES:
   PRINT #1, " "
   PRINT #1, "        DIFFERENCE BETWEEN MEDIANS"

PRINT #1, " "
   'PRINT #1, "Block 2 (Subtraction) - Block 1 (Copy) = "; : PRINT #1, USING
   "######.##"; MED(2) - MED(1)
   'PRINT #1, "Block 3 (Subtraction) - Block 3 (Copy) = "; : PRINT #1, USING
   "######.##"; MED(5) - MED(4)
   'PRINT #1, "Block 3 (Sub-First Half) - Block 3 (Copy-First Half) = "; :
   PRINT #1, USING "######.##"; MED(8) - MED(6) 'PRINT #1, "Block 3 (Sub-
   Second Half) - Block 3 (Copy-Second Half) = "; : PRINT #1, USING
   "######.##"; MED(9) - MED(7) 'PRINT #1, SPC(8); "MEAN CHANGE ACROSS BLOCKS"
   'PRINT #1, " "

PRINT #1, SPC(7);
   FOR A1 = 1 TO BLOCK%
     PRINT #1, USING "#######"; A1;
   NEXT A1
   PRINT #1, " "
   'PRINT #1, STRING$(8 * BLOCK% + 8, "-")
   PRINT #1, STRING$(80, "-")
   ZERO = 0
   FOR A1 = 1 TO BLOCK% - 1
    PRINT #1, USING "##"; A1;
    PRINT #1, " :   ";
    FOR SP = 1 TO A1: PRINT #1, SPC(7); : NEXT SP
    FOR A2 = A1 + 1 TO BLOCK%
      PRINT #1, USING "#######"; CINT(MED(A2) - MED(A1));
    NEXT A2
    PRINT #1, " "
   NEXT A1
   'PRINT #1, STRING$(8 * BLOCK% + 8, "-")
   PRINT #1, STRING$(80, "-")
   PRINT #1, " "
   PRINT #1, "* Difference = Higher Block - Lower Block"
   PRINT #1, CHR$(12)

END SUB
```

' PARAMSP$.BAS

```
DECLARE SUB PARAMSPD (BLOCK, StartTRCalc, MAXBLOCKS, MAXTRIALS, TD2, NEWID$,
   EDIT.IT$, PARA$, PARAF$, PDRIVE$, DIGSIZE, MODE$, MID, DIV, MODESET,
   BLOCK$, BLOCK%, Trials%, TYPEBLOCK$, TBORDER$, TYPEISI$, ISI$, ISI, KISI$,
   KISI, SHOWRES$, SHOWCOMP$,   NUMCON, CONTRAST(), CONNAME$(), BLFORMAT(),
   NOSHOW$(), Trials$, OP$, NOSH$, VALUE$, SAMP$, NUMCON$, CON1$, CON2$, CO,
   SAVEPF$, OUTPF$, POUTDRIVE$, BL, Distracted$(), StartTR$, Distract$,
   DisFlash$)
DECLARE SUB givemesubjectstory (DRIVE$, EDIT.IT$, subject.lastname$,
   subject.firstname$, subject.id$, subject.age$, subject.sex$, subject.date$,
   subject.study$, subject.studyname$)
DECLARE SUB BOX (T!, L!, R!, B!)

ERRORPROCESS:
 CLOSE : LOCATE 15, 25: BEEP
 SELECT CASE ERR
   CASE 64:
    PRINT "***     INVALID FILE NAME   ***"
   CASE 71:
    PRINT "***      DISK NOT READY     ***"
   CASE 53, 76:
    PRINT "*** FILE OR PATH NOT FOUND ***"
   CASE 61:
    PRINT "***        DISK FULL        ***"
   CASE ELSE:
    PRINT "*** ERROR NUMBER "; ERL; " HAS OCCURRED."
 END SELECT
```

```
      LOCATE 17, 25: INPUT "PRESS RETURN KEY TO CONTINUE "; GARB$
      FOR X = 9 TO 17: LOCATE X, 1: PRINT SPC(70); : NEXT X: 'LOCATE 12, 1:
      PRINT SPC(70); : LOCATE 13, 1: PRINT SPC(70); : LOCATE 14, 1: PRINT
      SPC(70);
      FOND$ = "N": RESUME NEXT
TRYAGAIN:

SUB PARAMSPD (BLOCK, StartTRCalc, MAXBLOCKS, MAXTRIALS, TD2, NEWID$,
   EDIT.IT$, PARA$, PARAF$, PDRIVE$, DIGSIZE, MODE$, MID, DIV, MODESET,
   BLOCK$, BLOCK%, Trials%, TYPEBLOCK$, TBORDER$, TYPEISI$, ISI$, ISI, KISI$,
   KISI, SHOWRES$, SHOWCOMP$, NUMCON,   CONTRAST(), CONNAME$(), BLFORMAT(),
   NOSHOW$(), Trials$, OP$, NOSH$, VALUE$, SAMP$, NUMCON$, CON1$, CON2$, CO,
   SAVEPF$, OUTPF$, POUTDRIVE$, BL, Distracted$(), StartTR$, Distract$,
   DisFlash$)

SHARED FOND$

STARTPARAMS: 'LOCATE 1, 1, 1, 13, 14
   FOND$ = "Y"
   CLS
TOPOF: PARA$ = "N"
   '''DEMO''' LOCATE 2, 32: COLOR 0, 7: PRINT " PARAMETER SETTINGS "; : COLOR
7, 0
   '''DEMO''' LOCATE 4, 17: PRINT "PRESS "; : COLOR 0, 7: PRINT " RETURN "; :
COLOR 7, 0: PRINT " FOR <DEFAULT> "; : LOCATE 4, 49: PRINT "PRESS "; : COLOR
0, 7: PRINT " * "; : COLOR 7, 0: PRINT " TO REDO"
   '''DEMO''' T = 6: B = 17: L = 9: R = 73: CALL BOX(T, L, R, B)
PARAF$ = "SPDEMO": NEWID$ = "N": PARA$ = "Y": PDRIVE$ = "C": GOTO OPENDEMO:
   IF PARA$ = "Y" THEN GOTO GETPARAMNAME
   NEWID$ = "N": '''DEMO

GETNEWID:
   LOCATE 7, 11, 1, 6, 10: INPUT "CHANGE SUBJECT INFORMATION <N>: "; NEWID$
   IF NEWID$ = "" THEN NEWID$ = "N"
   NEWID$ = UCASE$(NEWID$)
   IF NEWID$ <> "Y" AND NEWID$ <> "N" THEN LOCATE 7, 45: PRINT SPC(3); : BEEP:
   GOTO GETNEWID
   IF NEWID$ = "Y" THEN EDIT.IT$ = "Y": CLS : CALL givemesubjectstory(DRIVE$,
   EDIT.IT$, subject.lastname$, subject.firstname$, subject.id$, subject.age$,
   subject.sex$, subject.date$, subject.study$, subject.studyname$): GOTO
   STARTPARAMS:
   'GOSUB GETSUBJECTFILE: GOTO STARTPARAMS GETPARAMFILE:
   LOCATE 8, 11: INPUT "EXTERNAL PARAMETER FILE <N>: "; PARA$
   PARA$ = UCASE$(PARA$)
   IF PARA$ = "*" THEN GOTO STARTPARAMS
   IF PARA$ = "" THEN PARA$ = "N"
   IF PARA$ <> "Y" AND PARA$ <> "N" THEN LOCATE 8, 42: PRINT SPC(3); : BEEP:
   GOTO GETPARAMFILE
   IF PARA$ = "N" THEN GOTO GETMODE
   IF PARA$ = "Y" THEN LOCATE 18, 29: PRINT "PRESS "; : COLOR 0, 7: PRINT " ?
   "; : COLOR 7, 0: PRINT " TO SEE FILE NAMES "

GETPARAMNAME:
   IF PARA$ = "Y" THEN LOCATE 10, 11: PRINT SPC(30); : LOCATE 9, 11: PRINT
SPC(50); : LOCATE 9, 11: INPUT "ENTER FILE NAME [.SPA]: "; PARAF$
   IF PARAF$ = "*" THEN PARA$ = "N": GOTO STARTPARAMS
   IF PARAF$ = "" THEN BEEP: GOTO GETPARAMNAME
   'LOCATE 17, 1: PRINT SPC(70);
   FOR LI = 18 TO 23: LOCATE LI, 1, 0: PRINT SPC(78); : NEXT LI

GETPDRIVE:
   LOCATE 10, 11: PRINT SPC(30); : LOCATE 10, 11: INPUT "DRIVE <C>: "; PDRIVE$
   IF PDRIVE$ = "*" THEN PARA$ = "N": GOTO STARTPARAMS
   IF PDRIVE$ = "" THEN PDRIVE$ = "C"
   'ON ERROR GOTO GETPARAMFILE
   IF ((PDRIVE$ <> "A") AND (PDRIVE$ <> "B") AND (PDRIVE$ <> "C") AND (PDRIVE$
   <> "D")) THEN LOCATE 10, 24: PRINT SPC(3); : BEEP: GOTO GETPDRIVE
   IF PARAF$ = "?" THEN LOCATE 16, 9, 0: SHELL "DIR " + PDRIVE$ + ":*.SPA/W":
   GOTO GETPARAMNAME
```

```
CLOSE #1: ON ERROR GOTO ERRORPROCESS: 'ON ERROR GOTO GETPARAMFILE
'''?ON ERROR GOTO ERRORPROCESS: LOCATE 18, 4: PRINT "NO PARAMETER FILES ON
SPECIFIED DRIVE"; : LOCATE 19, 4: INPUT "PRESS <RETURN> KEY TO CONTINUE";
XX$: GOTO STARTPARAMS

LOCATE 12, 1, 0
OPENDEMO: OPEN PDRIVE$ + ":" + PARAF$ + ".SPA" FOR INPUT AS #1:
IF FOND$ = "N" THEN GOTO STARTPARAMS
 INPUT #1, DIGSIZE, MODE$, MID, DIV, MODESET, BLOCK%, Trials%, TYPEBLOCK$,
 TBORDER$, TYPEISI$, ISI$, ISI, KISI$, KISI, SHOWRES$, SHOWCOMP$, NUMCON,
 StartTRCalc
  FOR CO = 1 TO NUMCON
    INPUT #1, CONTRAST(CO, 1), CONTRAST(CO, 2), CONNAME$(CO)
  NEXT CO FOR BL = 1 TO BLOCK%
   INPUT #1, BLFORMAT(BL, 1), BLFORMAT(BL, 2), BLFORMAT(BL, 3), NOSHOW$(BL),
Distracted$(BL, 1), Distracted$(BL, 2)
  NEXT BL
CLOSE #1
ISI = (VAL(ISI$) * 1000) / TD2: ' This takes care of different machines
time.div's
KISI = (VAL(KISI$) * 1000) / TD2
CLOSE #1: PARA$ = "N": GOTO OUTOFPARAMS GETMODE: LOCATE 9, 11: INPUT "LARGE <1> OR STANDARD <2> SIZE DIGITS <2>: ";
MODE$
IF MODE$ = "*" THEN GOTO STARTPARAMS
IF MODE$ = "" THEN MODE$ = "2"
IF MODE$ <> "1" AND MODE$ <> "2" THEN LOCATE 9, 56: PRINT SPC(3); : BEEP:
GOTO GETMODE
IF MODE$ = "1" THEN MID = 20: DIV = 2: MODESET = 40
IF MODE$ = "2" THEN MID = 40: DIV = 1: MODESET = 80

GETDIGITSIZE: LOCATE 10, 11: INPUT "ONE <1> OR TWO <2> DIGIT NUMBERS <2>: ";
DIGSIZE$
IF DIGSIZE$ = "*" THEN GOTO STARTPARAMS
IF DIGSIZE$ = "" THEN DIGSIZE$ = "2"
IF VAL(DIGSIZE$) > 2 OR VAL(DIGSIZE$) < 1 THEN BEEP: LOCATE 10, 51: PRINT
SPC(3); : GOTO GETDIGITSIZE
DIGSIZE = VAL(DIGSIZE$)

GETBLOCK: LOCATE 11, 11: INPUT "NUMBER OF BLOCKS <4>: "; BLOCK$
IF BLOCK$ = "*" THEN GOTO STARTPARAMS
IF BLOCK$ = "" THEN BLOCK$ = "4"
IF ((VAL(BLOCK$) < 1) OR (VAL(BLOCK$) > MAXBLOCKS)) THEN LOCATE 11, 35:
PRINT SPC(3); : LOCATE 21, 34: COLOR 0, 7: PRINT " MUST BE 1-8 "; : COLOR 7,
0: BEEP: GOTO GETBLOCK
LOCATE 21, 30: PRINT SPC(20);
BLOCK% = VAL(BLOCK$)

GETTRIALS: LOCATE 12, 11: INPUT "NUMBER OF TRIALS PER BLOCK <30>: "; Trials$
IF Trials$ = "*" THEN GOTO STARTPARAMS
IF Trials$ = "" THEN Trials$ = "30"
IF ((VAL(Trials$) < 1) OR (VAL(Trials$) > MAXTRIALS)) THEN LOCATE 12, 45:
PRINT SPC(3); : LOCATE 20, 34: COLOR 0, 7: PRINT " MUST BE 1-50 "; : COLOR
7, 0: BEEP: GOTO GETTRIALS
Trials% = VAL(Trials$)
LOCATE 20, 30: PRINT SPC(20);

GetStartTrial: LOCATE 13, 11: INPUT "NUMBER OF PRACTICE TRIALS <0>: ";
StartTR$
IF StartTR$ = "*" THEN GOTO STARTPARAMS
IF StartTR$ = "" THEN StartTR$ = "0"
LimitPrac = 5
IF VAL(Trials$) <= 5 THEN StartTR$ = "0": GOTO SKP
IF VAL(Trials$) - VAL(StartTR$) < 5 THEN LimitPrac = VAL(Trials$) -
VAL(StartTR$)
  IF (VAL(StartTR$) < 0) OR ((VAL(Trials$) - (VAL(StartTR$)) < 5) OR
VAL(StartTR$) > 5) THEN LOCATE 13, 44: PRINT SPC(3); : LOCATE 20, 34: COLOR
```

```
0, 7: PRINT " MUST BE 0-"; : PRINT USING "#"; LimitPrac; : PRINT " "; : COLOR
7, 0: BEEP: GOTO _ GetStartTrial
SKP:
 'Minimum of 5 Trials per run
 StartTRCalc = VAL(StartTR$) + 1
 LOCATE 20, 30: PRINT SPC(30);

GETTYPEBLOCK: LOCATE 14, 11: INPUT "EVERY BLOCK <1> RANDOM OR ONLY FIRST <2>
BLOCK <2>: "; TYPEBLOCK$
 IF TYPEBLOCK$ = "*" THEN GOTO STARTPARAMS
 IF TYPEBLOCK$ = "" THEN TYPEBLOCK$ = "2"
 IF ((TYPEBLOCK$ <> "1") AND (TYPEBLOCK$ <> "2")) THEN LOCATE 14, 64: PRINT
 SPC(3); : BEEP: GOTO GETTYPEBLOCK
 IF TYPEBLOCK$ = "2" THEN GOTO GETORDER ELSE TBORDER$ = "1": GOTO
 GETINTERTYPE

GETORDER: LOCATE 15, 11: INPUT "SAME ORDER <1> OR RANDOMIZED <2> ACROSS
BLOCKS <1>: "; TBORDER$
 IF TBORDER$ = "*" THEN GOTO STARTPARAMS
 IF TBORDER$ = "" THEN TBORDER$ = "1"
 IF ((TBORDER$ <> "1") AND (TBORDER$ <> "2")) THEN LOCATE 15, 65: PRINT
 SPC(3); : BEEP: GOTO GETORDER
 'LOCATE 15, 11: PRINT "INTER-STIMULUS INTERVAL <1> OR SPACE BAR <2>: ";

GETINTERTYPE: LOCATE 15, 11: PRINT SPC(55); : LOCATE 15, 11: INPUT "INTER-
STIMULUS INTERVAL <1> OR SPACE BAR <2>: "; TYPEISI$
 IF TYPEISI$ = "*" THEN GOTO STARTPARAMS
 IF TYPEISI$ = "" THEN TYPEISI$ = "1"
 IF ((TYPEISI$ <> "1") AND (TYPEISI$ <> "2")) THEN LOCATE 15, 60: PRINT
 SPC(3); : BEEP: GOTO GETINTERTYPE

IF TYPEISI$ = "1" THEN LOCATE 16, 11: INPUT "INTER-STIMULUS DURATION IN
SECONDS <2>: "; ISI$
 IF ISI$ = "*" THEN GOTO STARTPARAMS
 IF ISI$ = "" THEN ISI$ = "2"
 IF ((VAL(ISI$) < 0) OR (VAL(ISI$) > 20)) THEN LOCATE 16, 53: PRINT SPC(4); :
 BEEP: LOCATE 16, 51: INPUT ISI$
 ISI = (VAL(ISI$) * 1000) / TD2

IF TYPEISI$ = "2" THEN LOCATE 16, 11: INPUT "DELAY AFTER SPACE BAR IN
SECONDS <2>: "; KISI$
 IF KISI$ = "*" THEN GOTO STARTPARAMS
 IF KISI$ = "" THEN KISI$ = "2"
 IF ((VAL(KISI$) < 0) OR (VAL(KISI$) > 20)) THEN LOCATE 16, 49: PRINT SPC(3);
 : BEEP: LOCATE 16, 49: INPUT KISI$
 KISI = (VAL(KISI$) * 1000) / TD2

STONYADD:
 'FOR XL = 16 TO 24: PRINT SPC(79); : NEXT XL
 T = 17: B = 23: L = 9: R = 73: CALL BOX(T, L, R, B)
 LOCATE 17, 9: PRINT CHR$(204); : LOCATE 17, 73: PRINT CHR$(185);
 'FOR BL = 1 TO BLOCK%
 'LOCATE 18, 11: PRINT "BLOCK ";
 'LOCATE 18, 23: PRINT USING "##"; BL
 'LOCATE 19, 11: PRINT "OPERATION: 1-ADDITION 2-SUBTRACTION 3-COPY 4-ALT
 <3>:";

'LOCATE 20, 11: PRINT "NUMBER DESIRED <1>: ";
 ''IF TYPEBLOCK$ = "2" THEN LOCATE 21, 11: PRINT "<1> SAME SAMPLE  <2> SAME
 RESPONSE <2>: ";

GETTYPE:
 FOR BL = 1 TO BLOCK%
 LOCATE 18, 11: PRINT "BLOCK:";
 LOCATE 18, 19: PRINT USING "##"; BL
TASK: LOCATE 19, 11: INPUT "TASK: 1-COPY 2-SUBTRACT 3-ADD 4-ALTERNATE 5-
RANDOM <1>: "; OP$
     'IF ((OP$ <> "1") AND (OP$ <> "2") AND (OP$ <> "3") AND (OP$ <> "4"))
 THEN LOCATE 19, 65: PRINT "    "; : BEEP: GOTO GETTYPE
 IF OP$ = "*" THEN GOTO STARTPARAMS
```

```
    IF OP$ = "" THEN OP$ = "1"
    IF ((OP$ <> "1") AND (OP$ <> "2") AND (OP$ <> "3") AND (OP$ <> "4") AND (OP$
      <> "5")) THEN LOCATE 19, 69: PRINT SPC(3); : BEEP: GOTO GETTYPE
    IF OP$ = "1" THEN OP$ = "3" ELSE IF OP$ = "3" THEN OP$ = "1"
    BLFORMAT(BL, 1) = VAL(OP$)
    IF OP$ = "3" THEN GOTO BYPASS
    IF OP$ = "4" THEN GOTO GETCLUE
    IF OP$ = "5" THEN GOTO GETCLUERAND ELSE GOTO GETVALUE

GETCLUE: LOCATE 20, 11: INPUT "<1> CUED  <2> REVERSE  <3> NO CUE: "; NOSH$
    IF NOSH$ = "*" THEN LOCATE 19, 11: PRINT SPC(60); : LOCATE 20, 11: PRINT
SPC(60); : GOTO GETTYPE
    IF NOSH$ = "" THEN NOSH$ = "1"
    IF VAL(NOSH$) <= 0 OR VAL(NOSH$) > 3 THEN LOCATE 20, 47: PRINT SPC(20); :
    BEEP: GOTO GETCLUE
    IF NOSH$ = "1" THEN NOSH$ = "N"
    IF NOSH$ = "2" THEN NOSH$ = "R"
    IF NOSH$ = "3" THEN NOSH$ = "Y"
    NOSHOW$(BL) = NOSH$
    GOTO GETVALUE

GETCLUERAND: LOCATE 20, 11: INPUT "<1> CUED  <2> REVERSE: "; NOSH$
    IF NOSH$ = "*" THEN LOCATE 19, 11: PRINT SPC(60); : LOCATE 20, 11: PRINT
SPC(60); : GOTO GETTYPE
    IF NOSH$ = "" THEN NOSH$ = "1"
    IF VAL(NOSH$) <= 0 OR VAL(NOSH$) > 2 THEN LOCATE 20, 47: PRINT SPC(20); :
    BEEP: GOTO GETCLUERAND
    IF NOSH$ = "1" THEN NOSH$ = "N"
    IF NOSH$ = "2" THEN NOSH$ = "R"
    NOSHOW$(BL) = NOSH$

GETVALUE: LOCATE 20, 11: PRINT SPC(50); : LOCATE 20, 11: INPUT "NUMBER
DESIRED <1>: "; VALUE$
    IF VALUE$ = "*" THEN LOCATE 19, 11: PRINT SPC(60); : LOCATE 20, 11: PRINT
SPC(60); : GOTO GETTYPE
    IF VALUE$ = "" THEN VALUE$ = "1"
    IF DIGSIZE = 1 THEN IF ((VAL(VALUE$) < 1) OR (VAL(VALUE$) > 3)) THEN LOCATE
      20, 33: PRINT SPC(30); : BEEP: COLOR 0, 7: LOCATE 22, 34: PRINT " MUST BE
      1-3 ": COLOR 7, 0: GOTO GETVALUE
    IF DIGSIZE = 2 THEN IF ((VAL(VALUE$) < 1) OR (VAL(VALUE$) > 19)) THEN LOCATE
      20, 33: PRINT SPC(30); : BEEP: COLOR 0, 7: LOCATE 22, 34: PRINT " MUST BE
      1-19 ": COLOR 7, 0: GOTO GETVALUE
    BLFORMAT(BL, 2) = VAL(VALUE$)
    SAMP$ = ""
    IF TYPEBLOCK$ = "1" THEN GOTO BYPASS

LOCATE 22, 34: PRINT SPC(16);
GETBLTYPE: LOCATE 20, 11: INPUT "<1> SAME STIMULI OR <2> SAME RESPONSES <2>:
    "; SAMP$
    IF SAMP$ = "*" THEN LOCATE 19, 11: PRINT SPC(60); : LOCATE 20, 11: PRINT
SPC(60); : LOCATE 21, 11: PRINT SPC(60); : GOTO GETTYPE
    IF SAMP$ = "" THEN SAMP$ = "2"
    IF ((SAMP$ <> "1") AND (SAMP$ <> "2")) THEN LOCATE 20, 57: PRINT SPC(6); :
    BEEP: GOTO GETBLTYPE
    BLFORMAT(BL, 3) = VAL(SAMP$)

BYPASS: REM JUST GET AWAY
    FOR LI = 20 TO 22: LOCATE LI, 11: PRINT SPC(60); : NEXT LI

GETDISTRACTOR: LOCATE 20, 11: INPUT "DISTRACTOR <N>: "; Distract$
    IF Distract$ = "*" THEN LOCATE 19, 69: PRINT SPC(3); : LOCATE 20, 11: PRINT
SPC(60); : LOCATE 21, 11: PRINT SPC(60); : GOTO GETTYPE Distract$ = UCASE$(Distract$)
    IF Distract$ = "" THEN Distract$ = "N"
    IF Distract$ <> "Y" AND Distract$ <> "N" THEN LOCATE 20, 29: PRINT SPC(10);
      : BEEP: GOTO GETDISTRACTOR
    Distracted$(BL, 1) = Distract$
    IF Distract$ = "Y" THEN GOTO GETFLASH ELSE Distracted$(BL, 2) = "N": GOTO
NoFlash
```

```
GETFLASH: LOCATE 21, 11: INPUT "FLASHING <Y>: "; DisFlash$
  IF DisFlash$ = "*" THEN LOCATE 20, 29: PRINT SPC(6); : LOCATE 21, 11: PRINT
SPC(60); : GOTO GETDISTRACTOR
  DisFlash$ = UCASE$(DisFlash$)
  IF DisFlash$ = "" THEN DisFlash$ = "Y"
  IF DisFlash$ <> "Y" AND DisFlash$ <> "N" THEN LOCATE 21, 27: PRINT SPC(10);
  : BEEP: GOTO GETFLASH
  Distracted$(BL, 2) = DisFlash$
NoFlash:
  FOR LI = 19 TO 22: LOCATE LI, 11: PRINT SPC(60); : NEXT LI: LOCATE 19, 69:
PRINT SPC(3);
NEXT BL SHOWRESULTS: LOCATE 18, 11: PRINT SPC(60); : LOCATE 18, 11: INPUT "SHOW
RESULTS <Y>: "; SHOWRES$
  IF SHOWRES$ = "*" THEN LOCATE 18, 11: PRINT SPC(30); : GOTO GETTYPE
  SHOWRES$ = UCASE$(SHOWRES$)
  IF SHOWRES$ = "" THEN SHOWRES$ = "Y"
  IF SHOWRES$ <> "Y" AND SHOWRES$ <> "N" THEN LOCATE 18, 30: PRINT SPC(30); :
BEEP: GOTO SHOWRESULTS SHOWCOMPS: IF SHOWRES$ = "N" THEN GOTO SAVEPARAM
  IF BLOCK% = 1 THEN GOTO SAVEPARAM
  LOCATE 19, 11: INPUT "SHOW COMPARISONS <Y>: "; SHOWCOMP$
  IF SHOWCOMP$ = "*" THEN LOCATE 19, 11: PRINT SPC(60); : GOTO SHOWRESULTS
  IF SHOWCOMP$ = "" THEN SHOWCOMP$ = "Y"
  SHOWCOMP$ = UCASE$(SHOWCOMP$)
  IF SHOWCOMP$ <> "Y" AND SHOWCOMP$ <> "N" THEN BEEP: GOTO SHOWCOMPS
  IF SHOWCOMP$ = "N" THEN GOTO SAVEPARAM
  SELECT CASE BLOCK%
    CASE IS = 1: MAXCON = 0
    CASE IS = 2: MAXCON = 1
    CASE IS = 3: MAXCON = 3
    CASE ELSE
      MAXCON = 5
  END SELECT
GETCONS: LOCATE 20, 11: PRINT "NUMBER OF CONTRASTS <1..";  : PRINT USING "#";
MAXCON; : PRINT ">"; : INPUT ": "; NUMCON$
  IF NUMCON$ = "*" THEN LOCATE 19, 11: PRINT SPC(60); : LOCATE 20, 11: PRINT
SPC(60); : GOTO SHOWRESULTS
  IF NUMCON$ = "" THEN NUMCON$ = "1"
  IF VAL(NUMCON$) < 0 OR VAL(NUMCON$) > MAXCON THEN LOCATE 20, 41: PRINT
SPC(4); : BEEP: GOTO GETCONS
  NUMCON = VAL(NUMCON$)
  FOR CO = 1 TO NUMCON
CON1: LOCATE 20, 11: PRINT SPC(60); : LOCATE 20, 11: PRINT "BLOCK <"; CO; ">:
"; : INPUT CON1$
  IF CON1$ = "*" THEN FOR LI = 19 TO 22: LOCATE LI, 11: PRINT SPC(60); : NEXT
LI: GOTO SHOWRESULTS
  IF CON1$ = "" THEN CON1$ = STR$(CO)
  IF VAL(CON1$) < 1 OR VAL(CON1$) > BLOCK% THEN BEEP: GOTO CON1
  VSBLOCK = CO + 1: IF VSBLOCK > BLOCK% THEN VSBLOCK = BLOCK%
CON2: LOCATE 21, 11: PRINT "BLOCK <"; VSBLOCK; ">: "; : INPUT CON2$
  IF CON2$ = "*" THEN FOR LI = 19 TO 22: LOCATE LI, 11: PRINT SPC(60); : NEXT
LI: GOTO SHOWRESULTS
  IF CON2$ = "" THEN CON2$ = STR$(CO + 1)
  IF VAL(CON2$) < 1 OR VAL(CON2$) > BLOCK% THEN BEEP: GOTO CON2
  CONTRAST(CO, 1) = VAL(CON1$): CONTRAST(CO, 2) = VAL(CON2$)
CONTITLE: LOCATE 22, 11: PRINT SPC(60); : LOCATE 22, 11: INPUT "CONTRAST NAME
<   >: "; CONNAME$(CO)
  IF CONNAME$ = "*" THEN FOR LI = 19 TO 22: LOCATE LI, 11: PRINT SPC(60); :
NEXT LI: GOTO SHOWRESULTS
  'IF CONNAME$ = "" THEN BEEP: GOTO CONTITLE FOR LI = 20 TO 22: LOCATE LI, 11: PRINT SPC(60); : NEXT LI
  NEXT CO
  LOCATE 20, 11: PRINT SPC(60);

SAVEPARAM: LOCATE 19, 11: INPUT "SAVE PARAMETER FILE <Y>: "; SAVEPF$
  IF SAVEPF$ = "*" THEN LOCATE 24, 11: PRINT SPC(60); : LOCATE 19, 11: PRINT
```

```
SPC(60); : GOTO SHOWRESULTS
 SAVEPF$ = UCASE$(SAVEPF$)
 IF SAVEPF$ = "" THEN SAVEPF$ = "Y"
 IF SAVEPF$ <> "Y" AND SAVEPF$ <> "N" THEN LOCATE 19, 38: PRINT SPC(30); :
 BEEP: GOTO SAVEPARAM
 IF SAVEPF$ = "N" THEN LOCATE 1, 1, 0: GOTO OUTOFPARAMS
 IF SAVEPF$ = "Y" THEN LOCATE 24, 29: PRINT "PRESS "; : COLOR 0, 7: PRINT " ?
   "; : COLOR 7, 0: PRINT " TO SEE FILE NAMES "; GETPNAME: LOCATE 20, 11, 1,
   6, 10: PRINT SPC(60); : LOCATE 20, 11: INPUT "ENTER FILE NAME [.SPA]: ";
 OUTPF$
 IF OUTPF$ = "*" THEN LOCATE 20, 11: PRINT SPC(60); : LOCATE 19, 38: PRINT
SPC(4); : LOCATE 24, 28: PRINT SPC(40); : GOTO SAVEPARAM
 IF OUTPF$ = "" THEN BEEP: GOTO GETPNAME
 IF ((LEN(OUTPF$) > 7) OR (INSTR(OUTPF$, ".") > 0)) THEN BEEP: LOCATE 21, 11:
 COLOR 0, 7: PRINT " ONLY 7 CHARACTERS, NO PERIODS ": COLOR 7, 0:   GOTO
 GETPNAME: 'LOCATE 21, 15: PRINT SPC(60); : GOTO GETPNAME
 LOCATE 24, 28: PRINT SPC(40);

GETPOUTDRIVE: LOCATE 21, 11: PRINT SPC(60); : LOCATE 21, 11: INPUT "ENTER
DRIVE <C>: "; POUTDRIVE$
 POUTDRIVE$ = UCASE$(POUTDRIVE$)
 IF POUTDRIVE$ = "*" THEN LOCATE 19, 38: PRINT SPC(4); : LOCATE 20, 11: PRINT
SPC(60); : LOCATE 21, 11: PRINT SPC(60); : GOTO SAVEPARAM
 IF POUTDRIVE$ = "" THEN POUTDRIVE$ = "C"
 ON ERROR GOTO ERRORPROCESS: 'ON ERROR GOTO SAVEPARAM
 IF OUTPF$ = "?" THEN CLS : LOCATE 2, 1: SHELL "DIR " + POUTDRIVE$ +
   ":*.SPA/W": GOTO GETPNAME: 'TOPOF

IF POUTDRIVE$ <> "A" AND POUTDRIVE$ <> "B" AND POUTDRIVE$ <> "C" AND
POUTDRIVE$ <> "D" THEN LOCATE 21, 30: PRINT SPC(30); : BEEP: GOTO
GETPOUTDRIVE
 S$ = ","
 LOCATE 1, 1, 0

OPEN POUTDRIVE$ + ":" + OUTPF$ + ".SPA" FOR OUTPUT AS #1
 PRINT #1, DIGSIZE; S$; MODE$; S$; MID; S$; DIV; S$; MODESET; S$; BLOCK%; S$;
Trials%; S$; TYPEBLOCK$; S$; TBORDER$; S$; TYPEISI$; S$; ISI$; S$; ISI; S$;
KISI$; S$; KISI; S$; SHOWRES$; S$; SHOWCOMP$; S$; NUMCON; S$; StartTRCalc
   FOR CO = 1 TO NUMCON
     PRINT #1, CONTRAST(CO, 1); S$; CONTRAST(CO, 2); S$; CONNAME$(CO)
   NEXT CO
   FOR BL = 1 TO BLOCK%
     PRINT #1, BLFORMAT(BL, 1); S$; BLFORMAT(BL, 2); S$; BLFORMAT(BL, 3); S$;
NOSHOW$(BL); S$; Distracted$(BL, 1); S$; Distracted$(BL, 2)
   NEXT BL
 CLOSE #1: COLOR 31, 0: LOCATE 22, 11: PRINT "SAVING..["; OUTPF$ + ".SPA";
   "]"; : COLOR 7, 0

OUTOFPARAMS:
 IF DIGSIZE = 1 THEN LOWVAL = 1: HIGHVAL = 9 ELSE LOWVAL = 21: HIGHVAL = 99

END SUB

' READSP$.BAS

DECLARE SUB BOX (T!, L!, R!, B!)
DECLARE SUB CLEARKEYBOARD ()
DECLARE SUB ESCAPEIT

DATA 80,114,111,103,114,97,109,109,101,100,32,98,121,32,68,97,118
DATA 105,100,32,74,46,32,83,99,97,114,105,115,98,114,105,99,107,44,32,80
DATA 104,46,68,46

SUB HEADING
'HEADER:
DIM D$(41)
TOPOFHEADER: CLS : CALL CLEARKEYBOARD
TIT$ = "  BUSCHKE COGNITIVE SPEEDOMETER  "
VERSION$ = " Version 4.0 ": SKP2 = (40 - LEN(VERSION$) / 2)
LOCATE 12, (40 - (LEN(TIT$) / 2)): COLOR 31, 0: PRINT TIT$; : COLOR 7, 0
```

```
CALL BOX(T, L, R, B) T = 10: B = 14: L = 19: R = 62: CALL BOX(T, L, R, B)
LOCATE 18, 27: PRINT "Press any key to continue...";

xx$ = ""
WHILE xx$ = ""
   xx$ = INKEY$
WEND
IF xx$ = CHR$(27) THEN GOTO ESCAPEIT: ' GOTO TOPOFHEADER
GOTO BYPASS
ESCAPEIT:
FOR X = 1 TO 41: READ vx: DS(X) = vx: NEXT X
CLS
LOCATE 12, 20: FOR X = 1 TO 41: PRINT CHR$(DS(X)); : NEXT X
xx$ = ""
WHILE xx$ = "": xx$ = INKEY$: WEND
RESTORE
GOTO TOPOFHEADER
BYPASS: '
'DATA 80,114,111,103,114,97,109,109,101,100,32,98,121,32,68,97,118
'DATA 105,100,32,74,46,32,83,99,97,114,105,115,98,114,105,99,107,44,32,80
'DATA 104,46,68,46

END SUB

' SHOWVAL$.BAS

DECLARE SUB CLEARKEYBOARD ()
DECLARE SUB BOX (T!, L!, R!, B!)

SUB SHOWVALUES (ESCAPE$, BADRUN$, SHOWRES$, KEYHIT$, TRIALS%, BLOCK%,
   BlFormat(), NoShow$(), MED(), ALTMED(), NUMCORRECT(), NUMALTCORRECT(),
   SHOWCOMP$, NUMCON, NUMCON$, CONTRAST(), CONNAME$(), CON1$, CON2$, COPYCUT,
   SUBCUT, DIFFCUT, COMPTYPE$, COPTR, SUBTR, DIFFTR, MAXREC, PassPercent,
   PassRun$, StartTRCalc, Distracted$()) STATIC CLS :
 FOR Bl = 1 TO BLOCK%
     IF INT((NUMCORRECT(Bl) / (TRIALS% - StartTRCalc + 1)) * 100) <
PassPercent THEN PassRun$ = "N"
 NEXT Bl
 'prior lines deal with blocks which are less than PassPercent Correct
 IF SHOWRES$ = "N" OR KEYHIT$ = "N" THEN GOTO SKIPIT
 CALL CLEARKEYBOARD
 LOCATE 4, 40 - (LEN(COMPTYPE$) / 2): COLOR 0, 7: PRINT COMPTYPE$;: COLOR 7,0
 LOCATE 6, 30, 0: PRINT "MEDIAN RESPONSE TIMES";
 LOCATE 7, 30: PRINT "     % CORRECT     ";
 T = 8: B = 14: L = 2: R = 78: CALL BOX(T, L, R, B)
 LOCATE 9, 3: ALT$ = "N": COPF$ = "N": SUBF$ = "N"
  LOCATE 9, 3
  FOR Bl = 1 TO BLOCK%
    PRINT SPC(((79 / (BLOCK% + 1)) - 5));
    SELECT CASE BlFormat(Bl, 1)
CASE IS = 1: PRINT "ADD+"; : PRINT USING "#"; BlFormat(Bl, 2);
CASE IS = 2:
    SUBF$ = "Y"
    PRINT "SUB-"; : PRINT USING "#"; BlFormat(Bl, 2);
CASE IS = 3:
    COPF$ = "Y"
    PRINT " COPY";
CASE IS = 4: PRINT "ALT";
    ALT$ = "Y"
    IF NoShow$(Bl) = "Y" THEN PRINT "N";
    IF NoShow$(Bl) = "R" THEN PRINT "R";
    IF NoShow$(Bl) = "N" THEN PRINT "C";
    PRINT USING "#"; BlFormat(Bl, 2);
CASE IS = 5: PRINT "RND";
    ALT$ = "Y"
    IF NoShow$(Bl) = "Y" THEN PRINT "N";
    IF NoShow$(Bl) = "R" THEN PRINT "R";
    IF NoShow$(Bl) = "N" THEN PRINT "C";
```

```
      PRINT USING "#"; BlFormat(Bl, 2);
      CASE ELSE:
      END SELECT
 NEXT Bl
 LOCATE 10, 3
 FOR Bl = 1 TO BLOCK%
  PRINT SPC(((79 / (BLOCK% + 1)) - 5));
  IF Distracted$(Bl, 1) = "Y" AND Distracted$(Bl, 2) = "Y" THEN PRINT "  (";
  : COLOR 31, 0: PRINT "D"; : COLOR 7, 0: PRINT ")";
  IF Distracted$(Bl, 1) = "Y" AND Distracted$(Bl, 2) = "N" THEN PRINT "  (D)
 ";
  IF Distracted$(Bl, 1) = "N" AND Distracted$(Bl, 2) = "N" THEN PRINT "    ";
   COLOR 7, 0
 NEXT Bl
 LOCATE 11, 3
 FOR Bl = 1 TO BLOCK%
   PRINT SPC(((79 / (BLOCK% + 1)) - 5));
   IF BlFormat(1, 1) = 3 AND MED(Bl) > COPYCUT AND Bl = 1 THEN BADRUN$ = "Y":
   COLOR 31, 0
   IF BlFormat(2, 1) = 2 AND MED(Bl) > SUBCUT AND Bl = 2 THEN BADRUN$ = "Y":
   COLOR 31, 0
   IF BlFormat(1, 1) = 2 AND MED(Bl) > SUBCUT AND Bl = 1 THEN BADRUN$ = "Y":
   COLOR 31, 0
   IF BlFormat(2, 1) = 3 AND MED(Bl) > COPYCUT AND Bl = 2 THEN BADRUN$ = "Y":
   COLOR 31, 0
   PRINT USING "#####"; MED(Bl);
   COLOR 7, 0
 NEXT Bl
 COLOR 7, 0
 LOCATE 13, 4
 FOR Bl = 1 TO BLOCK%
   PRINT SPC(((79 / (BLOCK% + 1)) - 5));
   'PRINT "("; : PRINT USING "###"; INT((NUMCORRECT(BL) / TRIALS%) * 100); :
   PRINT ")";
   IF INT((NUMCORRECT(Bl) / (TRIALS% - StartTRCalc + 1)) * 100) < PassPercent
   THEN COLOR 31, 0 ELSE COLOR 7, 0
   PRINT ""; : PRINT USING "###"; INT((NUMCORRECT(Bl) / (TRIALS% -
StartTRCalc + 1)) * 100); : PRINT "% ";
    COLOR 7, 0
 NEXT Bl
 'PRINT SHOWCOMP$;",";NUMCON;",";NUMCON$
 IF SHOWCOMP$ = "N" THEN GOTO WAITFORKEY
 FIRSTCOL = 7: 'DO NOT FLASH SEE TWO LINES DOWN WHERE IT WILL CHANGE TO 31 IF
 CUT
  'IF BLOCK% >= 3 AND NUMCON > 1 THEN LOCATE 16, 29: PRINT "COGNITIVE SPEED"
  IF BLOCK% >= 3 AND NUMCON > 1 THEN LOCATE 16, 5: PRINT "CONTRAST"; SPC(26);
  "TIME"; SPC(12); "COGNITIVE SPEED"
  FOR CO = 1 TO NUMCON
  MedBlockDiff = ABS((MED(CONTRAST(CO, 1)) - MED(CONTRAST(CO, 2))))
  IF MedBlockDiff = 0 THEN MedBlockDiff = 1
  IF BLOCK% = 2 AND DIFFCUT > 0 AND NUMCON = 1 AND (ABS((MED(CONTRAST(CO, 1))
  - MED(CONTRAST(CO, 2))))) > DIFFCUT AND DIFFCUT <> -1 THEN FIRSTCOL = 31
THEN LOCATE 16 + CO, 27: PRINT USING "####.##"; (10000 / MedBlockDiff); :
PRINT " COGS  "; CONNAME$(CO)
  IF BLOCK% > 2 OR (BLOCK% = 2 AND (COPF$ <> "Y" AND SUBF$ <> "Y")) THEN GOTO
PRINTCONTRAST ELSE GOTO COGSPEED
PRINTCONTRAST:
  LOCATE 16 + CO, 5
  FOR Bl = 1 TO 2
  IF Bl = 1 THEN A1 = CONTRAST(CO, 1) ELSE A1 = CONTRAST(CO, 2)
  IF ((BlFormat(A1, 1) = 0) OR (BlFormat(A1, 1) = 3)) THEN PRINT "COPY ";
  IF BlFormat(A1, 1) = 4 THEN PRINT "ALT ";
  IF BlFormat(A1, 1) = 5 THEN PRINT "RND ";
  IF BlFormat(A1, 1) = 4 THEN IF NoShow$(A1) = "Y" THEN PRINT "N";
  IF BlFormat(A1, 1) = 4 THEN IF NoShow$(A1) = "N" THEN PRINT "C";
  IF BlFormat(A1, 1) = 4 THEN IF NoShow$(A1) = "R" THEN PRINT "R";
  IF BlFormat(A1, 1) = 4 THEN PRINT USING "#"; BlFormat(A1, 2);
  IF BlFormat(A1, 1) = 5 THEN IF NoShow$(A1) = "N" THEN PRINT "C";
  IF BlFormat(A1, 1) = 5 THEN IF NoShow$(A1) = "R" THEN PRINT "R";
  IF BlFormat(A1, 1) = 5 THEN PRINT USING "#"; BlFormat(A1, 2);
```

```
    IF BlFormat(A1, 1) = 1 THEN PRINT "ADD+"; : PRINT USING "#"; BlFormat(A1,
2);
    IF BlFormat(A1, 1) = 2 THEN PRINT "SUB-"; : PRINT USING "#"; BlFormat(A1,
2);
    IF Distracted$(A1, 1) = "Y" AND Distracted$(A1, 2) = "Y" THEN PRINT "F(D)";
    IF Distracted$(A1, 1) = "Y" AND Distracted$(A1, 2) = "N" THEN PRINT " (D)";
    IF Distracted$(A1, 1) = "N" AND Distracted$(A1, 2) = "N" THEN PRINT "    ";
    IF Bl = 1 THEN PRINT " vs. ";
NEXT Bl
    IF BLOCK% > 2 OR (BLOCK% = 2 AND (COPF$ <> "Y" AND SUBF$ <> "Y")) THEN
LOCATE 16 + CO, 32: PRINT USING "#######.##"; MedBlockDiff; : PRINT
SPC(13); : PRINT USING "####.##"; (10000 / MedBlockDiff); : PRINT " COGS  ";
  : ' CONNAME$(CO)

COGSPEED: IF NUMCON = 1 AND BLOCK% = 2 AND COPF$ = "Y" AND SUBF$ = "Y" THEN
LOCATE 15 + CO, 27: PRINT "COGNITIVE SPEED ="; : COLOR FIRSTCOL, 0: PRINT
USING "####"; (10000 / ABS((MED(CONTRAST(CO, 1))) - (MED(CONTRAST(CO, 2)))));
  : COLOR 7, 0: PRINT " COGS"; : ' CONNAME$(CO)
    IF NUMCON > 1 AND BLOCK% = 2 AND COPF$ = "Y" AND SUBF$ = "Y" THEN LOCATE 15
    + CO, 19: PRINT "COMPUTATION SPEED"; (CO); " ="; : PRINT USING "####.##";
    (1000 / ABS((MED(CONTRAST(CO, 1)) - MED(CONTRAST(CO, 2))))); : PRINT " COGS
    "; CONNAME$(CO) COLOR 7, 0
BadCogValue:
 NEXT CO
WAITFORKEY: IF BLOCK% = 2 AND COPF$ = "Y" AND SUBF$ = "Y" THEN PROMPT$ = "
PRESS  C  TO SEE CUT SCORES      PRESS ANY KEY TO CONTINUE " ELSE PROMPT$ = "
PRESS ANY KEY TO CONTINUE "
LOCATE 22, 40 - (LEN(PROMPT$) / 2): PRINT PROMPT$;
gg$ = ""
WHILE gg$ = "": gg$ = INKEY$: WEND
    IF gg$ = "C" AND BLOCK% = 2 AND COPF$ = "Y" AND SUBF$ = "Y" THEN LOCATE 20,
8: PRINT "COPY = "; CINT(COPYCUT); "("; COPTR; ")"; "     SUBTR = ";
CINT(SUBCUT); "("; SUBTR; ")"; "     DIFF = "; CINT(DIFFCUT); "("; DIFFTR;
")": IF ALT$ = "Y" THEN _ GOTO GIVEALT ELSE GOTO WAITFORKEYNEW: '
    IF ALT$ = "Y" THEN GOTO GIVEALT ELSE GOTO SKIPIT
GIVEALT:
 CLS
 LOCATE 6, 15: PRINT "MEDIAN RESPONSE TIMES FOR MIXED COPY AND SUBTRACTION";
 LOCATE 7, 31: PRINT "       % CORRECT         ";
 T = 8: B = 15: L = 2: R = 78: CALL BOX(T, L, R, B)
 LOCATE 9, 3:
 FOR Bl = 1 TO BLOCK%
   PRINT SPC(((79 / (BLOCK% + 1)) - 5));
   SELECT CASE BlFormat(Bl, 1)
CASE IS = 4: PRINT "    ALT";
     ALT$ = "Y"
     IF NoShow$(Bl) = "Y" THEN PRINT "N";
     IF NoShow$(Bl) = "R" THEN PRINT "R";
     IF NoShow$(Bl) = "N" THEN PRINT "C";
     PRINT USING "#"; BlFormat(Bl, 2);
CASE IS = 5: PRINT "    RND";
     ALT$ = "Y"
     IF NoShow$(Bl) = "Y" THEN PRINT "N";
     IF NoShow$(Bl) = "R" THEN PRINT "R";
     IF NoShow$(Bl) = "N" THEN PRINT "C";
     PRINT USING "#"; BlFormat(Bl, 2);
   CASE ELSE:
   END SELECT
NEXT Bl LOCATE 10, 3
FOR Bl = 1 TO BLOCK%
   BLO = (2 * Bl) - 1
   IF BlFormat(Bl, 1) >= 4 THEN PRINT SPC(((79 / (BLOCK% + 1)) - 5));
   IF BlFormat(Bl, 1) >= 4 THEN PRINT " COPY"; : PRINT " SUB-"; : PRINT USING
   "#"; BlFormat(Bl, 2);
NEXT Bl

LOCATE 12, 3: PRINT SPC(64);
LOCATE 12, 3
```

```
    FOR B1 = 1 TO BLOCK%
      BLO = (2 * B1) - 1
      IF B1Format(B1, 1) >= 4 THEN PRINT SPC(((79 / (BLOCK% + 1)) - 5));
      IF B1Format(B1, 1) >= 4 THEN PRINT USING "#####"; ALTMED(BLO); ALTMED(BLO
        + 1);
    NEXT B1

LOCATE 14, 4
    FOR B1 = 1 TO BLOCK%
      BLO = (2 * B1) - 1
      IF B1Format(B1, 1) >= 4 THEN PRINT SPC(((79 / (BLOCK% + 1)) - 5));
      IF B1Format(B1, 1) >= 4 THEN PRINT ""; : PRINT USING "###";
      INT((NUMALTCORRECT(BLO) / ((TRIALS% - StartTRCalc + 1) / 2)) * 100); :
        PRINT "% ";
      IF B1Format(B1, 1) >= 4 THEN PRINT ""; : PRINT USING "###";
      INT((NUMALTCORRECT(BLO + 1) / ((TRIALS% - StartTRCalc + 1) / 2)) * 100); :
        PRINT "% ";
    NEXT B1
    IF SHOWCOMP$ = "N" THEN GOTO WAITFORKEYNEW
    WAITFORKEYNEW: 'LOCATE 23, 5: PRINT SPC(73); : LOCATE 23, 27: COLOR 0, 7:
    INPUT " PRESS ANY KEY TO CONTINUE "; gg$: COLOR 7, 0
    LOCATE 22, 5: PRINT SPC(73); : LOCATE 23, 28: PRINT " PRESS ANY KEY TO
      CONTINUE "; xx$
      xx$ = "": WHILE xx$ = "": xx$ = INKEY$: WEND
      IF xx$ = "" THEN GOTO SKIPIT

SKIPIT:

END SUB

' $SPEED.MAX $SPEED.BAS
    PURERAND.BAS
    STEMLEAF.BAS
    BYMEAN_.BAS
    PRESTIM.BAS
    PERINFO.BAS
    MINUSVAL.BAS
    PARAMSP$.BAS
    HEADSP$.BAS
    SHOWVAL$.BAS
```

I claim:

1. A cognitive speedometer for the assessment of cognitive processing speed, comprising:
   (A) display means;
   (B) means for entering data;
   (C) means for generating original data and displaying on said display means the original data for copying by a user on said data entry means;
   (D) means, operable only on the displayed original data correctly copied by the user on said data entry means, for generating and displaying on said display means different data on which the user is to perform a unit cognitive operation and then enter the resultant data on said data entry means; and
   (E) means, operable only on the correct resultant data entered by the user on said data entry means, for determining the time required for the user to perform only the unit cognitive operation.

2. The cognitive speedometer of claim 1 wherein said determining means determines the time required for the user to perform the unit cognitive operation as the difference between the time required to copy the displayed original data correctly on said data entry means and the time required to perform a unit cognitive operation on the displayed different data and then enter the resultant data correctly on said data entry means.

3. The cognitive speedometer of claim 2 wherein said determining means determines the difference between the determined times by calculation.

4. The cognitive speedometer of claim 1 wherein said determining means determines the time required to perform the unit cognitive operation independently of the time required to physically enter the resultant data on said data entry means.

5. The cognitive speedometer of claim 1 additionally including means for comparing the time required for the user to perform the unit cognitive operation with an established norm for the time required to perform the unit cognitive operation.

6. The cognitive speedometer of claim 5 wherein said comparing means compares the time required for the user to perform the unit cognitive operation as determined by said determining means with an established norm determined by use of said cognitive speedometer on comparable, similarly situated individuals.

7. The cognitive speedometer of claim 5 wherein said comparing means compares the time required to perform the unit cognitive operation as determined by said determining means with a norm established for the individual user by prior use of said cognitive speedometer.

8. The cognitive speedometer of claim 1 wherein said original and different data are numeric, and the unit cognitive operation is arithmetic.

9. The cognitive speedometer of claim 8 wherein said numeric data is a number having no more than two digits.

10. The cognitive speedometer of claim 1 wherein the unit cognitive operation is the addition of or subtraction of 1 from the displayed different data.

11. The cognitive speedometer of claim 1 additionally including prompting means for indicating on said display means at an appropriate time the unit cognitive operation to be performed by the user on the displayed different data.

12. The cognitive speedometer of claim 11 additionally including prompting means for displaying on said display means at an appropriate time instructions for the user to copy the displayed original data.

13. The cognitive speedometer of claim 1 additionally including means for determining the user's speed of cognitive processing per unit of time by dividing a unit of time by the number of unit cognitive operations performed per unit of time by the user.

14. The cognitive speedometer of claim 1 wherein said means for generating and displaying original data generates and displays a sequence of such original data for copying before said means for generating and displaying the different data displays such different data.

15. The cognitive speedometer of claim 1 wherein the resultant data is the same as the original data.

16. A cognitive speedometer for the assessment of cognitive processing speed, comprising;
(A) display means;
(B) means for entering data;
(C) means for generating original data and displaying on said display means the original data for copying by a user on said data entry means;
(D) means, operable only on the displayed original data correctly copied by the user on said data entry means, for generating and displaying on said display means different data on which the user is to perform a unit cognitive operation and then enter the resultant data on said data entry means, the resultant data having the same characters as the original data, said original, different and resultant data being numbers having no more than two digits each and the unit cognitive operation being the addition of 1 to or subtraction of 1 from the displayed different data;
(E) means, operable only on the correct resultant data entered by the user on said data entry means, for determining the time required for the user to perform only a unit cognitive operation independently of the time required to physically enter the resultant data on said data entry means, said determining means determining the time as the difference between the time required to copy the displayed original data correctly on said data entry means and the time required to perform a unit cognitive operation on the displayed different data and then enter the resultant data correctly on said data entry means;
(F) means for comparing the time required for the user to perform the unit cognitive operation with a established norm for the time required to perform the unit cognitive operation; and
(G) prompting means for displaying on said display means at an appropriate time instructions for the user to copy the displayed original data and for indicating on said display means at an appropriate time the unit cognitive operation to be performed by the user on the displayed different data;
said means for generating and displaying original data generating and displaying a sequence of such original data for copying before said means for generating and displaying the different data displays such different data.

17. The cognitive speedometer of claim 16 wherein said comparing means compares the time required for the user to perform the unit cognitive operation as determined by said determining means with an established norm determined by use of said cognitive speedometer on comparable, similarly situated individuals.

18. The cognitive speedometer of claim 16 wherein said comparing means compares the time required to perform the unit cognitive operation as determined by said determining means with a norm established for the individual user by prior use of said cognitive speedometer.

19. A cognometer comprising in combination in a single portable device:
(A) a speed monitor means including a cognitive speedometer for the assessment of cognitive processing speed;
(B) a memory monitor means;
(C) a concentration monitor means; and
(D) means for selectively actuating one of said monitor means at a time;
wherein said speed monitor means, memory monitor means and concentration monitor means, having a common data entry means and a common display means.

20. A method of assessing cognitive speed comprising the steps of:
(A) generating and displaying data on a display means;
(B) testing the user's speed of entering original data by displaying the original data on the display means and requiring the user to copy the original data on the data entry means;
(C) testing the cognitive speed of the user by displaying different data on the display means and requiring the user to perform a unit cognitive operation on the different data and enter the resultant data corresponding only to the original data correctly copied by the user, on the data entry means; and
(D) determining the time required for the user to perform only a unit cognitive operation on the displayed different data.

21. The method of claim 20 wherein the original data and the resultant data are the same.

22. The method of claim 20 wherein the time is determined in step (D) only with regard to the resultant data correctly entered by the user.

23. A cognitive speedometer for the assessment of cognitive processing speed, comprising:
(A) display means;
(B) means for entering data;
(C) means for generating and displaying on said display means data on which the user is to perform a plurality of tasks involving different numbers of unit cognitive operations and then enter the resultant data on said data entry means; and
(D) means for determining the time required for the user to perform only a unit cognitive operation from the times required to perform the tasks.

24. The cognitive speedometer of claim 23 wherein said determining means determines the time required for the user to perform the unit cognitive operation as the slope of the linear function associated with the set of points in X, Y coordinates, where Y is the variable associated with the time required for the user to perform the tasks and then enter the resultant data on said data entry means, and X is the variable associated with the number of unit cognitive operations involved in the respective tasks.

25. The cognitive speedometer of claim 23 wherein said determining means uses only the tasks for which the user enters the correct resultant data on said data entry means.

26. The cognitive speedometer of claim 23 wherein said determining means determines the time required to perform the unit cognitive operation independently of the time required to physically enter the resultant data on said data entry means.

27. A method of assessing cognitive speed comprising the steps of:
(A) generating and displaying data on a display means;
(B) testing the cognitive speed of the user by requiring the user to perform a plurality of tasks involving different numbers of unit cognitive operations on the data and enter the resultant data on the data entry means; and
(C) determining the time required for the user to perform only a unit cognitive operation from the times required to perform the tasks.

28. The method of claim 27 wherein the time required for the user to perform the unit cognitive operation is determined as the slope of the linear function associated with the set of points in X, Y coordinates, where Y is the variable associated with the time required for the user to perform the tasks and then enter the resultant data on the data entry means, and X is the variable associated with the number of unit cognitive operations involved in the respective tasks.

29. The method of claim 27 wherein the time required for the user to perform the unit cognitive operation is determined using only the tasks for which the user enters the correct resultant data on the data entry means.

30. The method of claim 27 wherein the time required to perform the unit cognitive operation is determined independently of the time required for the user to physically enter the resultant data on the data entry means.

* * * * *